US010569090B2

(12) United States Patent
Hulings et al.

(10) Patent No.: US 10,569,090 B2
(45) Date of Patent: Feb. 25, 2020

(54) SYSTEMS, DEVICES, AND METHODS FOR PROVIDING ELECTROTHERAPY

(71) Applicant: ZOLL Medical Corporation, Chelmsford, MA (US)

(72) Inventors: Robert J. Hulings, Mars, PA (US); Scott D. Quinnell, Kittanning, PA (US); Ronald A. Seman, Pittsburgh, PA (US); Dale Ballard, Glenshaw, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 250 days.

(21) Appl. No.: 15/796,043

(22) Filed: Oct. 27, 2017

(65) Prior Publication Data

US 2018/0117326 A1 May 3, 2018

Related U.S. Application Data

(60) Provisional application No. 62/414,232, filed on Oct. 28, 2016.

(51) Int. Cl.
*A61N 1/362* (2006.01)
*A61N 1/04* (2006.01)
(Continued)

(52) U.S. Cl.
CPC ........... *A61N 1/3625* (2013.01); *A61N 1/046* (2013.01); *A61N 1/36014* (2013.01);
(Continued)

(58) Field of Classification Search
CPC .. A61N 1/3625; A61N 1/046; A61N 1/36014; A61N 1/042; A61N 1/0484; A61N 1/0492; A61H 39/002
See application file for complete search history.

(56) References Cited

U.S. PATENT DOCUMENTS 3,405,845 A 10/1968 Cook et al.
4,928,690 A 5/1990 Heilman et al.
(Continued)

FOREIGN PATENT DOCUMENTS

EP 0 459 239 A2 12/1991
WO 92/19571 11/1992
WO 2016/149450 A1 9/2016

OTHER PUBLICATIONS

International Search Report from the ISA (PCT/US2017/058748) dated Feb. 26, 2018.

*Primary Examiner* — Lindsey G Wehrheim
(74) *Attorney, Agent, or Firm* — ZOLL Medical Corporation

(57) ABSTRACT

Systems, devices and methods for providing a pressurized fluid for facilitating conductive gel release prior to providing cardiac therapy to a patient are disclosed. A first system can include a chemical reaction chamber including a first chemical and a second chemical isolated from each other by a mechanical barrier. The mechanical barrier is configured to be compromised upon receiving a signal from an electrotherapy device controller such that the first chemical and second chemical come into contact to produce a sufficient amount of pressurized fluid. An alternative system can include a pressure source comprising a reservoir containing a pressurized fluid. The pressure source can also include at least one release mechanism configured to cause a release of the pressurized fluid from the reservoir to an exit port of the pressure source when a wearable medical device is preparing to deliver a therapeutic shock to a patient.

31 Claims, 13 Drawing Sheets

(51) Int. Cl.
*A61N 1/36* (2006.01)
*A61H 39/00* (2006.01)

(52) U.S. Cl.
CPC ............ *A61H 39/002* (2013.01); *A61N 1/042* (2013.01); *A61N 1/0484* (2013.01); *A61N 1/0492* (2013.01)

(56) References Cited

U.S. PATENT DOCUMENTS

| | | |
|---|---|---|
| 5,700,245 A | 12/1997 | Sancoff et al. |
| 6,301,502 B1 | 10/2001 | Owen et al. |
| 9,037,271 B2 | 5/2015 | Kaib et al. |
| 9,321,581 B2 | 4/2016 | Bennison et al. |
| 9,861,806 B2 | 1/2018 | Kaib et al. |
| 2002/0156461 A1 | 10/2002 | Joshi |
| 2012/0150008 A1 | 6/2012 | Kaib et al. |
| 2012/0150164 A1 | 6/2012 | Lee et al. |
| 2014/0249613 A1 | 9/2014 | Kaib |
| 2015/0005588 A1 | 1/2015 | Herken et al. |
| 2018/0001101 A1 | 1/2018 | Hulings et al. |

SYSTEMS, DEVICES, AND METHODS FOR PROVIDING ELECTROTHERAPY

CROSS-REFERENCE TO RELATED APPLICATIONS

The present application claims the benefit under 35 U.S.C. § 119(e) of U.S. provisional application Ser. No. 62/414,232 filed on Oct. 28, 2016, the disclosure of which is hereby expressly incorporated by reference in its entirety.

BACKGROUND

The present disclosure is directed to medical therapy systems, and more particularly, to electrode systems such as therapy electrodes including pressure sources.

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

To protect against cardiac arrest and other cardiac health ailments, some at-risk subjects may use a non-invasive bodily-attached ambulatory medical monitoring and treatment device, such as the LifeVest® wearable cardioverter defibrillator available from ZOLL Medical Corporation. To remain protected, the subject wears the device nearly continuously while going about their normal daily activities, while awake, and while asleep.

Such medical devices work by providing one or more shocks to a patient. Prior to delivering the one or more shocks, a conductive gel deployment device can release a conductive gel about a conductive surface of a therapy electrode such that the one or more shocks can be directed from the therapy electrode to the patient's skin.

SUMMARY

In some implementations, an electrode for providing electrotherapy from an ambulatory electrotherapy device comprising: at least one reservoir comprising a conductive gel; at least one pressure source comprising a chemical reaction chamber comprising a first chemical and a second chemical isolated from each other by a mechanical barrier, wherein the mechanical barrier is configured to be compromised upon receiving a signal from an electrotherapy device controller, and wherein the first chemical and second chemical come into contact when the mechanical barrier is compromised to produce a sufficient amount of fluid to generate a sufficient pressure within the chamber, is provided.

In some implementations, the electrode further comprises at least one release mechanism configured to compromise the mechanical barrier, thereby releasing the second chemical such that the second chemical reacts with the first chemical.

In some implementations, the at least one release mechanism comprises a heat producing device.

In some implementations, the at least one release mechanism comprises a mechanical device configured to facilitate movement of at least one of the first chemical and the second chemical.

In some implementations, the mechanical barrier comprises at least one meltable membrane configured to isolate the first chemical from the second chemical.

In some implementations, the electrode further comprises a resistive wire in contact with the at least one meltable membrane and configured to produce a heat to melt the at least one meltable membrane.

In some implementations, the electrode further comprises an exit port connected to a fluid channel, wherein the exit port is configured to direct the pressurized fluid into the fluid channel.

In some implementations, a pressure level of the produced fluid is between 15 psi and 40 psi.

In some implementations, a system for providing therapy to a patient, the system comprising: a garment; a monitor configured to monitor at least a physiological parameter of a patient; and a plurality of therapy electrodes operably connected to the monitor and disposed in the garment, each of the plurality of therapy electrodes comprising a pressure source for providing a pressurized fluid to facilitate conductive gel deployment in a wearable medical device, the pressure source comprising a chemical reaction chamber comprising a first chemical and a second chemical isolated from each other by a mechanical barrier, wherein the mechanical barrier is configured to be compromised upon receiving a signal from an electrotherapy device controller, and wherein the first chemical and second chemical come into contact when the mechanical barrier is compromised to produce a sufficient amount of fluid to generate a sufficient pressure within the chamber, is provided.

In some implementations, each of the plurality of therapy electrodes further comprise at least one conductive surface configured to deliver a therapeutic shock.

In some implementations, the system further comprises at least one release mechanism configured to compromise the mechanical barrier, thereby releasing the second chemical such that the second chemical reacts with the first chemical.

In some implementations, the at least one release mechanism comprises a heat producing device.

In some implementations, the at least one release mechanism comprises a mechanical device configured to facilitate movement of at least one of the first chemical and the second chemical.

In some implementations, a pressure level of the produced fluid is between 15 psi and 40 psi.

In some implementations, a pressure source for providing a pressurized fluid to facilitate conductive gel deployment in a wearable medical device, the pressure source comprising: a reservoir containing a pressurized fluid; and at least one release mechanism configured to cause a release of the pressurized fluid from the reservoir to an exit port of the pressure source when the wearable medical device is preparing to deliver a therapeutic shock to a patient, is provided.

In some implementations, the at least one release mechanism comprises at least one heating element.

In some implementations, the reservoir comprises a meltable plug positioned in contact with the at least one heating element and configured to melt upon application of a current to the at least one heating element, thereby resulting in release of the pressurized fluid through the exit port.

In some implementations, the meltable plug comprises at least one of a metal solder and an epoxy resin.

In some implementations, the pressure source further comprises: a piercing device positioned adjacent to a pierceable end of the reservoir; and a spring mechanism configured to facilitate movement of at least one of the piercing device and the reservoir, thereby resulting in a piercing of the pierceable end of the reservoir and release of the pressurized fluid through the exit port.

In some implementations, the spring mechanism comprises a meltable retaining mechanism positioned adjacent to at least one heating element, wherein the meltable retaining mechanism is configured to melt upon application of a current to the at least one heating element, thereby resulting in the movement of at least one of the piercing device and the reservoir.

In some implementations, the piercing device comprises a drill positioned such that a drill bit is adjacent to the pierceable end of the reservoir.

In some implementations, application of a current to the drill results in rotational movement of the drill bit such that the drill bit penetrates the pierceable end of the reservoir.

In some implementations, the at least one release mechanism comprises a piston position to block flow of the pressurized fluid from the reservoir to the exit port, wherein the piston is configured to slidably release the pressurized fluid to the exit port.

In some implementations, the pressure source further comprises: a spring mechanism configured to slide the piston to facilitate release of the pressurized fluid.

In some implementations, the pressure source further comprises at least one retaining element configured to oppose a spring force exerted by the spring mechanism to prevent movement of the piston, wherein the at least one retaining element is positioned adjacent to at least one heating element and is configured to melt upon application of a current to the at least one heating element, thereby resulting in movement of the piston and release of the pressurized fluid to the exit port.

In some implementations, the at least one release mechanism comprises a movable piercing device positioned adjacent to a pierceable end of the reservoir.

In some implementations, the moveable piercing device comprises a motor configured to move puncturing device through into the pierceable end of the reservoir, thereby resulting in release of the pressurized fluid.

In some implementations, the motor comprises at least one of a solenoid and an expanding wax actuator.

In some implementations, a pressure level of the pressurized fluid after release is between 15 psi and 40 psi.

In some implementations, a system for providing therapy to a patient, the system comprising: a garment; a monitor configured to monitor at least a physiological parameter of a patient; and a plurality of therapy electrodes operably connected to the monitor and disposed in the garment, each of the plurality of therapy electrodes comprising a pressure source for providing a pressurized fluid to facilitate conductive gel deployment in a wearable medical device, the pressure source comprising a reservoir containing a pressurized fluid, and at least one release mechanism configured to cause a release of the pressurized fluid from the reservoir to an exit port of the pressure source when the monitor is preparing to deliver a therapeutic shock to a patient, is provided.

In some implementations, each of the plurality of therapy electrode further comprise at least one conductive surface configured to deliver the therapeutic shock.

In some implementations, the at least one release mechanism comprises: at least one heating element; and a meltable plug positioned in contact with the at least one heating element and configured to melt upon application of a current to the at least one heating element, thereby resulting in release of the pressurized fluid through the exit port.

In some implementations, the pressure source further comprises: a piercing device positioned adjacent to a pierceable end of the reservoir; and a spring mechanism configured to facilitate movement of at least one of the piercing device and the reservoir, thereby resulting in a piercing of the pierceable end of the reservoir and release of the pressurized fluid through the exit port.

In some implementations, the at least one release mechanism comprises a piston position to block flow of the pressurized fluid from the reservoir to the exit port, wherein the piston is configured to slidably release the pressurized fluid to the exit port.

In some implementations, the at least one release mechanism comprises a movable piercing device positioned adjacent to a pierceable end of the reservoir.

In some implementations, a pressure level of the pressurized fluid after release is between 15 psi and 40 psi.

In some implementations, a method for providing electrotherapy from an ambulatory electrotherapy device comprising: providing an electrode; providing at least one reservoir comprising a conductive gel; providing at least one pressure source comprising a chemical reaction chamber comprising a first chemical and a second chemical isolated from each other by a mechanical barrier, wherein the mechanical barrier is configured to be compromised upon receiving a signal from an electrotherapy device controller, and wherein the first chemical and second chemical come into contact when the mechanical barrier is compromised to produce a sufficient amount of fluid to generate a sufficient pressure within the chamber, is provided.

In some implementations, the pressure source comprises producing carbon dioxide by a reaction of the first chemical and the second chemical.

In some implementations, the first chemical is a metal carbonate or bicarbonate and the second chemical is an acid.

In some implementations, an amount of the metal carbonate or bicarbonate and the acid is sufficient to produce carbon dioxide in an amount to supply the sufficient pressure of from about 15 psi to about 50 psi.

In some implementations, the pressure source comprises producing carbon dioxide, nitrogen, oxygen, or mixtures thereof.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
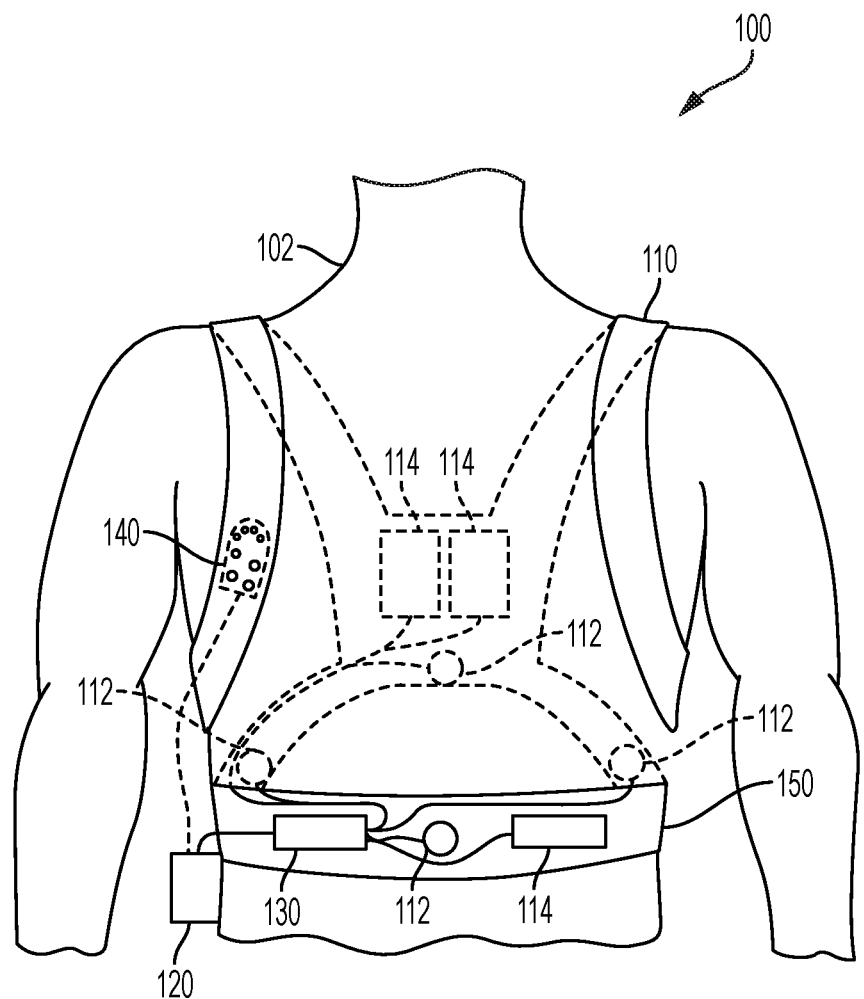
FIG. 1 depicts a wearable medical device, in accordance with an example of the present disclosure.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

As used herein, the term "about" or "approximately" when referring to a measurable value such as an amount, a pressure, and the like, is meant to encompass variations of +/−10%, more preferably +/−5%, even more preferably, +/−1%, and still more preferably +/−0.1% from the specified value, as such variations are appropriate to perform the disclosed methods.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

This disclosure relates to improvements to a pressure source for facilitating release and distribution of conductive gel for use with, for example, a wearable defibrillator. As will be defined in detail below, various designs can be used for a pressure source that include various alternatives for creating or causing the release of a pressurized fluid. Upon creation or release of the pressurized fluid, the pressurized fluid facilitates deployment of, for example, conductive gel prior to delivery of a therapeutic shock to a patient.

During operation, and prior to administering a therapeutic shock, one or more components of a wearable defibrillator can facilitate release of a conductive gel. For example, the wearable defibrillator can include a gel deployment device configured to release a quantity of conductive gel between a therapy electrode and a patient's skin. The conductive gel can be stored within one or more gel reservoirs in the gel deployment device until released. In order to release the conductive gel, the gel deployment device can include one or more pressure sources configured to generate or release a pressurized fluid. The pressurized fluid can be directed such that the pressurized fluid mechanically pushes the conductive gel out of the gel reservoirs. Various pressure source configurations and implementations are described herein in greater detail.

In one or more examples, the pressure sources as described herein can be configured to produce or release a pressurized fluid at a predetermined pressure configured to cause release of the conductive gel from the conductive gel reservoirs. For example, a pressure source can be configured to create or release a pressurized fluid having a pressure of approximately 15 psi to 40 psi. In order to facilitate conductive gel release. In some implementations, the pressure sources can be configured to produce or release a pressurized fluid at about 35 psi. In other examples, the pressure sources can be configured such that they release a pressurized fluid that is configured to fill a certain cavity or space to a specific pressure. In certain implementations, the pressure sources can be configured to release a pressurized fluid such that a cavity or other open space is pressurized to a pressure of about 15 psi to 40 psi. In some configurations, the pressure sources can be configured to release a pressurized fluid such that a cavity or other open space is pressurized to a pressure of about 35 psi. In some examples, the pressure sources can be configured to produce an applied force (e.g., 10.5 N/cm$^2$/sec to 26.5 N/cm$^2$/sec). Though the following description related to levels of pressure produced by the pressure sources (e.g., in pounds per square inch), it should be appreciated that the functioning of the pressure sources as detailed herein can be described by way of exerted force as well.

It should be noted that the above described pressure sources are merely shown as introductory examples, and additional details are provided in the following discussions of the figures.

As described below in additional detail, various configurations can be used for a pressure source. In some examples, the pressure source is configured to facilitate a chemical reaction therein. As a result of the chemical reaction, an amount of pressurized fluid such as carbon dioxide gas is produced and directed to, for example, a plurality of conductive gel reservoirs for facilitating release of the conductive gel stored therein.

The pressurized fluid can include any non-noxious gas, such as carbon dioxide, carbon monoxide, nitrogen, oxygen, nitric oxide, nitrogen dioxide, nitrous oxide, hydrogen, fluorine, chlorine, helium, neon, argon, krypton, xenon, radon, or mixtures thereof. In some implementations, the pressurized fluid includes carbon dioxide, nitrogen, oxygen, nitrogen dioxide, hydrogen, helium, neon, argon, krypton, xenon, radon, or mixtures thereof. In some implementations, the pressurized fluid includes carbon dioxide, nitrogen, oxygen, or mixtures thereof.

In another set of example pressure sources, a pressurized fluid reservoir is loaded with an amount of pressurized fluid such as compressed nitrogen gas or compressed carbon dioxide gas. In certain implementations, a mechanical release mechanism is configured to pierce or otherwise compromise the integrity of the pressurized fluid reservoir, thereby releasing the pressurized fluid. In some examples, a mechanical release mechanism is configured to open a fluid conduit or otherwise establish a fluid connection between the pressurized fluid reservoir and an exit port.

Example Medical Devices

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114, a medical device controller 120, a connection pod 130, a patient interface pod 140, a belt 150, or any combination of these. In some examples, at least some of the components of the wearable medical device 100 can be configured to be affixed to the garment 110 (or in some examples, permanently integrated into the garment 110), which can be worn about the patient's torso.

The controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The controller 120 can be operatively coupled to the therapy electrodes 114. For example, the therapy electrodes 114 can also be assembled into the garment 110, or, in some implementations, the therapy electrodes 114 can be permanently integrated into the garment 110. Additionally, the therapy electrodes 114 can include one or more conductive gel deployment devices, e.g., as shown in U.S. Patent Application Publication No. 2015/0005588 entitled "Therapeutic Device Including Acoustic Sensor," the content of which is incorporate herein by reference. Additional examples of gel deployment devices can be found in, for example, U.S. patent application Ser. No. 15/196,638 filed Jun. 29, 2016 and entitled "Conductive Gel Release and Distribution Devices," the content of which is hereby incorporated by reference in its entirety.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

The sensing electrodes 112 can be configured to detect one or more cardiac signals. Examples of such signals include ECG signals, heart sounds, and/or other sensed cardiac physiological signals from the patient. The sensing electrodes 112 can also be configured to detect other types of patient physiological parameters, such as tissue fluid levels, lung sounds, respiration sounds, patient movement, etc. In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the controller 120.

Figure 2:
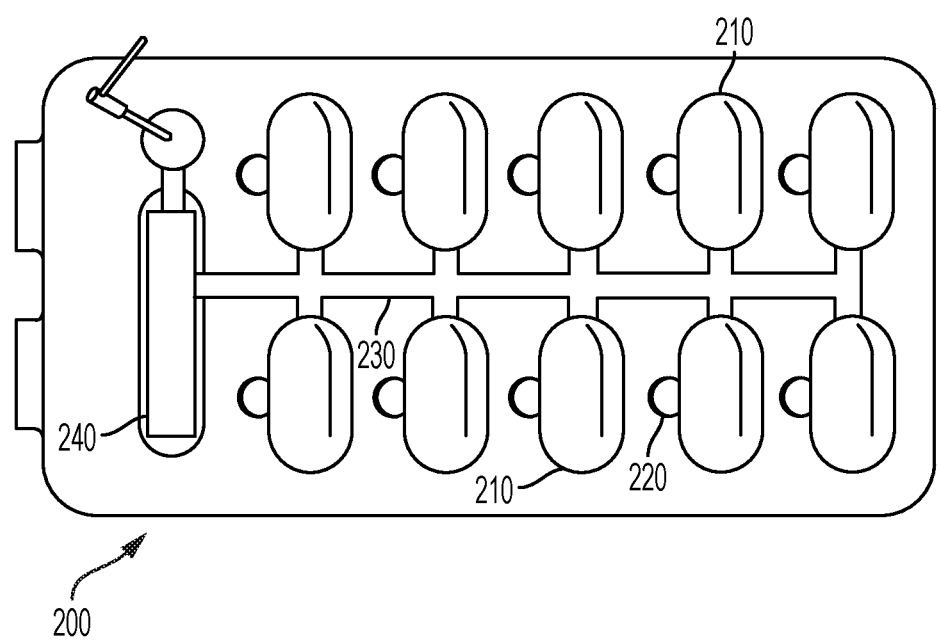
FIG. 2 depicts a plan view of a therapy electrode that can be used with the wearable medical device of FIG. 1.

FIG. 2 is a plan view of an electrode portion of a therapy electrode assembly that includes a gel deployment device and which can be used with a wearable medical device, such as the wearable defibrillator described above with respect to FIG. 1. The gel deployment device, when activated, can dispense an electrically conductive gel onto the exposed surface of the electrode portion of the therapy electrode assembly that, in use, is placed most proximate to the subject's body.

As shown in FIG. 2, the electrode portion 200 can be a multiple layer laminated structure that includes an electrically conductive layer (disposed on the bottom surface of the therapy electrode 200). In use, the electrically conductive layer can be disposed substantially adjacent to the subject's skin, although the conductive layer need not make direct contact with the subject, as portions of the garment 110 (as shown in FIG. 1) and/or portions of the subject's clothing can be present between the electrically conductive layer and the subject's skin. In some implementations, the garment 110 can include a pocket or other similar structure including a metallic mesh that can be configured to act as an interface between the electrically conductive layer and the patient's skin. In an example, the metallic mesh can include a knotted fabric having a silver coating. Upon deployment of the conductive gel, an electrical pathway can be defined between the electrically conductive layer and the patient's skin.

As shown in FIG. 2, various components of the gel deployment device can be disposed on a side of the therapy electrode 200 (e.g., the top-side shown in FIG. 2) that is opposite the side on which the conductive layer is formed.

The therapy electrode 200 can include a plurality of conductive gel reservoirs 210, each of which has a respective gel delivery outlet 220. Each of the gel reservoirs can be fluidly coupled to a fluid channel 230 and a pressure source 240. The pressure source 240 can be fluidly coupled to the fluid channel 230 and, when activated by an activation signal, can release a pressurized fluid, such as compressed gas, into the channel 230. The hydraulic pressure of the fluid from the activated pressure source 240 in the fluid channel 230 can force the conductive gel stored in each of the plurality of gel reservoirs out of the plurality of gel delivery outlets 220 through apertures formed in the electrically conductive layer and onto the exposed surface of the electrically conductive layer that, in use, is placed most proximate to the subject's body. The apertures in the electrically conductive layer can be substantially aligned with the plurality of gel delivery outlets 220 so that when activated, the electrically conductive gel can be dispensed onto the exposed surface of the electrode portion that is disposed most proximate to the subject's body.

Overview of Pressure Sources Using Chemical Reactions

As noted above, a pressure source can be configured to facilitate a chemical reaction. As a result of the chemical reaction, an amount of pressurized fluid can be produced and directed to, for example, a plurality of conductive gel reservoirs for facilitating release of the conductive gel stored therein.

The pressurized fluid can include any non-noxious gas. Examples are discussed above.

Figure 3:
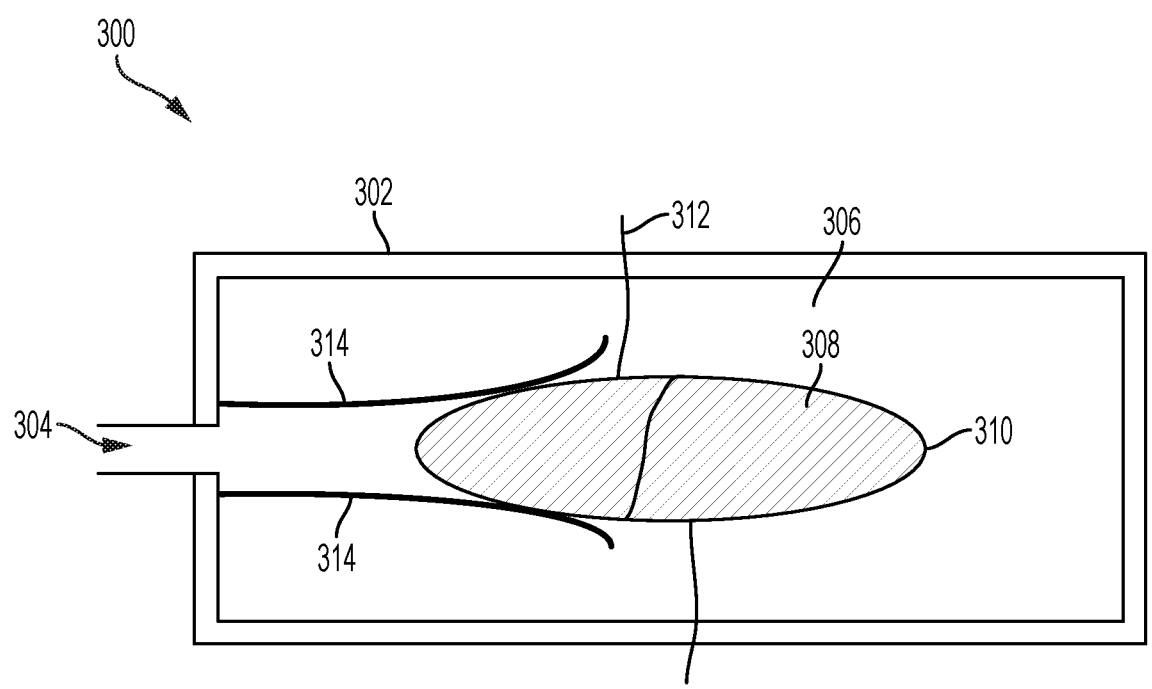
FIG. 3 depicts a pressure source that uses a chemical reaction to produce a pressurized fluid, in accordance with an example of the present disclosure.
Figure 4:
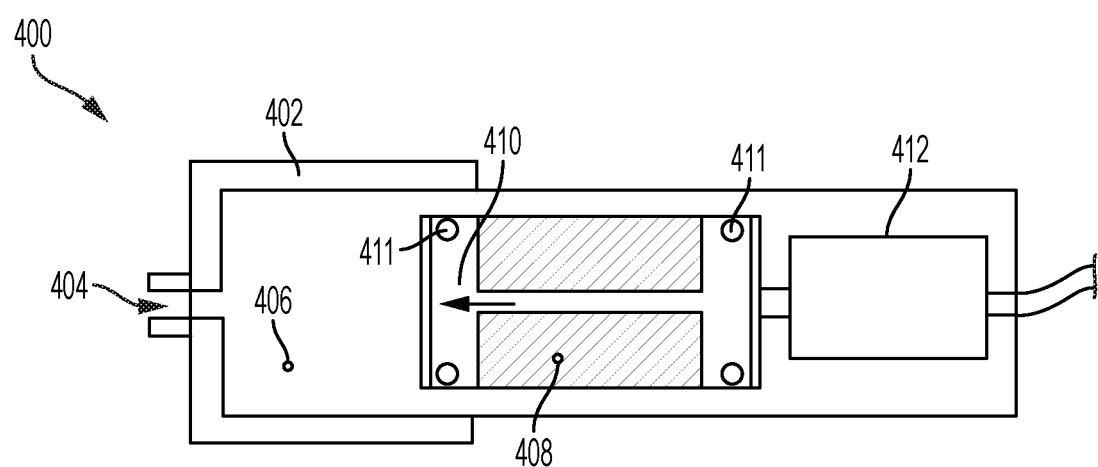
FIG. 4 depicts a pressure source that uses a chemical reaction to produce a pressurized fluid, in accordance with an example of the present disclosure.

FIGS. 3 and 4 illustrate various example configurations for a pressure source that incorporates a chemical reaction to produce a pressurized fluid. The pressure sources can include a case design that allows for the storage and timely mixing of two or more chemicals to produce the pressurized fluid. For example, the chemical reaction can include mixing two chemicals together to produce a chemical reaction, resulting in the creation of a pressurized fluid. The chemical reaction can include, for example, mixing two or more fluids together, mixing one or more fluids with one or more solids, or mixing two or more solids together.

In certain implementations, the chemical reaction can include mixing an acid with a base to produce a pressurized fluid. The resulting carbon dioxide gas can be directed by the pressure source through an exit port of the pressure source and into, for example, fluid channel 230 as described above. The carbon dioxide gas can apply hydraulic pressure to the individual gel reservoirs 210, thereby facilitating release of conductive gel stored within the conductive gel reservoirs.

Depending upon the intended application of the pressure source, a certain pressure level of the pressurized fluid can be configured to, for example, facilitate conductive gel release in a conductive gel deployment device. For example, the pressure level of the pressurized fluid can be configured based upon the internal volume of the fluid channel (as well as any additional spaces the pressurized fluid is configured to fill, such as air gaps or spaces in the gel reservoirs). The pressure level can also be configured based upon an applied pressure level for releasing the conductive gel from the gel reservoirs. In certain implementations, the gel reservoirs can include a frangible seal configured to release the conductive gel at an applied pressure of about 15 psi. This applied pressure, in combination with the internal volume the pressurized fluid is configured to fill, can be used to determine a total overall pressure level for the pressurized fluid. For example, the combined internal volume the pressurized fluid is configured to fill can be approximately 25 cubic centimeters. In other examples, the internal volume the pressurized fluid is configured to fill can be approximately 5-50 $cm^3$. In other examples, the internal volume can change as the conductive gel is released (i.e., to account for the space in the gel reservoirs previously occupied by the conductive gel). As such, in certain implementations, the initial internal volume can be approximate 5-10 $cm^3$ and the final internal volume can be approximately 10-50 $cm^3$.

In some implementations, the pressure sources including chemical reactions as described below can be configured to produce or release a pressurized fluid at approximately 5 to 100 psi. In some implementations, the pressure sources including chemical reactions as described below can be configured to produce or release a pressurized fluid at approximately 15 psi to 40 psi. In some examples, the pressure sources including chemical reactions can be configured to produce or release a pressurized fluid at about 35 psi, or at a similar pressure to fill the internal volume (such as a one or more fluid conduits used in a gel deployment device as described above) to a pressure of about 35 psi.

It should be noted that the combination of an acid and a base as described above to produce a pressurized gas is presented by way of example only.

In certain implementations, the chemical reaction can include applying an acidic solution to a reactive metal.

Additionally, while the following discussions are generally directed to chemical reactions, physical reactions can be included as well. For example, a nucleation process can be used to produce an amount of pressurized fluid.

In some implementations, a liquid including a suspended gas (such as a carbonated liquid including suspended carbon dioxide) can be mixed with a solid including a surface covered with microscopic features such as peaks and valleys. When the solid is introduce to the liquid, the suspended gas attaches to the microscopic features, forming bubbles around all the features. Once the amount of forming bubbles exceeds the amount of gas the liquid can stably suspend, excess gas can be released from the liquid as a pressurized fluid. As above, this pressurized fluid can be directed to the gel reservoirs for facilitation of the conductive gel release.

Specific examples of pressure sources including chemical reactions are described below in additional detail.

Chemical Reaction Example Using a Heat Source

FIG. 3 illustrates a pressure source 300 configured to produce a pressurized fluid as, for example, a byproduct of a chemical reaction. In operation, the pressure source 300 can be integrated into a therapy electrode such as therapy electrode 200 as discussed above, e.g., replacing pressure source 240 as discussed in reference to therapy electrode 200. A controller, such as medical device controller 120, can be operably connected to the pressure source 300. The medical device controller 120 can be configured to provide an electrical signal to the pressure source 300 prior to delivery of, for example, a therapeutic shock to a patient. The electrical signal can be configured to facilitate or otherwise initiate a chemical reaction configured to produce a pressurized fluid. The pressurized fluid can then be directed through the fluid channel 230 to the conductive gel reservoirs 210, thereby causing release of the conductive gel stored therein.

The pressurized fluid can include any non-noxious gas. Examples are discussed above.

The pressure source 300 can include a case 302 configured to contain the chemicals and other components related to facilitating a chemical reaction. Depending upon the design of the pressure source 300, and the types of chemicals contained therein, various materials and methods of manufacture can be used to construct the case 302. For example, the chemical reaction used by the pressure source 300 can be configured to produce approximately 35 psi. As such, the material used for the manufacture of case 302 can be selected and configured to withstand an applied pressure greater than 35 psi plus some safety margin (e.g., an additional about 1-50 psi). The case 302 can be made of plastic, metal, metal alloy, ceramic, and/or a combination thereof. In certain implementations, the case 302 can be molded from a thermoplastic polymer and/or a thermoset polymer. In some examples, the case 302 can be shaped such that any pressurized fluids contained therein are directed in a particular direction. For example, the case 302 can be shaped like a cone having an opening or exit port at the point or narrow end, a tapering cylinder having an opening or exit port at the narrow end, a pyramid having an opening or exit port at one of the points, and other similar shapes that provide one or more geometric features for directed pressurized fluid flow.

In some implementations, the case 302 is made of a clear or transparent material to allow visual monitoring of the contents of the case.

The case 302 can be made of a thermoplastic material. For example, the thermoplastic material can be high density polyethylene, low density polyethylene, ultra high-molecular weight polyethylene, polypropylene, nylon and polyethylene terephthalate. Alternatively, it is understood that any viable thermoplastic material may be used. The material may be transparent, opaque or partially opaque.

Examples of thermoplastic polymers include polystyrene, polyetherketone, polyetherketone, polyetherketoneketone, polyethersulfone, polycarbonate, polyolefin such as polypropylene, polyethylene, or cyclic olefin, polyester such as polyethylene terephthalate or polyethylene napthalate, polyamide (nylon), or other well-known materials in the plastics art. Amorphous plastics such as amorphous nylon exhibit high transparency and may also be suitable.

Thermoset resins include epoxy, epoxy novolac, phenolic, polyurethane, and polyimide.

In some implementations, the case 302 can be manufactured from a copolymer such as an ethylene acid copolymer through an injection molding or thermoforming process. For example, the case 302 can be manufactured from an ionomer resin of ethylene acid copolymer ("the ionomer resin") having a density of approximately 0.94 g/cm$^3$. As such, the tensile strength of the ionomer resin can be configured based upon the thickness of the ionomer resin. An example of a commercially available ionomer resin of ethylene acid copolymer is Surlyn®, which is available from DuPont™.

The thickness of the walls of the case 302 can be configured such that the case 302 is configured to withstand an applied pressure of greater than, for example, about 100 psi. In certain implementations, the ionomer resin has a thickness of approximately 0.125 inches can withstand an applied pressure of approximately 250 psi.

In certain implementations, a clear plastic such as polycarbonate or a composite plastic blend (e.g., an ethylene acid copolymer and polycarbonate blend) can be used to manufacture case 302 if, for example, the case 302 is to be subjected to visual inspection (e.g., to confirm that the chemical reaction has not occurred prior to installation of the pressure source). Depending upon the tensile strength of the blended materials, a thickness for the walls of the case 302 can be configured such that the case is configured to withstand the applied pressure as described above.

Additionally, case 302 can be manufactured from a material having a relatively low water vapor transmission rate. The ionomer resin has a water vapor transmission rate of about 0.8 g/100 in$^2$/day. Using a material with a low permeability such as the ionomer resin can provide an advantage of a longer shelf-life of a chemical reaction-based pressure source relative to conventional configurations as the rate of evaporation of any liquid chemicals through the ionomer resin is low.

In certain implementations, the case 302 can be manufactured from a plastic material using an injection molding process. In certain implementations, the case 302 can be manufactured from the ionomer resin in a design (e.g., having a specific geometry and wall thickness) capable of both housing enough chemicals as needed for the chemical reaction while still maintaining its structural integrity after the chemical reaction (e.g., the case 302 is configured to handle the pressure of the fluid produced as a result of the chemical reaction). In additional implementations, the case 302 can be formed by a thermoforming process, or other similar forming process.

The case 302 can also be made from a non-reactive metal such as stainless steel. The stainless steel can be stamped, rolled, or similarly formed to contain the chemicals and other components related to facilitating the chemical reaction.

In certain implementations, the case 302 can be configured and formed such that it defines at least one exit port 304 for directing a pressurized fluid (produced by, for example, a chemical reaction within the case 302). Depending upon the design of the pressure source 300, the exit port 304 can include a valve (e.g., a one-way flow valve) to prevent contamination or foreign chemicals from entering into the case 302. In certain implementations, the valve can be configured to open at a predetermined pressure (e.g., about 5 psi to 20 psi) to prevent chemicals from escaping the case 302 prior to the chemical reaction. In some examples, the valve can be configured to open at about 10 psi.

The pressure source 300 can include a first chemical 306 and a second chemical 308. The first chemical 306 can be a solid base loaded into the case 302 in, for example, a powder or compressed solid form. The second chemical 308 can be contained in an isolating container 310. The isolating container 310 can be configured to act as a mechanical barrier positioned to provide isolation of the second chemical 308 from the first chemical 306 until the second chemical 308 is released or otherwise mixed with first chemical 306, thereby eliminating unwanted and/or untimely reactions.

The second chemical 308 can be a liquid chemical such as an acid. The isolating container 310 can be filled with the second chemical prior to insertion into the case 302. In certain implementations, to facilitate ejection of the second chemical 308 from the isolating container 310, the second chemical 308 can be filled into the isolating container 310 at, for example, 15 psi to 35 psi.

In some examples, the second chemical 308 can be filled into the isolating container 310 at about 25 psi. Thus, when the isolating container 310 is compromised, the second chemical 308 is forcibly released from the isolating container 310. In certain implementations, an external pressure applying device such as a leaf spring or an elastic band can apply an external pressure to the isolating container 310. For example, as shown in FIG. 3, a set of leaf springs 314 can be positioned adjacent to the isolating container 310 and be configured to apply an external pushing force against the isolating container 310. When the isolating container 310 is compromised, the leaf springs 314 can assist in the release of the second chemical 308 from the isolating container 310.

In some implementations, the first chemical 306 is a metal carbonate or bicarbonate and the second chemical 308 is an acid. When the metal carbonate or bicarbonate and the acid mix together, a reaction occurs to produce carbon dioxide, salt, and water.

The metal carbonate can be any metal carbonate. In some implementations, the metal carbonate is lithium carbonate, sodium carbonate, potassium carbonate, rubidium carbonate, cesium carbonate, beryllium carbonate, magnesium carbonate, calcium carbonate, strontium carbonate, barium carbonate, manganese carbonate, iron carbonate (siderite), cobalt carbonate, nickel carbonate, copper carbonate, zinc carbonate, silver carbonate, cadmium carbonate (otavite), aluminum carbonate, thallium carbonate, lead carbonate, ammonium carbonate, bismuth subcarbonate, lanthanum carbonate, uranyl carbonate, or mixtures thereof. In some implementations, the metal carbonate is sodium carbonate, potassium carbonate, magnesium carbonate, calcium carbonate, copper carbonate, zinc carbonate, ammonium carbonate, or mixtures thereof.

The metal bicarbonate can be any metal bicarbonate. In some implementations, the metal bicarbonate is lithium bicarbonate, sodium bicarbonate, potassium bicarbonate, cesium bicarbonate, magnesium bicarbonate, calcium bicarbonate, ammonium bicarbonate, or mixtures thereof. In some implementations, the metal bicarbonate is sodium bicarbonate, potassium bicarbonate, magnesium bicarbonate, calcium bicarbonate, ammonium bicarbonate, or mixtures thereof.

The acid can be any acid in a concentration such that it can react to produce carbon dioxide but can be safely stored in the case 302. The acid can be a mineral acid, sulfonic acid, carboxylic acid, halogenated carboxylic acid, or mixtures thereof. In some implementations, the acid is hydrofluoric acid, hydrochloric acid, hydrobromic acid, hydroiodic acid, hypochlorous acid, chlorous acid, chloric acid, perchloric acid, hypobromous acid, bromous acid, bromic acid, perbromic acid, hypoiodous acid, iodous acid, iodic acid, periodic acid, sulfuric acid, nitric acid, phosphoric acid, fluorosulfuric acid, fluoroantimonic acid, fluoroboric acid, hexafluorophosphoric acid, chromic acid, methanesulfonic acid, ethanesulfonic acid, benzensulfonic acid, p-toluenesulfonic acid, trifluoromethanesulfonic acid, polystyrene sulfonic acid, acetic acid, citric acid, formic acid, gluconic acid, lactic acid, oxalic acid, tartaric acid fluoroacetic acid, tirfluoroacetic acid, chloroacetic acid, dichloroacetic acid, trichloroacetic acid, ascorbic acid, or mixtures thereof. In some implementations, the acid is hydrochloric acid, sulfuric acid, nitric acid, phosphoric acid, acetic acid, or mixtures thereof.

The concentration of the acid can be adjusted by adding a solvent such as water. In some implementations, the concentration of the acid is adjusted such that the pH of the acid is in the range of about 2 to less than 7. In some implementations, acids with a pH of less than 2 can be used in small quantities—e.g., less than 0.1 gm in case having a volume of about 25 $cm^3$.

In some implementations, the pressure source 300 can include a first chemical 306 and a second chemical 308, wherein the first chemical 306 and the second chemical 308 are selected to produce nitrogen gas or oxygen gas.

To produce oxygen gas, the first chemical 306 can be sodium chlorate, potassium perchlorate, potassium permanganate, potassium iodide, or mixtures thereof and the second chemical 308 can be hydrogen peroxide, barium peroxide, iron powder, or mixtures thereof. Yeast can be used as the first chemical 306 in some implementations. In some implementations, the second chemical 308 is hydrogen peroxide. In some implementations, the second chemical 308 is hydrogen peroxide and the first chemical 306 can be one or a mixture of potassium iodide, yeast, and potassium permanganate.

To produce nitrogen gas, the first chemical 306 can be an ammonium compound and the second chemical 308 can be a chemical that reacts with the ammonium compound to produce nitrogen gas. Examples of the ammonium compound include ammonium nitrite, ammonium nitrate, ammonium, chloride, ammonium dichromate, ammonium hydroxide, or mixtures thereof. Examples the second chemical 408 can be sodium nitrite, potassium nitrite, calcium nitrite, or other nitrite compound.

Nitrogen gas can also be produced by the reaction of hypochlorites or hypobromites on ammonia, reduction of nitric and/or nitrous oxides, reaction of ammonia gas with a nitrite compound, or combinations of these reactions.

It should be noted that the quantities provided of the first chemical 306 and the second chemical 308 can be varied depending upon the size and shape of the case 302 and the amount of pressure the chemical reaction is configured to produce. For example, to produce a higher pressure than, for example, the implementations as described above, additional quantities of the first chemical 306 and the second chemical 308 can be used in a similarly shaped case 302. In some implementations, more reactive chemicals can be used to produce a pressurized fluid having a higher pressure level.

The first chemical 306 can be added in an amount of about 0.001 grams to about 1000 grams. In some embodiments the first chemical 306 can be added in an amount of 0.001 to about 50 wt % of the total amount of the first chemical 306 and the second chemical 308. The second chemical 308 can be added in an amount of about 0.001 grams to about 1000 grams. In some embodiments the second chemical 308 can be added in an amount of 0.001 to about 50 wt % of the total amount of the first chemical 306 and the second chemical 308.

In some embodiments, the first chemical 306 and the second chemical 308 are present in an amount sufficient to produce an amount of carbon dioxide, which produces a pressure of from about 5 psi to about 100 psi. In some implementation, the pressure is from about 10 psi to about 70 psi. In some implementations, the pressure is from about 15 psi to about 50 psi. In some implementations, the pressure is from about 15 psi to about 35 psi.

In certain implementations, the isolating container 310 can be made from a membrane or another material that, in response to an applied heat or force, can be structurally compromised to release the second chemical 308 such that it mixes with the first chemical 306. In certain implementations, the isolating container 310 can be configured such that it is structurally compromised upon application of heat from one or more heat sources. For example, as shown in FIG. 3, a heating element such as resistive wire 312 can be placed adjacent to the isolating container 310, e.g., wrapped around the isolating container 310 or otherwise pressed against a portion of the isolating container 310. The isolating container 310 can be formed from a meltable membrane such as a thermoplastic configured to melt at a predetermined melting point. In certain implementations, the isolating container 310 can be manufactured from polyethylene having a melting point of approximately 239-275° F. In some examples, the isolating container 310 can be manufactured from a material having a low evaporation permeability (e.g., a material having a low water vapor transmission rating) when compared to conventional thermoplastics. A material with a low evaporation permeability can provide the advantage of an extended shelf life of the pressure source 300 as the second chemical 308 is less likely to evaporate or leak from the isolating container 310.

The resistive wire 312 can be constructed from a material that produces heat in response to an applied current. For example, the resistive wire 312 can be made from nickel chromium wire. The thickness of the resistive wire 312 can be selected such that the temperature of the wire, when an appropriate current is applied, exceeds the melting point of the isolating container 310. For example, a 20-gauge to a 28-gauge wire can be used, the wire configured to heat to approximately 350° F. to 450° F. In certain implementations, a 24-gauge nickel chromium wire having a 0.020-inch diameter can heat to 400° F. at relatively low amperages as compared to a similarly sized copper wire.

In order to facilitate mixing of the first chemical 306 and the second chemical 308, a current can be applied to the resistive wire 312. The resistive wire 312 can heat up past the melting point of the isolating container 310, thereby causing a puncturing or rupturing of the isolating container 310 and release of the second chemical 308 (e.g., through the internal pressure of the second chemical 308 within the isolating container 310 as described above). The second chemical 308 can mix with the first chemical 306, thereby producing a pressurized fluid. The shape of the case 302 can direct the pressurized fluid out of the exit port 304. The exit port 304 can be connected to a fluid channel in, for example, the therapy electrode 200 as described above in regard to FIG. 2. The pressurized fluid can be directed through the fluid channel to one or more gel reservoirs, thereby facilitating release of conductive gel stored in the gel reservoirs.

In certain implementations, alternate release methods can be used to puncture or otherwise compromise the isolating container 310 and release the second chemical 308. For example, a puncturing pin and actuation device (such as a small solenoid) can be used to puncture the isolating container 310. In certain implementations, the isolating container 310 can be configured as a syringe configured to eject a quantity of the second chemical 308 in response to, for example, a force pressing against a plunger of the syringe. In some examples, an alternative melting device can be used in place of the resistive wire 312. For example, a small laser can be configured to focus an emitted laser beam or pulse onto the isolating container 310 to melt a small portion of the isolating container 310.

Depending upon the resistance of the resistive wire 312, and desired timing for the release of the conductive gel, the medical device controller 120 can be configured to deliver an appropriate electrical signal (e.g., at a high enough current to heat the resistive wire 312) at the appropriate time (e.g., providing for adequate timing for the chemical reaction to occur and for the subsequent release of the conductive gel). In some examples, the pressure source 300 can also include a localized power source that, in response to the signal from the medical device controller 120, is configured to provide a current to the resistive wire 312, thereby heating the resistive wire.

As noted above, in operation, the pressure source 300 can be integrated into a therapy electrode such as therapy electrode 200 as discussed above, e.g., replacing pressure source 240 as discussed in reference to therapy electrode 200. A controller, such as medical device controller 120, can be operably connected to the pressure source 300. The medical device controller 120 can be configured to provide an electrical signal to the pressure source 300 prior to delivery of, for example, a therapeutic shock to a patient. The electrical signal can include a current to be directed to the resistive wire 312, thereby heating the resistive wire 312. Once heated, the resistive wire 312 can melt the isolating container 310, resulting in the release of the second chemical 308 from the isolating container 310. The second chemical 308 can mix with the first chemical 306, causing a chemical reaction. The chemical reaction can produce a pressurized fluid (e.g., pressurized carbon dioxide gas), which is directed through the exit port 304. The pressurized fluid can flow through the fluid channel 230 to each of the conductive gel reservoirs 210. The pressurized fluid can cause release of the conductive gel contained within the conductive gel reservoirs 210, thereby resulting in the conductive gel flowing through the apertures in the electrically conductive layer that is substantially proximate the patient's body. The medical device controller 120 can then facilitate delivery of the therapeutic shock.

It should be noted that the arrangement of components as shown in FIG. 3 is by way of example only. For example, the isolating container 310 is shown as positioned in the center of the case 302 for explanatory purposes only. In certain implementations, the isolating container 310 can be positioned against a wall of the case 302, at one end of the case 302, or at any location within the case 302 that still provides for adequate chemical mixing prior to the chemical reaction. Additionally, the pressure source 300 is shown as having the second chemical 308 positioned inside the isolating container 310. In other designs, the first chemical 306 can be placed within the isolating container 310 and the second chemical 308 can be arranged solely inside case 302.

Chemical Reaction Example Using a Movable Piston

FIG. 4 illustrates a pressure source 400 configured to produce a pressurized fluid as a result of a chemical reaction. In operation, the pressure source 400 can be integrated into a therapy electrode such as therapy electrode 200 as discussed above, e.g., replacing pressure source 240 as discussed in reference to therapy electrode 200. A controller, such as medical device controller 120, can be operably connected to the pressure source 400. The medical device controller 120 can be configured to provide an electrical signal to the pressure source 400 prior to delivery of, for example, a therapeutic shock to a patient. The electrical signal can be configured to facilitate or otherwise initiate a chemical reaction configured to produce a pressurized fluid. The pressurized fluid can then be directed through the fluid channel 230 to the conductive gel reservoirs 210, thereby causing release of the conductive gel stored therein.

The pressurized fluid can include any non-noxious gas. Examples are discussed above.

The pressure source 400 can include a case 402 configured to contain the chemicals and other components related to facilitating a chemical reaction. The case 402 can be formed such that it can define at least one exit port 404 for directing a pressurized fluid (produced by, for example, a chemical reaction within the case 402). Depending upon the design of the pressure source 400, the exit port 404 can include a valve (e.g., a one-way flow valve) to prevent contamination or foreign chemicals from entering into the case 402. Similarly, the valve can be configured to open at a predetermined pressure (e.g., 10 psi) to prevent chemicals from escaping the case 402 prior to the chemical reaction.

As described above in regard to case 302, case 402 can be made from the same material(s) and has the same characteristics as discussed above with regard to case 302.

The pressure source 400 can include a first chemical 406 and a second chemical 408. The first chemical 406 can be a metal carbonate or bicarbonate. In some implementations, the first chemical 406 can be a solid such as sodium bicarbonate loaded into the case 402 in, for example a powder or compressed solid form.

The second chemical 408 remains separated from the first chemical 406 by, for example, a piston 410. In some implementations, the second chemical 408 is an acid.

The metal carbonate can be any metal carbonate, as discussed above.

The metal bicarbonate can be any metal bicarbonate as discussed above.

The acid can be any acid as discussed above.

In certain implementations, the piston 410 can be constructed from a plastic such as polyethylene, or a metal such as stainless steel or aluminum. The piston 410 can also include one or more O-rings 411 positioned to prevent leakage of the second chemical 408 as well as to act as a mechanical barrier configured to create a seal between the first chemical and the second chemical. In some implementations, the O-rings 411 can be made from a thermoplastic elastomer such as synthetic rubber. The O-rings 411 can also be sized to produce a friction fit between the piston 410 and the case 402.

To facilitate movement of the piston 410, and thus mixing of the first chemical 406 and the second chemical 408, the piston 410 can be connected to a movement causing device such as a solenoid 412. The solenoid 412 can be configured to exert a pushing force on the piston 410, thereby moving the piston 410 toward the first chemical 406 (as shown in FIG. 4), causing the release of the second chemical 408 into the first chemical 406. The second chemical 408 can mix with the first chemical 406, thereby producing a pressurized fluid. In certain implementations, the shape of the case 402 can be configured and design to direct the pressurized fluid out of the exit port 404. The exit port 404 can be connected to a fluid channel in, for example, the therapy electrode 200 as described above in regard to FIG. 2. The pressurized fluid can be directed through the fluid channel to one or more gel reservoirs, thereby facilitating release of conductive gel stored in the gel reservoirs.

Depending upon the electrical requirements of the solenoid 412, and desired timing for the release of the conductive gel, the medical device controller 120 can be configured to deliver an appropriate electrical signal (e.g., at a high enough current to move the solenoid 412) at the appropriate time (e.g., providing for adequate timing for the chemical reaction to occur and for the subsequent release of the conductive gel). In some implementations, the pressure source 400 can also include a localized power source that, in response to the signal from the medical device controller 120, is configured to provide a current to the solenoid 412, thereby facilitating movement of the solenoid 412.

As noted above, the pressure source 400 can be integrated into a therapy electrode such as therapy electrode 200. For example, the pressure source 400 can replace pressure source 240 as discussed in reference to therapy electrode 200. A controller, such as medical device controller 120, can be operably connected to the pressure source 400. The medical device controller 120 can be configured to provide an electrical signal to the pressure source 400 prior to delivery of, for example, a therapeutic shock to a patient. The electrical signal can be directed to the solenoid 412. The solenoid 412 can move the piston 410 toward, for example, exit port 404. Such movement of the piston 410 can result in the second chemical 408 being released into the first chemical 406.

The second chemical 408 can mix with the first chemical 406, causing a chemical reaction. The chemical reaction can produce a pressurized fluid (e.g., pressurized carbon dioxide gas) which can be directed through the exit port 404. The pressurized fluid can flow through the fluid channel 230 to each of the conductive gel reservoirs 210. The pressurized fluid can facilitate release of the conductive gel contained within the conductive gel reservoirs 210, resulting in the conductive gel flowing through the apertures in the electrically conductive layer that is proximate the patient's body. The medical device controller 120 can then deliver the therapeutic shock.

It should be noted that pressure sources 300 and 400 are described above by way of example only. Similarly, the chemicals described in relation to the pressure sources 300 and 400, as well as the resulting chemical reactions and pressurized fluids produced by those reactions are described by way of example only.

In some implementations, the pressure source 400 can include a first chemical 406 and a second chemical 408, wherein the first chemical 406 and the second chemical 408 are selected to produce nitrogen gas or oxygen gas.

To produce oxygen gas, the first chemical 406 can be sodium chlorate, potassium perchlorate, potassium permanganate, potassium iodide, or mixtures thereof and the second chemical 408 can be hydrogen peroxide, barium peroxide, iron powder, or mixtures thereof. Yeast can be used as the first chemical 406 in some implementations. In some implementations, the second chemical 408 is hydrogen peroxide. In some implementations, the second chemical 408 is hydrogen peroxide and the first chemical 406 can be one or a mixture of potassium iodide, yeast, and potassium permanganate.

To produce nitrogen gas, the first chemical 406 can be an ammonium compound and the second chemical 408 can be a chemical that reacts with the ammonium compound to produce nitrogen gas. Examples of the ammonium compound include ammonium nitrite, ammonium nitrate, ammonium, chloride, ammonium dichromate, ammonium hydroxide, or mixtures thereof. Examples the second chemical 408 can be sodium nitrite, potassium nitrite, calcium nitrite, or other nitrite compound.

Nitrogen gas can also be produced by the reaction of hypochlorites or hypobromites on ammonia, reduction of nitric and/or nitrous oxides, reaction of ammonia gas with a nitrite compound, or combinations of these reactions.

Chemical Reaction Examples

As described above, a pressure source (e.g., one of pressure sources 300 and 400) can include two chemicals configured to mix such that a resulting reaction produces an amount of pressurized fluid containing a gas such as carbon dioxide.

The pressurized fluid can include any non-noxious gas. Examples are discussed above.

In some implementations, the pressurized fluid is produced from mixing a first chemical and a second chemical to produce carbon dioxide, where the first chemical is a metal carbonate or bicarbonate and the second chemical is an acid. The reaction of the metal carbonate or bicarbonate with the acid produces safe byproducts including salt, water, and carbon dioxide as shown below in reaction (1).

$$\text{Metal Carbonate or Bicarbonate} + \text{Acid} \rightarrow \text{Salt} + \text{Water} + \text{Carbon Dioxide} \quad (1)$$

For example, the chemical reaction can include mixing an acid such as citric or acetic acid with a basic solid such as sodium bicarbonate to produce carbon dioxide gas with water, and sodium acetate. A specific chemical reaction example of reaction (1) is shown below in reaction (2).

$$NaHCO_3 + CH_3COOH \rightarrow CO_2 + H_2O + CH_3COONa \quad (2)$$

The base can be added in an amount of about 0.001 grams to about 1000 grams. In some embodiments the base can be added in an amount of 0.001 to about 50 wt % of the total amount of the base and the acid. The acid can be added in an amount of about 0.001 grams to about 1000 grams. In some embodiments the acid can be added in an amount of 0.001 to about 50 wt % of the total amount of the base and the acid.

In certain implementations, the first chemical or the second chemical can be a limiting agent. For example, a specific quantity of the first chemical can be determine that, upon reaction, will produce an appropriate amount of pressurized gas. An amount of the second chemical can be determine that would fully react with the specific quantity of the first chemical. In certain embodiments, an additional buffer amount of the second chemical can be included. For example, an additional 5-25% of the second chemical can be included. In such an example, the first chemical would act as a limiting agent as the first chemical would fully react with the second chemical (with an amount of excess second chemical remaining, i.e., the additional buffer).

In some embodiments, the base and the acid are present in an amount sufficient to produce an amount of carbon dioxide, which produces a pressure of from about 5 psi to about 100 psi. In some implementations, the pressure is from about 10 psi to about 70 psi. In some implementations, the pressure is from about 15 psi to about 50 psi. In some implementations, the pressure is from about 15 psi to about 35 psi.

As noted above, a specific amount of pressurized fluid can be created during the chemical reaction, the pressurized fluid being directed to individual gel reservoirs to facilitate release of conductive gel stored therein. For example, the pressurized fluid can be configured to fill an internal volume of 25 cm³ to a pressure of approximately 50 psi (e.g., a 35 psi pressure to facilitate release of the conductive gel from the gel reservoirs plus a 15 psi safety buffer to account for any unreacted chemicals or other potential complications during the chemical reaction). In the above example chemical reaction, the resulting pressurized fluid is carbon dioxide, which has a molar mass of 44.0095 g/mol at room temperature (e.g., approximately 295K). As such, based upon the desired pressure (50 psi at standard atmospheric pressure), the internal volume (25 cm³), and the molar mass of the carbon dioxide, an amount of carbon dioxide to be produced during the chemical reaction can be calculated using the ideal gas law:

$$pV = nRT \quad (3)$$

where p is the pressure, V is the volume, n is the number of moles of the gas (represented as mass/mass of 1 mole), R is the ideal gas constant (8.31446 J K⁻¹ mol⁻¹), and T is the temperature at the time of reaction (e.g., approximately 295K or room temperature). As noted above, the pressure includes a safety buffer. This buffer can also be used to account for any changes in temperature during the reaction.

Substituting the values as noted above into the ideal gas law, the resulting equation is:

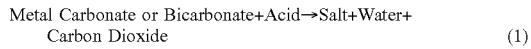
(50 psi at 1 atm)(25 cm³)=(mass of CO₂/44.0095 g/mol)(8.31441 J K⁻¹ mol⁻¹)(295K).

Converting both pressure and volume to appropriate units (Pascal and cubic meters respectively) results in:

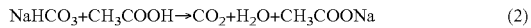
(344737.86 pa)(0.000025 m³)=(mass of CO₂/44.0095 g/mol)(8.31446 J K⁻¹ mol⁻¹)(295K).

Solving the above equation gives a mass of 0.15 g of $CO_2$ to be produced. Such a mass of $CO_2$ will result in the desired 50 psi in the internal volume of 25 cm³. $CO_2$ has a density of about 1.98 g/L in its gaseous state. As such, the above equation results in 0.075 liters of $CO_2$. Thus, a chemical reaction that produces 0.075 liters of $CO_2$ will result in a 50 psi pressure in the internal volume of 25 cm³.

See Table 1 for calculations showing the amounts of sodium bicarbonate and acetic acid needed to produce a range of pressures (i.e., 1-100 psi) from the resulting carbon dioxide gas in a volume of 25 cm³.

The inventors have used commercially available acetic acid to produce carbon dioxide.

When the controller, e.g., medical device controller 120, triggers a release of the conductive gel, the wire 312 can be heated, thereby causing a structural compromise of the isolating container 310 (e.g., the wire 312 melts a hole in isolating container 310). The acetic acid can then be released from the isolating container 310. In certain implementations, leaf springs 314 can provide an external force against the isolating container 310, causing quicker release of the acetic acid. The acetic acid can then mix with the sodium bicarbonate in the case 302, causing creation of the carbon dioxide gas. The carbon dioxide gas can be directed out of the case 302 via the exit port 304. The carbon dioxide gas can then be directed by one or more fluid conduits, such as fluid channel 230, to the gel reservoirs.

In certain implementations, the speed of the reaction can be a critical consideration. For example, in a wearable defibrillator, when a treatment shock is imminent, it may be desirable to have the conductive gel deploy as quick as possible. In such an implementation, the amounts of the chemicals can be changed to produce a quicker reaction. For example, the amounts of sodium bicarbonate and acetic acid can be increased. In certain implementations, a pressure source can include between 0.50 grams and 2.5 grams of sodium bicarbonate. Similarly, a pressure source can include between 0.40 grams and 2.2 grams of acetic acid. In a particular example, a pressure source can include 1.5 grams of sodium bicarbonate and 0.50 grams of acetic acid. As the acetic acid is used in a liquid state, a lower ratio (as compared to the total amount of chemicals used in the reaction) of acetic acid can be used as compared to the ratio of the solid sodium bicarbonate. By including a higher ratio of the sodium bicarbonate, the chances are increased that the acetic acid will fully react with the sodium bicarbonate, thereby maximizing the amount of carbon dioxide gas that can be produced by the amount of acetic acid used. Any excess sodium bicarbonate will remain in the pressure source in an unreacted state.

As noted above, the internal volume that the pressurized fluid is intended to fill can vary between implementation as well. For example, as noted above, the total internal volume can vary between 10-50 cm$^3$. When the internal volume is less than the volume as used in the above calculations (25 cm$^3$), the amount of the individual chemicals can be reduced as a lesser amount of pressurized fluid may be used. Conversely, when the internal volume is greater than the volume as used in the above calculations, the amount of the individual chemicals can be increased as a greater amount of pressurized fluid may be used. For example, a pressure source can include between 0.25 grams and 5 grams of sodium bicarbonate. Similarly, a pressure source can include between 0.15 and 4 grams of acetic acid.

In addition to changing the quantities of the chemicals used, changing the chemicals reacting with one another to produce a different gas can be used to control both the volume and speed of a reaction. Instead of producing carbon dioxide, as discussed above, oxygen or nitrogen can be generated from a chemical reaction.

In some implementations, the pressure source 300 can include a first chemical 306 and a second chemical 308, wherein the first chemical 306 and the second chemical 208 are selected to produce nitrogen gas or oxygen gas.

To produce oxygen gas, the first chemical 306 can be sodium chlorate, potassium perchlorate, potassium permanganate, potassium iodide, or mixtures thereof and the second chemical 308 can be hydrogen peroxide, barium peroxide, iron powder, or mixtures thereof. Yeast can be used as the first chemical 306 in some implementations. In some implementations, the second chemical 308 is hydrogen peroxide. In some implementations, the second chemical 308 is hydrogen peroxide and the first chemical 306 can be one or a mixture of potassium iodide, yeast, and potassium permanganate.

To produce nitrogen gas, the first chemical 306 can be an ammonium compound and the second chemical 308 can be a chemical that reacts with the ammonium compound to produce nitrogen gas. Examples of the ammonium compound include ammonium nitrite, ammonium nitrate, ammonium, chloride, ammonium dichromate, ammonium hydroxide, or mixtures thereof. Examples the second chemical 308 can be sodium nitrite, potassium nitrite, calcium nitrite, or other nitrite compound.

Nitrogen gas can also be produced by the reaction of hypochlorites or hypobromites on ammonia, reduction of nitric and/or nitrous oxides, reaction of ammonia gas with a nitrite compound, or combinations of these reactions.

For example, the chemical reaction can include mixing an aqueous peroxide such as hydrogen peroxide with a metallic salt such as potassium iodide to produce oxygen gas. Such a reaction results in the catalyzed decomposition of the hydrogen peroxide to produce water and oxygen gas. Specifically, the hydrogen peroxide reacts with iodide ions from the potassium iodide to produce the oxygen gas. For example, the reactions can be represented as:

$$H_2O_2 + I^- \rightarrow H_2O + IO^- \quad (4)$$

$$H_2O_2 + IO^- \rightarrow H_2O + O_2 + I^- \quad (5)$$

where $H_2O_2$ is hydrogen peroxide, $I^+$ is an iodide ion, $H_2O$ is water, $IO^-$ is a hypoiodite ion, and $O_2$ is oxygen gas.

As noted above, a specific amount of pressurized fluid can be created during the chemical reaction, the pressurized fluid being directed to individual gel reservoirs to facilitate release of conductive gel stored therein. For example, the pressurized fluid can be configured to fill an internal volume of 10 cm$^3$ to a pressure of approximately 50 psi (e.g., a 35 psi pressure to facilitate release of the conductive gel from the gel reservoirs plus a 15 psi safety buffer to account for any unreacted chemicals or other potential complications during the chemical reaction). In the above example chemical reaction, the resulting pressurized fluid is oxygen gas, which has a molar mass of 32.00 g/mol at room temperature (e.g., approximately 295K). As such, based upon the desired pressure (50 psi at standard atmospheric pressure), the internal volume (25 cm$^3$), and the molar mass of the carbon dioxide, an amount of carbon dioxide to be produced during the chemical reaction can be calculated using the ideal gas law.

Substituting the values as noted above into the ideal gas law, the resulting equation is:

$$(50 \text{ psi at } 1 \text{ atm})(25 \text{ cm}^3) = (\text{mass of } O_2/32.00 \text{ g/mol})(8.31441 \text{ J K}^{-1} \text{ mol}^{-1})(295K).$$

Converting both pressure and volume to appropriate units (Pascal and cubic meters respectively) results in:

$$(344737 \text{ pa})(0.000025 \text{ m}^3) = (\text{mass of } O_2/32.00 \text{ g/mol})(8.31441 \text{ J K}^{-1} \text{ mol}^{-1})(295K).$$

Solving the above equation gives a mass of 0.11 g of $O_2$ to be produced. Such a mass of $O_2$ will result in the desired 50 psi in the internal volume of 25 cm$^3$. $O_2$ has a density of 1.43 g/L in its gaseous state. As such, the above equation results in 0.077 liters of $O_2$. Thus, a chemical reaction that produces 0.077 liters of $O_2$ will result in a 50 psi pressure in the internal volume of 25 cm$^3$.

The amount of hydrogen peroxide and potassium iodide to include can be determined based upon the resulting amount of $O_2$ produced. As noted above, 0.11 g of $O_2$ produces a pressure that will result in release of the conductive gel from the conductive gel reservoirs as described above. As noted above, $O_2$ has a molar mass of 32.00 g/mol. As such, 0.11 g equals approximate 0.0046 moles of $O_2$. As such, approximately 0.0046 moles of both potassium iodide and hydrogen peroxide should be included in the reaction. Hydrogen peroxide has a molar mass of 34.015 g/mol. As such, approximately 0.0046 moles of hydrogen peroxide is 0.16 grams. Potassium iodide has a molar mass of 166.00 g/mol. As such, approximately 0.0046 moles of potassium iodide is 0.76 grams. As such, to produce 0.11 grams of $O_2$, at least 0.16 grams of hydrogen peroxide should fully react with 0.76 grams of potassium iodide.

Thus, in certain implementations of the pressure sources 300 and 400 as described above, approximately 0.76 grams of potassium iodide (e.g., in a powdered form) can be used for the first chemical, and approximately 0.16 grams of hydrogen peroxide can be used for the second chemical. Thus, in a particular example referring to pressure source 300 as shown in FIG. 3, approximately 0.76 grams of powdered potassium iodide can be loaded into the case 302. Similarly, approximately 0.16 grams of hydrogen peroxide can be loaded into isolating container 310.

See Table 2 for calculations showing the amounts of oxygen gas or nitrogen gas needed for resulting pressures ranging from 1 psi to 100 psi for a volume of 25 cm$^3$. The reactant amounts can then be calculated using the values of nitrogen gas or oxygen gas needed from Table 2 in a manner similar to the calculations in Table 1.

Tables 3-22 show amounts of carbon dioxide, nitrogen, and oxygen gas needed for volumes ranging from 5 cm$^3$ to 100 cm$^3$.

It will be understood that the implementations obtained from scaling up or scaling down (i.e., changing pressure, volume, or temperature) the implementations exemplified in the Tables attached hereto (but not shown in the Tables) are included in this disclosure.

When the controller, e.g., medical device controller 120, triggers a release of the conductive gel, the wire 312 can be heated, thereby causing a structural compromise of the isolating container 310 (e.g., the wire 312 melts a hole in isolating container 310). The hydrogen peroxide can then be released from the isolating container 310. In certain implementations, leaf springs 314 can provide an external force against the isolating container 310, causing quicker release of the hydrogen peroxide. The hydrogen peroxide can then mix with the potassium iodide in the case 302, causing catalytic decomposition of the hydrogen peroxide into water and oxygen gas. The oxygen gas can be directed out of the case 302 via the exit port 304. The oxygen gas can then be directed by one or more fluid conduits, such as fluid channel 230, to the gel reservoirs.

As described above, the speed of the reaction can be a critical consideration. In order to adjust the reaction speed, the amounts of hydrogen peroxide and potassium iodide can be increased. In certain implementations, a pressure source can include between 0.20 grams and 2.5 grams of hydrogen peroxide. Similarly, a pressure source can include between 0.80 grams and 5.0 grams of potassium iodide. In a particular example, a pressure source can include 0.5 grams of hydrogen peroxide and 1.50 grams of potassium iodide.

TABLE 1

| Pressure (psi) | Pressure (pa) | Volume (cm3) | Volume (m3) | R (ideal gas constant – J/K · mol) | T (Kelvin) | n (number of moles of gas) = (pV)/(RT) | MW of CO2 (g/mol) | Amount of CO2 (g) | Moles of Acetic Acid (mol) | Amount of Acetic Acid (g) | Moles of sodim bicarbonate (mol) | Amount of sodium bicarbonate (g) |
|---|---|---|---|---|---|---|---|---|---|---|---|---|
| 1 | 6894.76 | 25 | 0.000025 | 8.3144598 | 295 | 0.00007028 | 44.0095 | 0.003093 | 0.00007028 | 0.004217 | 0.00007028 | 0.005903128 |
| 5 | 34473.79 | 25 | 0.000025 | 8.3144598 | 295 | 0.00035138 | 44.0095 | 0.015464 | 0.00035138 | 0.021083 | 0.00035138 | 0.029515642 |
| 10 | 68947.57 | 25 | 0.000025 | 8.3144598 | 295 | 0.00070275 | 44.0095 | 0.030928 | 0.00070275 | 0.042165 | 0.00070275 | 0.059031283 |
| 15 | 103421.36 | 25 | 0.000025 | 8.3144598 | 295 | 0.00105413 | 44.0095 | 0.046392 | 0.00105413 | 0.063248 | 0.00105413 | 0.088546925 |
| 20 | 137895.15 | 25 | 0.000025 | 8.3144598 | 295 | 0.00140551 | 44.0095 | 0.061856 | 0.00140551 | 0.08433 | 0.00140551 | 0.118062566 |
| 25 | 172368.93 | 25 | 0.000025 | 8.3144598 | 295 | 0.00175688 | 44.0095 | 0.07732 | 0.00175688 | 0.105413 | 0.00175688 | 0.147578208 |
| 30 | 206842.72 | 25 | 0.000025 | 8.3144598 | 295 | 0.00210826 | 44.0095 | 0.092783 | 0.00210826 | 0.126496 | 0.00210826 | 0.177093849 |
| 35 | 241316.50 | 25 | 0.000025 | 8.3144598 | 295 | 0.00245964 | 44.0095 | 0.108247 | 0.00245964 | 0.147578 | 0.00245964 | 0.206609491 |
| 40 | 275790.29 | 25 | 0.000025 | 8.3144598 | 295 | 0.00281101 | 44.0095 | 0.123711 | 0.00281101 | 0.168661 | 0.00281101 | 0.236125132 |
| 45 | 310264.08 | 25 | 0.000025 | 8.3144598 | 295 | 0.00316239 | 44.0095 | 0.139175 | 0.00316239 | 0.189743 | 0.00316239 | 0.265640774 |
| 50 | 344737.86 | 25 | 0.000025 | 8.3144598 | 295 | 0.00351377 | 44.0095 | 0.154639 | 0.00351377 | 0.210826 | 0.00351377 | 0.295156415 |
| 55 | 379211.65 | 25 | 0.000025 | 8.3144598 | 295 | 0.00386514 | 44.0095 | 0.170103 | 0.00386514 | 0.231909 | 0.00386514 | 0.324672057 |
| 60 | 413685.44 | 25 | 0.000025 | 8.3144598 | 295 | 0.00421652 | 44.0095 | 0.185567 | 0.00421652 | 0.252991 | 0.00421652 | 0.354187698 |
| 65 | 448159.22 | 25 | 0.000025 | 8.3144598 | 295 | 0.00456790 | 44.0095 | 0.201031 | 0.00456790 | 0.274074 | 0.00456790 | 0.38370334 |
| 70 | 482633.01 | 25 | 0.000025 | 8.3144598 | 295 | 0.00491927 | 44.0095 | 0.216495 | 0.00491927 | 0.295156 | 0.00491927 | 0.413218982 |
| 75 | 517106.80 | 25 | 0.000025 | 8.3144598 | 295 | 0.00527065 | 44.0095 | 0.231959 | 0.00491927 | 0.295156 | 0.00491927 | 0.413218982 |
| 80 | 551580.58 | 25 | 0.000025 | 8.3144598 | 295 | 0.00562203 | 44.0095 | 0.247423 | 0.00491927 | 0.295156 | 0.00491927 | 0.413218982 |
| 85 | 586054.37 | 25 | 0.000025 | 8.3144598 | 295 | 0.00597340 | 44.0095 | 0.262887 | 0.00491927 | 0.295156 | 0.00491927 | 0.413218982 |
| 90 | 620528.16 | 25 | 0.000025 | 8.3144598 | 295 | 0.00632478 | 44.0095 | 0.27835 | 0.00491927 | 0.295156 | 0.00491927 | 0.413218982 |
| 95 | 655001.94 | 25 | 0.000025 | 8.3144598 | 295 | 0.00667616 | 44.0095 | 0.293814 | 0.00491927 | 0.295156 | 0.00491927 | 0.413218982 |
| 100 | 689475.73 | 25 | 0.000025 | 8.3144598 | 295 | 0.00702753 | 44.0095 | 0.309278 | 0.00491927 | 0.295156 | 0.00491927 | 0.413218982 |

TABLE 2

| Pressure (psi) | Pressure (pa) | Volume (cm3) | Volume (m3) | R (ideal gas constant – J/K · mol) | T (Kelvin) | n (number of moles of gas) = (pV)/(RT) | MW of N2 (g/mol) | Amount of N2 (g) | MW of O2 (g/mol) | Amount of O2 (g) |
|---|---|---|---|---|---|---|---|---|---|---|
| 1 | 6894.76 | 25 | 0.000025 | 8.3144598 | 295 | 0.00007028 | 28 | 0.00196771 | 32 | 0.0022488 |
| 5 | 34473.79 | 25 | 0.000025 | 8.3144598 | 295 | 0.00035138 | 28 | 0.00983855 | 32 | 0.0112441 |
| 10 | 68947.57 | 25 | 0.000025 | 8.3144598 | 295 | 0.00070275 | 28 | 0.01967709 | 32 | 0.0224881 |
| 15 | 103421.36 | 25 | 0.000025 | 8.3144598 | 295 | 0.00105413 | 28 | 0.02951564 | 32 | 0.0337322 |
| 20 | 137895.15 | 25 | 0.000025 | 8.3144598 | 295 | 0.00140551 | 28 | 0.03935419 | 32 | 0.0449762 |
| 25 | 172368.93 | 25 | 0.000025 | 8.3144598 | 295 | 0.00175688 | 28 | 0.04919274 | 32 | 0.0562203 |
| 30 | 206842.72 | 25 | 0.000025 | 8.3144598 | 295 | 0.00210826 | 28 | 0.05903128 | 32 | 0.0674643 |
| 35 | 241316.50 | 25 | 0.000025 | 8.3144598 | 295 | 0.00245964 | 28 | 0.06886983 | 32 | 0.0787084 |
| 40 | 275790.29 | 25 | 0.000025 | 8.3144598 | 295 | 0.00281101 | 28 | 0.07870838 | 32 | 0.0899524 |
| 45 | 310264.08 | 25 | 0.000025 | 8.3144598 | 295 | 0.00316239 | 28 | 0.08854692 | 32 | 0.1011965 |
| 50 | 344737.86 | 25 | 0.000025 | 8.3144598 | 295 | 0.00351377 | 28 | 0.09838547 | 32 | 0.1124405 |
| 55 | 379211.65 | 25 | 0.000025 | 8.3144598 | 295 | 0.00386514 | 28 | 0.10822402 | 32 | 0.1236846 |
| 60 | 413685.44 | 25 | 0.000025 | 8.3144598 | 295 | 0.00421652 | 28 | 0.11806257 | 32 | 0.1349286 |
| 65 | 448159.22 | 25 | 0.000025 | 8.3144598 | 295 | 0.00456790 | 28 | 0.12790111 | 32 | 0.1461727 |

TABLE 2-continued

| Pressure (psi) | Pressure (pa) | Volume (cm3) | Volume (m3) | R (ideal gas constant – J/K · mol) | T (Kelvin) | n (number of moles of gas) = (pV)/(RT) | MW of N2 (g/mol) | Amount of N2 (g) | MW of O2 (g/mol) | Amount of O2 (g) |
|---|---|---|---|---|---|---|---|---|---|---|
| 70 | 482633.01 | 25 | 0.000025 | 8.3144598 | 295 | 0.00491927 | 28 | 0.13773966 | 32 | 0.1574168 |
| 75 | 517106.80 | 25 | 0.000025 | 8.3144598 | 295 | 0.00527065 | 28 | 0.14757821 | 32 | 0.1686608 |
| 80 | 551580.58 | 25 | 0.000025 | 8.3144598 | 295 | 0.00562203 | 28 | 0.15741675 | 32 | 0.1799049 |
| 85 | 586054.37 | 25 | 0.000025 | 8.3144598 | 295 | 0.00597340 | 28 | 0.1672553 | 32 | 0.1911489 |
| 90 | 620528.16 | 25 | 0.000025 | 8.3144598 | 295 | 0.00632478 | 28 | 0.17709385 | 32 | 0.202393 |
| 95 | 655001.94 | 25 | 0.000025 | 8.3144598 | 295 | 0.00667616 | 28 | 0.1869324 | 32 | 0.213637 |
| 100 | 689475.73 | 25 | 0.000025 | 8.3144598 | 295 | 0.00702753 | 28 | 0.19677094 | 32 | 0.2248811 |

TABLE 3

| Pressure (psi) | Pressure (pa) | Volume (cm3) | Volume (m3) | R (ideal gas constant – J/K · mol) | T (Kelvin) | n (number of moles of gas) = (pV)/(RT) | MW of CO2 (g/mol) | Amount of CO2 (g) | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 5 | 0.000005 | 8.3144598 | 295 | 0.00007028 | 44.0095 | 0.003093 | 28 | 0.001968 | 32 | 0.002249 |
| 10 | 68947.57 | 5 | 0.000005 | 8.3144598 | 295 | 0.00014055 | 44.0095 | 0.006186 | 28 | 0.003935 | 32 | 0.004498 |
| 15 | 103421.36 | 5 | 0.000005 | 8.3144598 | 295 | 0.00021083 | 44.0095 | 0.009278 | 28 | 0.005903 | 32 | 0.006746 |
| 20 | 137895.15 | 5 | 0.000005 | 8.3144598 | 295 | 0.00028110 | 44.0095 | 0.012371 | 28 | 0.007871 | 32 | 0.008995 |
| 25 | 172368.93 | 5 | 0.000005 | 8.3144598 | 295 | 0.00035138 | 44.0095 | 0.015464 | 28 | 0.009839 | 32 | 0.011244 |
| 30 | 206842.72 | 5 | 0.000005 | 8.3144598 | 295 | 0.00042165 | 44.0095 | 0.018557 | 28 | 0.011806 | 32 | 0.013493 |
| 35 | 241316.50 | 5 | 0.000005 | 8.3144598 | 295 | 0.00049193 | 44.0095 | 0.021649 | 28 | 0.013774 | 32 | 0.015742 |
| 40 | 275790.29 | 5 | 0.000005 | 8.3144598 | 295 | 0.00056220 | 44.0095 | 0.024742 | 28 | 0.015742 | 32 | 0.01799 |
| 45 | 310264.08 | 5 | 0.000005 | 8.3144598 | 295 | 0.00063248 | 44.0095 | 0.027835 | 28 | 0.017709 | 32 | 0.020239 |
| 50 | 344737.86 | 5 | 0.000005 | 8.3144598 | 295 | 0.00070275 | 44.0095 | 0.030928 | 28 | 0.019677 | 32 | 0.022488 |
| 55 | 379211.65 | 5 | 0.000005 | 8.3144598 | 295 | 0.00077303 | 44.0095 | 0.034021 | 28 | 0.021645 | 32 | 0.024737 |
| 60 | 413685.44 | 5 | 0.000005 | 8.3144598 | 295 | 0.00084330 | 44.0095 | 0.037113 | 28 | 0.023613 | 32 | 0.026986 |
| 65 | 448159.22 | 5 | 0.000005 | 8.3144598 | 295 | 0.00091358 | 44.0095 | 0.040206 | 28 | 0.02558 | 32 | 0.029235 |
| 70 | 482633.01 | 5 | 0.000005 | 8.3144598 | 295 | 0.00098385 | 44.0095 | 0.043299 | 28 | 0.027548 | 32 | 0.031483 |
| 75 | 517106.80 | 5 | 0.000005 | 8.3144598 | 295 | 0.00105413 | 44.0095 | 0.046392 | 28 | 0.029516 | 32 | 0.033732 |

TABLE 4

| Pressure (psi) | Pressure (pa) | Volume (cm3) | Volume (m3) | R (ideal gas constant – J/K · mol) | T (Kelvin) | n (number of moles of gas) = (pV)/(RT) | MW of CO2 (g/mol) | Amount of CO2 (g) | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 10 | 0.00001 | 8.3144598 | 295 | 0.00014055 | 44.0095 | 0.006186 | 28 | 0.003935 | 32 | 0.004498 |
| 10 | 68947.57 | 10 | 0.00001 | 8.3144598 | 295 | 0.00028110 | 44.0095 | 0.012371 | 28 | 0.007871 | 32 | 0.008995 |
| 15 | 103421.36 | 10 | 0.00001 | 8.3144598 | 295 | 0.00042165 | 44.0095 | 0.018557 | 28 | 0.011806 | 32 | 0.013493 |
| 20 | 137895.15 | 10 | 0.00001 | 8.3144598 | 295 | 0.00056220 | 44.0095 | 0.024742 | 28 | 0.015742 | 32 | 0.01799 |
| 25 | 172368.93 | 10 | 0.00001 | 8.3144598 | 295 | 0.00070275 | 44.0095 | 0.030928 | 28 | 0.019677 | 32 | 0.022488 |
| 30 | 206842.72 | 10 | 0.00001 | 8.3144598 | 295 | 0.00084330 | 44.0095 | 0.037113 | 28 | 0.023613 | 32 | 0.026986 |
| 35 | 241316.50 | 10 | 0.00001 | 8.3144598 | 295 | 0.00098385 | 44.0095 | 0.043299 | 28 | 0.027548 | 32 | 0.031483 |
| 40 | 275790.29 | 10 | 0.00001 | 8.3144598 | 295 | 0.00112441 | 44.0095 | 0.049485 | 28 | 0.031483 | 32 | 0.035981 |
| 45 | 310264.08 | 10 | 0.00001 | 8.3144598 | 295 | 0.00126496 | 44.0095 | 0.05567 | 28 | 0.035419 | 32 | 0.040479 |
| 50 | 344737.86 | 10 | 0.00001 | 8.3144598 | 295 | 0.00140551 | 44.0095 | 0.061856 | 28 | 0.039354 | 32 | 0.044976 |
| 55 | 379211.65 | 10 | 0.00001 | 8.3144598 | 295 | 0.00154606 | 44.0095 | 0.068041 | 28 | 0.04329 | 32 | 0.049474 |
| 60 | 413685.44 | 10 | 0.00001 | 8.3144598 | 295 | 0.00168661 | 44.0095 | 0.074227 | 28 | 0.047225 | 32 | 0.053971 |
| 65 | 448159.22 | 10 | 0.00001 | 8.3144598 | 295 | 0.00182716 | 44.0095 | 0.080412 | 28 | 0.05116 | 32 | 0.058469 |
| 70 | 482633.01 | 10 | 0.00001 | 8.3144598 | 295 | 0.00196771 | 44.0095 | 0.086598 | 28 | 0.055096 | 32 | 0.062967 |
| 75 | 517106.80 | 10 | 0.00001 | 8.3144598 | 295 | 0.00210826 | 44.0095 | 0.092783 | 28 | 0.059031 | 32 | 0.067464 |

TABLE 5

| Pressure (psi) | Pressure (pa) | Volume (cm3) | Volume (m3) | R (ideal gas constant – J/K · mol) | T (Kelvin) | n (number of moles of gas) = (pV)/(RT) | MW of CO2 (g/mol) | Amount of CO2 (g) | MW of N2 (g/mol) | Amount of N2 (g) | MW of O2 (g/mol) | Amount of O2 (g) |
|---|---|---|---|---|---|---|---|---|---|---|---|---|
| 5  | 34473.79  | 15 | 0.000015 | 8.3144598 | 295 | 0.00021083 | 44.0095 | 0.009278 | 28 | 0.005903 | 32 | 0.006746 |
| 10 | 68947.57  | 15 | 0.000015 | 8.3144598 | 295 | 0.00042165 | 44.0095 | 0.018557 | 28 | 0.011806 | 32 | 0.013493 |
| 15 | 103421.36 | 15 | 0.000015 | 8.3144598 | 295 | 0.00063248 | 44.0095 | 0.027835 | 28 | 0.017709 | 32 | 0.020239 |
| 20 | 137895.15 | 15 | 0.000015 | 8.3144598 | 295 | 0.00084330 | 44.0095 | 0.037113 | 28 | 0.023613 | 32 | 0.026986 |
| 25 | 172368.93 | 15 | 0.000015 | 8.3144598 | 295 | 0.00105413 | 44.0095 | 0.046392 | 28 | 0.029516 | 32 | 0.033732 |
| 30 | 206842.72 | 15 | 0.000015 | 8.3144598 | 295 | 0.00126496 | 44.0095 | 0.05567  | 28 | 0.035419 | 32 | 0.040479 |
| 35 | 241316.50 | 15 | 0.000015 | 8.3144598 | 295 | 0.00147578 | 44.0095 | 0.064948 | 28 | 0.041322 | 32 | 0.047225 |
| 40 | 275790.29 | 15 | 0.000015 | 8.3144598 | 295 | 0.00168661 | 44.0095 | 0.074227 | 28 | 0.047225 | 32 | 0.053971 |
| 45 | 310264.08 | 15 | 0.000015 | 8.3144598 | 295 | 0.00189743 | 44.0095 | 0.083505 | 28 | 0.053128 | 32 | 0.060718 |
| 50 | 344737.86 | 15 | 0.000015 | 8.3144598 | 295 | 0.00210826 | 44.0095 | 0.092783 | 28 | 0.059031 | 32 | 0.067464 |
| 55 | 379211.65 | 15 | 0.000015 | 8.3144598 | 295 | 0.00231909 | 44.0095 | 0.102062 | 28 | 0.064934 | 32 | 0.074211 |
| 60 | 413685.44 | 15 | 0.000015 | 8.3144598 | 295 | 0.00252991 | 44.0095 | 0.11134  | 28 | 0.070838 | 32 | 0.080957 |
| 65 | 448159.22 | 15 | 0.000015 | 8.3144598 | 295 | 0.00274074 | 44.0095 | 0.120619 | 28 | 0.076741 | 32 | 0.087704 |
| 70 | 482633.01 | 15 | 0.000015 | 8.3144598 | 295 | 0.00295156 | 44.0095 | 0.129897 | 28 | 0.082644 | 32 | 0.09445  |
| 75 | 517106.80 | 15 | 0.000015 | 8.3144598 | 295 | 0.00316239 | 44.0095 | 0.139175 | 28 | 0.088547 | 32 | 0.101196 |

TABLE 6

| Pressure (psi) | Pressure (pa) | Volume (cm3) | Volume (m3) | R (ideal gas constant – J/K · mol) | T (Kelvin) | n (number of moles of gas) = (pV)/(RT) | MW of CO2 (g/mol) | Amount of CO2 (g) | MW of N2 (g/mol) | Amount of N2 (g) | MW of O2 (g/mol) | Amount of O2 (g) |
|---|---|---|---|---|---|---|---|---|---|---|---|---|
| 5  | 34473.79  | 20 | 0.00002 | 8.3144598 | 295 | 0.00028110 | 44.0095 | 0.012371 | 28 | 0.007871 | 32 | 0.008995 |
| 10 | 68947.57  | 20 | 0.00002 | 8.3144598 | 295 | 0.00056220 | 44.0095 | 0.024742 | 28 | 0.015742 | 32 | 0.01799  |
| 15 | 103421.36 | 20 | 0.00002 | 8.3144598 | 295 | 0.00084330 | 44.0095 | 0.037113 | 28 | 0.023613 | 32 | 0.026986 |
| 20 | 137895.15 | 20 | 0.00002 | 8.3144598 | 295 | 0.00112441 | 44.0095 | 0.049485 | 28 | 0.031483 | 32 | 0.035981 |
| 25 | 172368.93 | 20 | 0.00002 | 8.3144598 | 295 | 0.00140551 | 44.0095 | 0.061856 | 28 | 0.039354 | 32 | 0.044976 |
| 30 | 206842.72 | 20 | 0.00002 | 8.3144598 | 295 | 0.00168661 | 44.0095 | 0.074227 | 28 | 0.047225 | 32 | 0.053971 |
| 35 | 241316.50 | 20 | 0.00002 | 8.3144598 | 295 | 0.00196771 | 44.0095 | 0.086598 | 28 | 0.055096 | 32 | 0.062967 |
| 40 | 275790.29 | 20 | 0.00002 | 8.3144598 | 295 | 0.00224881 | 44.0095 | 0.098969 | 28 | 0.062967 | 32 | 0.071962 |
| 45 | 310264.08 | 20 | 0.00002 | 8.3144598 | 295 | 0.00252991 | 44.0095 | 0.11134  | 28 | 0.070838 | 32 | 0.080957 |
| 50 | 344737.86 | 20 | 0.00002 | 8.3144598 | 295 | 0.00281101 | 44.0095 | 0.123711 | 28 | 0.078708 | 32 | 0.089952 |
| 55 | 379211.65 | 20 | 0.00002 | 8.3144598 | 295 | 0.00309211 | 44.0095 | 0.136082 | 28 | 0.086579 | 32 | 0.098948 |
| 60 | 413685.44 | 20 | 0.00002 | 8.3144598 | 295 | 0.00337322 | 44.0095 | 0.148454 | 28 | 0.09445  | 32 | 0.107943 |
| 65 | 448159.22 | 20 | 0.00002 | 8.3144598 | 295 | 0.00365432 | 44.0095 | 0.160825 | 28 | 0.102321 | 32 | 0.116938 |
| 70 | 482633.01 | 20 | 0.00002 | 8.3144598 | 295 | 0.00393542 | 44.0095 | 0.173196 | 28 | 0.110192 | 32 | 0.125933 |
| 75 | 517106.80 | 20 | 0.00002 | 8.3144598 | 295 | 0.00421652 | 44.0095 | 0.185567 | 28 | 0.118063 | 32 | 0.134929 |

TABLE 7

| Pressure (psi) | Pressure (pa) | Volume (cm3) | Volume (m3) | R (ideal gas constant – J/K · mol) | T (Kelvin) | n (number of moles of gas) = (pV)/(RT) | MW of CO2 (g/mol) | Amount of CO2 (g) | MW of N2 (g/mol) | Amount of N2 (g) | MW of O2 (g/mol) | Amount of O2 (g) |
|---|---|---|---|---|---|---|---|---|---|---|---|---|
| 5  | 34473.79  | 25 | 0.000025 | 8.3144598 | 295 | 0.00035138 | 44.0095 | 0.015464 | 28 | 0.009839 | 32 | 0.011244 |
| 10 | 68947.57  | 25 | 0.000025 | 8.3144598 | 295 | 0.00070275 | 44.0095 | 0.030928 | 28 | 0.019677 | 32 | 0.022488 |
| 15 | 103421.36 | 25 | 0.000025 | 8.3144598 | 295 | 0.00105413 | 44.0095 | 0.046392 | 28 | 0.029516 | 32 | 0.033732 |
| 20 | 137895.15 | 25 | 0.000025 | 8.3144598 | 295 | 0.00140551 | 44.0095 | 0.061856 | 28 | 0.039354 | 32 | 0.044976 |
| 25 | 172368.93 | 25 | 0.000025 | 8.3144598 | 295 | 0.00175688 | 44.0095 | 0.07732  | 28 | 0.049193 | 32 | 0.05622  |
| 30 | 206842.72 | 25 | 0.000025 | 8.3144598 | 295 | 0.00210826 | 44.0095 | 0.092783 | 28 | 0.059031 | 32 | 0.067464 |
| 35 | 241316.50 | 25 | 0.000025 | 8.3144598 | 295 | 0.00245964 | 44.0095 | 0.108247 | 28 | 0.06887  | 32 | 0.078708 |
| 40 | 275790.29 | 25 | 0.000025 | 8.3144598 | 295 | 0.00281101 | 44.0095 | 0.123711 | 28 | 0.078708 | 32 | 0.089952 |
| 45 | 310264.08 | 25 | 0.000025 | 8.3144598 | 295 | 0.00316239 | 44.0095 | 0.139175 | 28 | 0.088547 | 32 | 0.101196 |
| 50 | 344737.86 | 25 | 0.000025 | 8.3144598 | 295 | 0.00351377 | 44.0095 | 0.154639 | 28 | 0.098385 | 32 | 0.112441 |
| 55 | 379211.65 | 25 | 0.000025 | 8.3144598 | 295 | 0.00386514 | 44.0095 | 0.170103 | 28 | 0.108224 | 32 | 0.123685 |
| 60 | 413685.44 | 25 | 0.000025 | 8.3144598 | 295 | 0.00421652 | 44.0095 | 0.185567 | 28 | 0.118063 | 32 | 0.134929 |
| 65 | 448159.22 | 25 | 0.000025 | 8.3144598 | 295 | 0.00456790 | 44.0095 | 0.201031 | 28 | 0.127901 | 32 | 0.146173 |
| 70 | 482633.01 | 25 | 0.000025 | 8.3144598 | 295 | 0.00491927 | 44.0095 | 0.216495 | 28 | 0.13774  | 32 | 0.157417 |
| 75 | 517106.80 | 25 | 0.000025 | 8.3144598 | 295 | 0.00527065 | 44.0095 | 0.231959 | 28 | 0.147578 | 32 | 0.168661 |

TABLE 8

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 30 | 0.00003 | 8.3144598 | 295 | 0.00042165 | 44.0095 | 0.018557 | 28 | 0.011806 | 32 | 0.013493 |
| 10 | 68947.57 | 30 | 0.00003 | 8.3144598 | 295 | 0.00084330 | 44.0095 | 0.037113 | 28 | 0.023613 | 32 | 0.026986 |
| 15 | 103421.36 | 30 | 0.00003 | 8.3144598 | 295 | 0.00126496 | 44.0095 | 0.05567 | 28 | 0.035419 | 32 | 0.040479 |
| 20 | 137895.15 | 30 | 0.00003 | 8.3144598 | 295 | 0.00168661 | 44.0095 | 0.074227 | 28 | 0.047225 | 32 | 0.053971 |
| 25 | 172368.93 | 30 | 0.00003 | 8.3144598 | 295 | 0.00210826 | 44.0095 | 0.092783 | 28 | 0.059031 | 32 | 0.067464 |
| 30 | 206842.72 | 30 | 0.00003 | 8.3144598 | 295 | 0.00252991 | 44.0095 | 0.11134 | 28 | 0.070838 | 32 | 0.080957 |
| 35 | 241316.50 | 30 | 0.00003 | 8.3144598 | 295 | 0.00295156 | 44.0095 | 0.129897 | 28 | 0.082644 | 32 | 0.09445 |
| 40 | 275790.29 | 30 | 0.00003 | 8.3144598 | 295 | 0.00337322 | 44.0095 | 0.148454 | 28 | 0.09445 | 32 | 0.107943 |
| 45 | 310264.08 | 30 | 0.00003 | 8.3144598 | 295 | 0.00379487 | 44.0095 | 0.16701 | 28 | 0.106256 | 32 | 0.121436 |
| 50 | 344737.86 | 30 | 0.00003 | 8.3144598 | 295 | 0.00421652 | 44.0095 | 0.185567 | 28 | 0.118063 | 32 | 0.134929 |
| 55 | 379211.65 | 30 | 0.00003 | 8.3144598 | 295 | 0.00463817 | 44.0095 | 0.204124 | 28 | 0.129869 | 32 | 0.148422 |
| 60 | 413685.44 | 30 | 0.00003 | 8.3144598 | 295 | 0.00505982 | 44.0095 | 0.22268 | 28 | 0.141675 | 32 | 0.161914 |
| 65 | 448159.22 | 30 | 0.00003 | 8.3144598 | 295 | 0.00548148 | 44.0095 | 0.241237 | 28 | 0.153481 | 32 | 0.175407 |
| 70 | 482633.01 | 30 | 0.00003 | 8.3144598 | 295 | 0.00590313 | 44.0095 | 0.259794 | 28 | 0.165288 | 32 | 0.1889 |
| 75 | 517106.80 | 30 | 0.00003 | 8.3144598 | 295 | 0.00632478 | 44.0095 | 0.27835 | 28 | 0.177094 | 32 | 0.202393 |

TABLE 9

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 35 | 0.000035 | 8.3144598 | 295 | 0.00049193 | 44.0095 | 0.021649 | 28 | 0.013774 | 32 | 0.015742 |
| 10 | 68947.57 | 35 | 0.000035 | 8.3144598 | 295 | 0.00098385 | 44.0095 | 0.043299 | 28 | 0.027548 | 32 | 0.031483 |
| 15 | 103421.36 | 35 | 0.000035 | 8.3144598 | 295 | 0.00147578 | 44.0095 | 0.064948 | 28 | 0.041322 | 32 | 0.047225 |
| 20 | 137895.15 | 35 | 0.000035 | 8.3144598 | 295 | 0.00196771 | 44.0095 | 0.086598 | 28 | 0.055096 | 32 | 0.062967 |
| 25 | 172368.93 | 35 | 0.000035 | 8.3144598 | 295 | 0.00245964 | 44.0095 | 0.108247 | 28 | 0.06887 | 32 | 0.078708 |
| 30 | 206842.72 | 35 | 0.000035 | 8.3144598 | 295 | 0.00295156 | 44.0095 | 0.129897 | 28 | 0.082644 | 32 | 0.09445 |
| 35 | 241316.50 | 35 | 0.000035 | 8.3144598 | 295 | 0.00344349 | 44.0095 | 0.151546 | 28 | 0.096418 | 32 | 0.110192 |
| 40 | 275790.29 | 35 | 0.000035 | 8.3144598 | 295 | 0.00393542 | 44.0095 | 0.173196 | 28 | 0.110192 | 32 | 0.125933 |
| 45 | 310264.08 | 35 | 0.000035 | 8.3144598 | 295 | 0.00442735 | 44.0095 | 0.194845 | 28 | 0.123966 | 32 | 0.141675 |
| 50 | 344737.86 | 35 | 0.000035 | 8.3144598 | 295 | 0.00491927 | 44.0095 | 0.216495 | 28 | 0.13774 | 32 | 0.157417 |
| 55 | 379211.65 | 35 | 0.000035 | 8.3144598 | 295 | 0.00541120 | 44.0095 | 0.238144 | 28 | 0.151514 | 32 | 0.173158 |
| 60 | 413685.44 | 35 | 0.000035 | 8.3144598 | 295 | 0.00590313 | 44.0095 | 0.259794 | 28 | 0.165288 | 32 | 0.1889 |
| 65 | 448159.22 | 35 | 0.000035 | 8.3144598 | 295 | 0.00639506 | 44.0095 | 0.281443 | 28 | 0.179062 | 32 | 0.204642 |
| 70 | 482633.01 | 35 | 0.000035 | 8.3144598 | 295 | 0.00688698 | 44.0095 | 0.303093 | 28 | 0.192836 | 32 | 0.220383 |
| 75 | 517106.80 | 35 | 0.000035 | 8.3144598 | 295 | 0.00737891 | 44.0095 | 0.324742 | 28 | 0.206609 | 32 | 0.236125 |

TABLE 10

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 40 | 0.00004 | 8.3144598 | 295 | 0.00056220 | 44.0095 | 0.024742 | 28 | 0.015742 | 32 | 0.01799 |
| 10 | 68947.57 | 40 | 0.00004 | 8.3144598 | 295 | 0.00112441 | 44.0095 | 0.049485 | 28 | 0.031483 | 32 | 0.035981 |
| 15 | 103421.36 | 40 | 0.00004 | 8.3144598 | 295 | 0.00168661 | 44.0095 | 0.074227 | 28 | 0.047225 | 32 | 0.053971 |
| 20 | 137895.15 | 40 | 0.00004 | 8.3144598 | 295 | 0.00224881 | 44.0095 | 0.098969 | 28 | 0.062967 | 32 | 0.071962 |
| 25 | 172368.93 | 40 | 0.00004 | 8.3144598 | 295 | 0.00281101 | 44.0095 | 0.123711 | 28 | 0.078708 | 32 | 0.089952 |
| 30 | 206842.72 | 40 | 0.00004 | 8.3144598 | 295 | 0.00337322 | 44.0095 | 0.148454 | 28 | 0.09445 | 32 | 0.107943 |
| 35 | 241316.50 | 40 | 0.00004 | 8.3144598 | 295 | 0.00393542 | 44.0095 | 0.173196 | 28 | 0.110192 | 32 | 0.125933 |
| 40 | 275790.29 | 40 | 0.00004 | 8.3144598 | 295 | 0.00449762 | 44.0095 | 0.197938 | 28 | 0.125933 | 32 | 0.143924 |
| 45 | 310264.08 | 40 | 0.00004 | 8.3144598 | 295 | 0.00505982 | 44.0095 | 0.22268 | 28 | 0.141675 | 32 | 0.161914 |
| 50 | 344737.86 | 40 | 0.00004 | 8.3144598 | 295 | 0.00562203 | 44.0095 | 0.247423 | 28 | 0.157417 | 32 | 0.179905 |
| 55 | 379211.65 | 40 | 0.00004 | 8.3144598 | 295 | 0.00618423 | 44.0095 | 0.272165 | 28 | 0.173158 | 32 | 0.197895 |
| 60 | 413685.44 | 40 | 0.00004 | 8.3144598 | 295 | 0.00674643 | 44.0095 | 0.296907 | 28 | 0.1889 | 32 | 0.215886 |
| 65 | 448159.22 | 40 | 0.00004 | 8.3144598 | 295 | 0.00730864 | 44.0095 | 0.321649 | 28 | 0.204642 | 32 | 0.233876 |
| 70 | 482633.01 | 40 | 0.00004 | 8.3144598 | 295 | 0.00787084 | 44.0095 | 0.346392 | 28 | 0.220383 | 32 | 0.251867 |
| 75 | 517106.80 | 40 | 0.00004 | 8.3144598 | 295 | 0.00843304 | 44.0095 | 0.371134 | 28 | 0.236125 | 32 | 0.269857 |

TABLE 11

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 45 | 0.000045 | 8.3144598 | 295 | 0.00063248 | 44.0095 | 0.027835 | 28 | 0.017709 | 32 | 0.020239 |
| 10 | 68947.57 | 45 | 0.000045 | 8.3144598 | 295 | 0.00126496 | 44.0095 | 0.05567 | 28 | 0.035419 | 32 | 0.040479 |
| 15 | 103421.36 | 45 | 0.000045 | 8.3144598 | 295 | 0.00189743 | 44.0095 | 0.083505 | 28 | 0.053128 | 32 | 0.060718 |
| 20 | 137895.15 | 45 | 0.000045 | 8.3144598 | 295 | 0.00252991 | 44.0095 | 0.11134 | 28 | 0.070838 | 32 | 0.080957 |
| 25 | 172368.93 | 45 | 0.000045 | 8.3144598 | 295 | 0.00316239 | 44.0095 | 0.139175 | 28 | 0.088547 | 32 | 0.101196 |
| 30 | 206842.72 | 45 | 0.000045 | 8.3144598 | 295 | 0.00379487 | 44.0095 | 0.16701 | 28 | 0.106256 | 32 | 0.121436 |
| 35 | 241316.50 | 45 | 0.000045 | 8.3144598 | 295 | 0.00442735 | 44.0095 | 0.194845 | 28 | 0.123966 | 32 | 0.141675 |
| 40 | 275790.29 | 45 | 0.000045 | 8.3144598 | 295 | 0.00505982 | 44.0095 | 0.22268 | 28 | 0.141675 | 32 | 0.161914 |
| 45 | 310264.08 | 45 | 0.000045 | 8.3144598 | 295 | 0.00569230 | 44.0095 | 0.250515 | 28 | 0.159384 | 32 | 0.182154 |
| 50 | 344737.86 | 45 | 0.000045 | 8.3144598 | 295 | 0.00632478 | 44.0095 | 0.27835 | 28 | 0.177094 | 32 | 0.202393 |
| 55 | 379211.65 | 45 | 0.000045 | 8.3144598 | 295 | 0.00695726 | 44.0095 | 0.306185 | 28 | 0.194803 | 32 | 0.222632 |
| 60 | 413685.44 | 45 | 0.000045 | 8.3144598 | 295 | 0.00758974 | 44.0095 | 0.334021 | 28 | 0.212513 | 32 | 0.242872 |
| 65 | 448159.22 | 45 | 0.000045 | 8.3144598 | 295 | 0.00822221 | 44.0095 | 0.361856 | 28 | 0.230222 | 32 | 0.263111 |
| 70 | 482633.01 | 45 | 0.000045 | 8.3144598 | 295 | 0.00885469 | 44.0095 | 0.389691 | 28 | 0.247931 | 32 | 0.28335 |
| 75 | 517106.80 | 45 | 0.000045 | 8.3144598 | 295 | 0.00948717 | 44.0095 | 0.417526 | 28 | 0.265641 | 32 | 0.303589 |

TABLE 12

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 50 | 0.00005 | 8.3144598 | 295 | 0.00070275 | 44.0095 | 0.030928 | 28 | 0.019677 | 32 | 0.022488 |
| 10 | 68947.57 | 50 | 0.00005 | 8.3144598 | 295 | 0.00140551 | 44.0095 | 0.061856 | 28 | 0.039354 | 32 | 0.044976 |
| 15 | 103421.36 | 50 | 0.00005 | 8.3144598 | 295 | 0.00210826 | 44.0095 | 0.092783 | 28 | 0.059031 | 32 | 0.067464 |
| 20 | 137895.15 | 50 | 0.00005 | 8.3144598 | 295 | 0.00281101 | 44.0095 | 0.123711 | 28 | 0.078708 | 32 | 0.089952 |
| 25 | 172368.93 | 50 | 0.00005 | 8.3144598 | 295 | 0.00351377 | 44.0095 | 0.154639 | 28 | 0.098385 | 32 | 0.112441 |
| 30 | 206842.72 | 50 | 0.00005 | 8.3144598 | 295 | 0.00421652 | 44.0095 | 0.185567 | 28 | 0.118063 | 32 | 0.134929 |
| 35 | 241316.50 | 50 | 0.00005 | 8.3144598 | 295 | 0.00491927 | 44.0095 | 0.216495 | 28 | 0.13774 | 32 | 0.157417 |
| 40 | 275790.29 | 50 | 0.00005 | 8.3144598 | 295 | 0.00562203 | 44.0095 | 0.247423 | 28 | 0.157417 | 32 | 0.179905 |
| 45 | 310264.08 | 50 | 0.00005 | 8.3144598 | 295 | 0.00632478 | 44.0095 | 0.27835 | 28 | 0.177094 | 32 | 0.202393 |
| 50 | 344737.86 | 50 | 0.00005 | 8.3144598 | 295 | 0.00702753 | 44.0095 | 0.309278 | 28 | 0.196771 | 32 | 0.224881 |
| 55 | 379211.65 | 50 | 0.00005 | 8.3144598 | 295 | 0.00773029 | 44.0095 | 0.340206 | 28 | 0.216448 | 32 | 0.247369 |
| 60 | 413685.44 | 50 | 0.00005 | 8.3144598 | 295 | 0.00843304 | 44.0095 | 0.371134 | 28 | 0.236125 | 32 | 0.269857 |
| 65 | 448159.22 | 50 | 0.00005 | 8.3144598 | 295 | 0.00913579 | 44.0095 | 0.402062 | 28 | 0.255802 | 32 | 0.292345 |
| 70 | 482633.01 | 50 | 0.00005 | 8.3144598 | 295 | 0.00983855 | 44.0095 | 0.43299 | 28 | 0.275479 | 32 | 0.314834 |
| 75 | 517106.80 | 50 | 0.00005 | 8.3144598 | 295 | 0.01054130 | 44.0095 | 0.463917 | 28 | 0.295156 | 32 | 0.337322 |

TABLE 13

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 55 | 0.000055 | 8.3144598 | 295 | 0.00077303 | 44.0095 | 0.034021 | 28 | 0.021645 | 32 | 0.024737 |
| 10 | 68947.57 | 55 | 0.000055 | 8.3144598 | 295 | 0.00154606 | 44.0095 | 0.068041 | 28 | 0.04329 | 32 | 0.049474 |
| 15 | 103421.36 | 55 | 0.000055 | 8.3144598 | 295 | 0.00231909 | 44.0095 | 0.102062 | 28 | 0.064934 | 32 | 0.074211 |
| 20 | 137895.15 | 55 | 0.000055 | 8.3144598 | 295 | 0.00309211 | 44.0095 | 0.136082 | 28 | 0.086579 | 32 | 0.098948 |
| 25 | 172368.93 | 55 | 0.000055 | 8.3144598 | 295 | 0.00386514 | 44.0095 | 0.170103 | 28 | 0.108224 | 32 | 0.123685 |
| 30 | 206842.72 | 55 | 0.000055 | 8.3144598 | 295 | 0.00463817 | 44.0095 | 0.204124 | 28 | 0.129869 | 32 | 0.148422 |
| 35 | 241316.50 | 55 | 0.000055 | 8.3144598 | 295 | 0.00541120 | 44.0095 | 0.238144 | 28 | 0.151514 | 32 | 0.173158 |
| 40 | 275790.29 | 55 | 0.000055 | 8.3144598 | 295 | 0.00618423 | 44.0095 | 0.272165 | 28 | 0.173158 | 32 | 0.197895 |
| 45 | 310264.08 | 55 | 0.000055 | 8.3144598 | 295 | 0.00695726 | 44.0095 | 0.306185 | 28 | 0.194803 | 32 | 0.222632 |
| 50 | 344737.86 | 55 | 0.000055 | 8.3144598 | 295 | 0.00773029 | 44.0095 | 0.340206 | 28 | 0.216448 | 32 | 0.247369 |
| 55 | 379211.65 | 55 | 0.000055 | 8.3144598 | 295 | 0.00850332 | 44.0095 | 0.374227 | 28 | 0.238093 | 32 | 0.272106 |
| 60 | 413685.44 | 55 | 0.000055 | 8.3144598 | 295 | 0.00927634 | 44.0095 | 0.408247 | 28 | 0.259738 | 32 | 0.296843 |
| 65 | 448159.22 | 55 | 0.000055 | 8.3144598 | 295 | 0.01004937 | 44.0095 | 0.442268 | 28 | 0.281382 | 32 | 0.32158 |
| 70 | 482633.01 | 55 | 0.000055 | 8.3144598 | 295 | 0.01082240 | 44.0095 | 0.476288 | 28 | 0.303027 | 32 | 0.346317 |
| 75 | 517106.80 | 55 | 0.000055 | 8.3144598 | 295 | 0.01159543 | 44.0095 | 0.510309 | 28 | 0.324672 | 32 | 0.371054 |

TABLE 14

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 60 | 0.00006 | 8.3144598 | 295 | 0.00084330 | 44.0095 | 0.037113 | 28 | 0.023613 | 32 | 0.026986 |
| 10 | 68947.57 | 60 | 0.00006 | 8.3144598 | 295 | 0.00168661 | 44.0095 | 0.074227 | 28 | 0.047225 | 32 | 0.053971 |
| 15 | 103421.36 | 60 | 0.00006 | 8.3144598 | 295 | 0.00252991 | 44.0095 | 0.11134 | 28 | 0.070838 | 32 | 0.080957 |
| 20 | 137895.15 | 60 | 0.00006 | 8.3144598 | 295 | 0.00337322 | 44.0095 | 0.148454 | 28 | 0.09445 | 32 | 0.107943 |
| 25 | 172368.93 | 60 | 0.00006 | 8.3144598 | 295 | 0.00421652 | 44.0095 | 0.185567 | 28 | 0.118063 | 32 | 0.134929 |
| 30 | 206842.72 | 60 | 0.00006 | 8.3144598 | 295 | 0.00505982 | 44.0095 | 0.22268 | 28 | 0.141675 | 32 | 0.161914 |
| 35 | 241316.50 | 60 | 0.00006 | 8.3144598 | 295 | 0.00590313 | 44.0095 | 0.259794 | 28 | 0.165288 | 32 | 0.1889 |
| 40 | 275790.29 | 60 | 0.00006 | 8.3144598 | 295 | 0.00674643 | 44.0095 | 0.296907 | 28 | 0.1889 | 32 | 0.215886 |
| 45 | 310264.08 | 60 | 0.00006 | 8.3144598 | 295 | 0.00758974 | 44.0095 | 0.334021 | 28 | 0.212513 | 32 | 0.242872 |
| 50 | 344737.86 | 60 | 0.00006 | 8.3144598 | 295 | 0.00843304 | 44.0095 | 0.371134 | 28 | 0.236125 | 32 | 0.269857 |
| 55 | 379211.65 | 60 | 0.00006 | 8.3144598 | 295 | 0.00927634 | 44.0095 | 0.408247 | 28 | 0.259738 | 32 | 0.296843 |
| 60 | 413685.44 | 60 | 0.00006 | 8.3144598 | 295 | 0.01011965 | 44.0095 | 0.445361 | 28 | 0.28335 | 32 | 0.323829 |
| 65 | 448159.22 | 60 | 0.00006 | 8.3144598 | 295 | 0.01096295 | 44.0095 | 0.482474 | 28 | 0.306963 | 32 | 0.350814 |
| 70 | 482633.01 | 60 | 0.00006 | 8.3144598 | 295 | 0.01180626 | 44.0095 | 0.519587 | 28 | 0.330575 | 32 | 0.3778 |
| 75 | 517106.80 | 60 | 0.00006 | 8.3144598 | 295 | 0.01264956 | 44.0095 | 0.556701 | 28 | 0.354188 | 32 | 0.404786 |

TABLE 15

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 65 | 0.000065 | 8.3144598 | 295 | 0.00091358 | 44.0095 | 0.040206 | 28 | 0.02558 | 32 | 0.029235 |
| 10 | 68947.57 | 65 | 0.000065 | 8.3144598 | 295 | 0.00182716 | 44.0095 | 0.080412 | 28 | 0.05116 | 32 | 0.058469 |
| 15 | 103421.36 | 65 | 0.000065 | 8.3144598 | 295 | 0.00274074 | 44.0095 | 0.120619 | 28 | 0.076741 | 32 | 0.087704 |
| 20 | 137895.15 | 65 | 0.000065 | 8.3144598 | 295 | 0.00365432 | 44.0095 | 0.160825 | 28 | 0.102321 | 32 | 0.116938 |
| 25 | 172368.93 | 65 | 0.000065 | 8.3144598 | 295 | 0.00456790 | 44.0095 | 0.201031 | 28 | 0.127901 | 32 | 0.146173 |
| 30 | 206842.72 | 65 | 0.000065 | 8.3144598 | 295 | 0.00548148 | 44.0095 | 0.241237 | 28 | 0.153481 | 32 | 0.175407 |
| 35 | 241316.50 | 65 | 0.000065 | 8.3144598 | 295 | 0.00639506 | 44.0095 | 0.281443 | 28 | 0.179062 | 32 | 0.204642 |
| 40 | 275790.29 | 65 | 0.000065 | 8.3144598 | 295 | 0.00730864 | 44.0095 | 0.321649 | 28 | 0.204642 | 32 | 0.233876 |
| 45 | 310264.08 | 65 | 0.000065 | 8.3144598 | 295 | 0.00822221 | 44.0095 | 0.361856 | 28 | 0.230222 | 32 | 0.263111 |
| 50 | 344737.86 | 65 | 0.000065 | 8.3144598 | 295 | 0.00913579 | 44.0095 | 0.402062 | 28 | 0.255802 | 32 | 0.292345 |
| 55 | 379211.65 | 65 | 0.000065 | 8.3144598 | 295 | 0.01004937 | 44.0095 | 0.442268 | 28 | 0.281382 | 32 | 0.32158 |
| 60 | 413685.44 | 65 | 0.000065 | 8.3144598 | 295 | 0.01096295 | 44.0095 | 0.482474 | 28 | 0.306963 | 32 | 0.350814 |
| 65 | 448159.22 | 65 | 0.000065 | 8.3144598 | 295 | 0.01187653 | 44.0095 | 0.52268 | 28 | 0.332543 | 32 | 0.380049 |
| 70 | 482633.01 | 65 | 0.000065 | 8.3144598 | 295 | 0.01279011 | 44.0095 | 0.562886 | 28 | 0.358123 | 32 | 0.409284 |
| 75 | 517106.80 | 65 | 0.000065 | 8.3144598 | 295 | 0.01370369 | 44.0095 | 0.603093 | 28 | 0.383703 | 32 | 0.438518 |

TABLE 16

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 70 | 0.00007 | 8.3144598 | 295 | 0.00098385 | 44.0095 | 0.043299 | 28 | 0.027548 | 32 | 0.031483 |
| 10 | 68947.57 | 70 | 0.00007 | 8.3144598 | 295 | 0.00196771 | 44.0095 | 0.086598 | 28 | 0.055096 | 32 | 0.062967 |
| 15 | 103421.36 | 70 | 0.00007 | 8.3144598 | 295 | 0.00295156 | 44.0095 | 0.129897 | 28 | 0.082644 | 32 | 0.09445 |
| 20 | 137895.15 | 70 | 0.00007 | 8.3144598 | 295 | 0.00393542 | 44.0095 | 0.173196 | 28 | 0.110192 | 32 | 0.125933 |
| 25 | 172368.93 | 70 | 0.00007 | 8.3144598 | 295 | 0.00491927 | 44.0095 | 0.216495 | 28 | 0.13774 | 32 | 0.157417 |
| 30 | 206842.72 | 70 | 0.00007 | 8.3144598 | 295 | 0.00590313 | 44.0095 | 0.259794 | 28 | 0.165288 | 32 | 0.1889 |
| 35 | 241316.50 | 70 | 0.00007 | 8.3144598 | 295 | 0.00688698 | 44.0095 | 0.303093 | 28 | 0.192836 | 32 | 0.220383 |
| 40 | 275790.29 | 70 | 0.00007 | 8.3144598 | 295 | 0.00787084 | 44.0095 | 0.346392 | 28 | 0.220383 | 32 | 0.251867 |
| 45 | 310264.08 | 70 | 0.00007 | 8.3144598 | 295 | 0.00885469 | 44.0095 | 0.389691 | 28 | 0.247931 | 32 | 0.28335 |
| 50 | 344737.86 | 70 | 0.00007 | 8.3144598 | 295 | 0.00983855 | 44.0095 | 0.43299 | 28 | 0.275479 | 32 | 0.314834 |
| 55 | 379211.65 | 70 | 0.00007 | 8.3144598 | 295 | 0.01082240 | 44.0095 | 0.476288 | 28 | 0.303027 | 32 | 0.346317 |
| 60 | 413685.44 | 70 | 0.00007 | 8.3144598 | 295 | 0.01180626 | 44.0095 | 0.519587 | 28 | 0.330575 | 32 | 0.3778 |
| 65 | 448159.22 | 70 | 0.00007 | 8.3144598 | 295 | 0.01279011 | 44.0095 | 0.562886 | 28 | 0.358123 | 32 | 0.409284 |
| 70 | 482633.01 | 70 | 0.00007 | 8.3144598 | 295 | 0.01377397 | 44.0095 | 0.606185 | 28 | 0.385671 | 32 | 0.440767 |
| 75 | 517106.80 | 70 | 0.00007 | 8.3144598 | 295 | 0.01475782 | 44.0095 | 0.649484 | 28 | 0.413219 | 32 | 0.47225 |

TABLE 17

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 75 | 0.000075 | 8.3144598 | 295 | 0.00105413 | 44.0095 | 0.046392 | 28 | 0.029516 | 32 | 0.033732 |
| 10 | 68947.57 | 75 | 0.000075 | 8.3144598 | 295 | 0.00210826 | 44.0095 | 0.092783 | 28 | 0.059031 | 32 | 0.067464 |
| 15 | 103421.36 | 75 | 0.000075 | 8.3144598 | 295 | 0.00316239 | 44.0095 | 0.139175 | 28 | 0.088547 | 32 | 0.101196 |
| 20 | 137895.15 | 75 | 0.000075 | 8.3144598 | 295 | 0.00421652 | 44.0095 | 0.185567 | 28 | 0.118063 | 32 | 0.134929 |
| 25 | 172368.93 | 75 | 0.000075 | 8.3144598 | 295 | 0.00527065 | 44.0095 | 0.231959 | 28 | 0.147578 | 32 | 0.168661 |
| 30 | 206842.72 | 75 | 0.000075 | 8.3144598 | 295 | 0.00632478 | 44.0095 | 0.27835 | 28 | 0.177094 | 32 | 0.202393 |
| 35 | 241316.50 | 75 | 0.000075 | 8.3144598 | 295 | 0.00737891 | 44.0095 | 0.324742 | 28 | 0.206609 | 32 | 0.236125 |
| 40 | 275790.29 | 75 | 0.000075 | 8.3144598 | 295 | 0.00843304 | 44.0095 | 0.371134 | 28 | 0.236125 | 32 | 0.269857 |
| 45 | 310264.08 | 75 | 0.000075 | 8.3144598 | 295 | 0.00948717 | 44.0095 | 0.417526 | 28 | 0.265641 | 32 | 0.303589 |
| 50 | 344737.86 | 75 | 0.000075 | 8.3144598 | 295 | 0.01054130 | 44.0095 | 0.463917 | 28 | 0.295156 | 32 | 0.337322 |
| 55 | 379211.65 | 75 | 0.000075 | 8.3144598 | 295 | 0.01159543 | 44.0095 | 0.510309 | 28 | 0.324672 | 32 | 0.371054 |
| 60 | 413685.44 | 75 | 0.000075 | 8.3144598 | 295 | 0.01264956 | 44.0095 | 0.556701 | 28 | 0.354188 | 32 | 0.404786 |
| 65 | 448159.22 | 75 | 0.000075 | 8.3144598 | 295 | 0.01370369 | 44.0095 | 0.603093 | 28 | 0.383703 | 32 | 0.438518 |
| 70 | 482633.01 | 75 | 0.000075 | 8.3144598 | 295 | 0.01475782 | 44.0095 | 0.649484 | 28 | 0.413219 | 32 | 0.47225 |
| 75 | 517106.80 | 75 | 0.000075 | 8.3144598 | 295 | 0.01581195 | 44.0095 | 0.695876 | 28 | 0.442735 | 32 | 0.505982 |

TABLE 18

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 80 | 0.00008 | 8.3144598 | 295 | 0.00112441 | 44.0095 | 0.049485 | 28 | 0.031483 | 32 | 0.035981 |
| 10 | 68947.57 | 80 | 0.00008 | 8.3144598 | 295 | 0.00224881 | 44.0095 | 0.098969 | 28 | 0.062967 | 32 | 0.071962 |
| 15 | 103421.36 | 80 | 0.00008 | 8.3144598 | 295 | 0.00337322 | 44.0095 | 0.148454 | 28 | 0.09445 | 32 | 0.107943 |
| 20 | 137895.15 | 80 | 0.00008 | 8.3144598 | 295 | 0.00449762 | 44.0095 | 0.197938 | 28 | 0.125933 | 32 | 0.143924 |
| 25 | 172368.93 | 80 | 0.00008 | 8.3144598 | 295 | 0.00562203 | 44.0095 | 0.247423 | 28 | 0.157417 | 32 | 0.179905 |
| 30 | 206842.72 | 80 | 0.00008 | 8.3144598 | 295 | 0.00674643 | 44.0095 | 0.296907 | 28 | 0.1889 | 32 | 0.215886 |
| 35 | 241316.50 | 80 | 0.00008 | 8.3144598 | 295 | 0.00787084 | 44.0095 | 0.346392 | 28 | 0.220383 | 32 | 0.251867 |
| 40 | 275790.29 | 80 | 0.00008 | 8.3144598 | 295 | 0.00899524 | 44.0095 | 0.395876 | 28 | 0.251867 | 32 | 0.287848 |
| 45 | 310264.08 | 80 | 0.00008 | 8.3144598 | 295 | 0.01011965 | 44.0095 | 0.445361 | 28 | 0.28335 | 32 | 0.323829 |
| 50 | 344737.86 | 80 | 0.00008 | 8.3144598 | 295 | 0.01124405 | 44.0095 | 0.494845 | 28 | 0.314834 | 32 | 0.35981 |
| 55 | 379211.65 | 80 | 0.00008 | 8.3144598 | 295 | 0.01236846 | 44.0095 | 0.54433 | 28 | 0.346317 | 32 | 0.395791 |
| 60 | 413685.44 | 80 | 0.00008 | 8.3144598 | 295 | 0.01349286 | 44.0095 | 0.593814 | 28 | 0.3778 | 32 | 0.431772 |
| 65 | 448159.22 | 80 | 0.00008 | 8.3144598 | 295 | 0.01461727 | 44.0095 | 0.643299 | 28 | 0.409284 | 32 | 0.467753 |
| 70 | 482633.01 | 80 | 0.00008 | 8.3144598 | 295 | 0.01574168 | 44.0095 | 0.692783 | 28 | 0.440767 | 32 | 0.503734 |
| 75 | 517106.80 | 80 | 0.00008 | 8.3144598 | 295 | 0.01686608 | 44.0095 | 0.742268 | 28 | 0.47225 | 32 | 0.539715 |

TABLE 19

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 85 | 0.000085 | 8.3144598 | 295 | 0.00119468 | 44.0095 | 0.052577 | 28 | 0.033451 | 32 | 0.03823 |
| 10 | 68947.57 | 85 | 0.000085 | 8.3144598 | 295 | 0.00238936 | 44.0095 | 0.105155 | 28 | 0.066902 | 32 | 0.07646 |
| 15 | 103421.36 | 85 | 0.000085 | 8.3144598 | 295 | 0.00358404 | 44.0095 | 0.157732 | 28 | 0.100353 | 32 | 0.114689 |
| 20 | 137895.15 | 85 | 0.000085 | 8.3144598 | 295 | 0.00477872 | 44.0095 | 0.210309 | 28 | 0.133804 | 32 | 0.152919 |
| 25 | 172368.93 | 85 | 0.000085 | 8.3144598 | 295 | 0.00597340 | 44.0095 | 0.262887 | 28 | 0.167255 | 32 | 0.191149 |
| 30 | 206842.72 | 85 | 0.000085 | 8.3144598 | 295 | 0.00716808 | 44.0095 | 0.315464 | 28 | 0.200706 | 32 | 0.229379 |
| 35 | 241316.50 | 85 | 0.000085 | 8.3144598 | 295 | 0.00836277 | 44.0095 | 0.368041 | 28 | 0.234157 | 32 | 0.267608 |
| 40 | 275790.29 | 85 | 0.000085 | 8.3144598 | 295 | 0.00955745 | 44.0095 | 0.420618 | 28 | 0.267608 | 32 | 0.305838 |
| 45 | 310264.08 | 85 | 0.000085 | 8.3144598 | 295 | 0.01075213 | 44.0095 | 0.473196 | 28 | 0.30106 | 32 | 0.344068 |
| 50 | 344737.86 | 85 | 0.000085 | 8.3144598 | 295 | 0.01194681 | 44.0095 | 0.525773 | 28 | 0.334511 | 32 | 0.382298 |
| 55 | 379211.65 | 85 | 0.000085 | 8.3144598 | 295 | 0.01314149 | 44.0095 | 0.57835 | 28 | 0.367962 | 32 | 0.420528 |
| 60 | 413685.44 | 85 | 0.000085 | 8.3144598 | 295 | 0.01433617 | 44.0095 | 0.630928 | 28 | 0.401413 | 32 | 0.458757 |
| 65 | 448159.22 | 85 | 0.000085 | 8.3144598 | 295 | 0.01553085 | 44.0095 | 0.683505 | 28 | 0.434864 | 32 | 0.496987 |
| 70 | 482633.01 | 85 | 0.000085 | 8.3144598 | 295 | 0.01672553 | 44.0095 | 0.736082 | 28 | 0.468315 | 32 | 0.535217 |
| 75 | 517106.80 | 85 | 0.000085 | 8.3144598 | 295 | 0.01792021 | 44.0095 | 0.78866 | 28 | 0.501766 | 32 | 0.573447 |

TABLE 20

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 90 | 0.00009 | 8.3144598 | 295 | 0.00126496 | 44.0095 | 0.05567 | 28 | 0.035419 | 32 | 0.040479 |
| 10 | 68947.57 | 90 | 0.00009 | 8.3144598 | 295 | 0.00252991 | 44.0095 | 0.11134 | 28 | 0.070838 | 32 | 0.080957 |
| 15 | 103421.36 | 90 | 0.00009 | 8.3144598 | 295 | 0.00379487 | 44.0095 | 0.16701 | 28 | 0.106256 | 32 | 0.121436 |
| 20 | 137895.15 | 90 | 0.00009 | 8.3144598 | 295 | 0.00505982 | 44.0095 | 0.22268 | 28 | 0.141675 | 32 | 0.161914 |
| 25 | 172368.93 | 90 | 0.00009 | 8.3144598 | 295 | 0.00632478 | 44.0095 | 0.27835 | 28 | 0.177094 | 32 | 0.202393 |
| 30 | 206842.72 | 90 | 0.00009 | 8.3144598 | 295 | 0.00758974 | 44.0095 | 0.334021 | 28 | 0.212513 | 32 | 0.242872 |
| 35 | 241316.50 | 90 | 0.00009 | 8.3144598 | 295 | 0.00885469 | 44.0095 | 0.389691 | 28 | 0.247931 | 32 | 0.28335 |
| 40 | 275790.29 | 90 | 0.00009 | 8.3144598 | 295 | 0.01011965 | 44.0095 | 0.445361 | 28 | 0.28335 | 32 | 0.323829 |
| 45 | 310264.08 | 90 | 0.00009 | 8.3144598 | 295 | 0.01138460 | 44.0095 | 0.501031 | 28 | 0.318769 | 32 | 0.364307 |
| 50 | 344737.86 | 90 | 0.00009 | 8.3144598 | 295 | 0.01264956 | 44.0095 | 0.556701 | 28 | 0.354188 | 32 | 0.404786 |
| 55 | 379211.65 | 90 | 0.00009 | 8.3144598 | 295 | 0.01391452 | 44.0095 | 0.612371 | 28 | 0.389606 | 32 | 0.445265 |
| 60 | 413685.44 | 90 | 0.00009 | 8.3144598 | 295 | 0.01517947 | 44.0095 | 0.668041 | 28 | 0.425025 | 32 | 0.485743 |
| 65 | 448159.22 | 90 | 0.00009 | 8.3144598 | 295 | 0.01644443 | 44.0095 | 0.723711 | 28 | 0.460444 | 32 | 0.526222 |
| 70 | 482633.01 | 90 | 0.00009 | 8.3144598 | 295 | 0.01770938 | 44.0095 | 0.779381 | 28 | 0.495863 | 32 | 0.5667 |
| 75 | 517106.80 | 90 | 0.00009 | 8.3144598 | 295 | 0.01897434 | 44.0095 | 0.835051 | 28 | 0.531282 | 32 | 0.607179 |

TABLE 21

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 95 | 0.000095 | 8.3144598 | 295 | 0.00133523 | 44.0095 | 0.058763 | 28 | 0.037386 | 32 | 0.042727 |
| 10 | 68947.57 | 95 | 0.000095 | 8.3144598 | 295 | 0.00267046 | 44.0095 | 0.117526 | 28 | 0.074773 | 32 | 0.085455 |
| 15 | 103421.36 | 95 | 0.000095 | 8.3144598 | 295 | 0.00400569 | 44.0095 | 0.176289 | 28 | 0.112159 | 32 | 0.128182 |
| 20 | 137895.15 | 95 | 0.000095 | 8.3144598 | 295 | 0.00534093 | 44.0095 | 0.235051 | 28 | 0.149546 | 32 | 0.17091 |
| 25 | 172368.93 | 95 | 0.000095 | 8.3144598 | 295 | 0.00667616 | 44.0095 | 0.293814 | 28 | 0.186932 | 32 | 0.213637 |
| 30 | 206842.72 | 95 | 0.000095 | 8.3144598 | 295 | 0.00801139 | 44.0095 | 0.352577 | 28 | 0.224319 | 32 | 0.256364 |
| 35 | 241316.50 | 95 | 0.000095 | 8.3144598 | 295 | 0.00934662 | 44.0095 | 0.41134 | 28 | 0.261705 | 32 | 0.299092 |
| 40 | 275790.29 | 95 | 0.000095 | 8.3144598 | 295 | 0.01068185 | 44.0095 | 0.470103 | 28 | 0.299092 | 32 | 0.341819 |
| 45 | 310264.08 | 95 | 0.000095 | 8.3144598 | 295 | 0.01201708 | 44.0095 | 0.528866 | 28 | 0.336478 | 32 | 0.384547 |
| 50 | 344737.86 | 95 | 0.000095 | 8.3144598 | 295 | 0.01335231 | 44.0095 | 0.587629 | 28 | 0.373865 | 32 | 0.427274 |
| 55 | 379211.65 | 95 | 0.000095 | 8.3144598 | 295 | 0.01468755 | 44.0095 | 0.646392 | 28 | 0.411251 | 32 | 0.470001 |
| 60 | 413685.44 | 95 | 0.000095 | 8.3144598 | 295 | 0.01602278 | 44.0095 | 0.705154 | 28 | 0.448638 | 32 | 0.512729 |
| 65 | 448159.22 | 95 | 0.000095 | 8.3144598 | 295 | 0.01735801 | 44.0095 | 0.763917 | 28 | 0.486024 | 32 | 0.555456 |
| 70 | 482633.01 | 95 | 0.000095 | 8.3144598 | 295 | 0.01869324 | 44.0095 | 0.82268 | 28 | 0.523411 | 32 | 0.598184 |
| 75 | 517106.80 | 95 | 0.000095 | 8.3144598 | 295 | 0.02002847 | 44.0095 | 0.881443 | 28 | 0.560797 | 32 | 0.640911 |

TABLE 22

| Pressure (psi) | Pressure (pa) | Volume (cm3) | Volume (m3) | R (ideal gas constant- J/K · mol) | T (Kelvin) | n (number of moles of gas) = (pV)/(RT) | MW of CO2 (g/mol) | Amount of CO2 | MW of N2 (g/mol) | Amount of N2 (g) | MW of O2 (g/mol) | Amount of O2 (g) |
|---|---|---|---|---|---|---|---|---|---|---|---|---|
| 5 | 34473.79 | 100 | 0.0001 | 8.3144598 | 295 | 0.00140551 | 44.0095 | 0.061856 | 28 | 0.039354 | 32 | 0.044976 |
| 10 | 68947.57 | 100 | 0.0001 | 8.3144598 | 295 | 0.00281101 | 44.0095 | 0.123711 | 28 | 0.078708 | 32 | 0.089952 |
| 15 | 103421.36 | 100 | 0.0001 | 8.3144598 | 295 | 0.00421652 | 44.0095 | 0.185567 | 28 | 0.118063 | 32 | 0.134929 |
| 20 | 137895.15 | 100 | 0.0001 | 8.3144598 | 295 | 0.00562203 | 44.0095 | 0.247423 | 28 | 0.157417 | 32 | 0.179905 |
| 25 | 172368.93 | 100 | 0.0001 | 8.3144598 | 295 | 0.00702753 | 44.0095 | 0.309278 | 28 | 0.196771 | 32 | 0.224881 |
| 30 | 206842.72 | 100 | 0.0001 | 8.3144598 | 295 | 0.00843304 | 44.0095 | 0.371134 | 28 | 0.236125 | 32 | 0.269857 |
| 35 | 241316.50 | 100 | 0.0001 | 8.3144598 | 295 | 0.00983855 | 44.0095 | 0.43299 | 28 | 0.275479 | 32 | 0.314834 |
| 40 | 275790.29 | 100 | 0.0001 | 8.3144598 | 295 | 0.01124405 | 44.0095 | 0.494845 | 28 | 0.314834 | 32 | 0.35981 |
| 45 | 310264.08 | 100 | 0.0001 | 8.3144598 | 295 | 0.01264956 | 44.0095 | 0.556701 | 28 | 0.354188 | 32 | 0.404786 |
| 50 | 344737.86 | 100 | 0.0001 | 8.3144598 | 295 | 0.01405507 | 44.0095 | 0.618556 | 28 | 0.393542 | 32 | 0.449762 |
| 55 | 379211.65 | 100 | 0.0001 | 8.3144598 | 295 | 0.01546057 | 44.0095 | 0.680412 | 28 | 0.432896 | 32 | 0.494738 |
| 60 | 413685.44 | 100 | 0.0001 | 8.3144598 | 295 | 0.01686608 | 44.0095 | 0.742268 | 28 | 0.47225 | 32 | 0.539715 |
| 65 | 448159.22 | 100 | 0.0001 | 8.3144598 | 295 | 0.01827159 | 44.0095 | 0.804123 | 28 | 0.511604 | 32 | 0.584691 |
| 70 | 482633.01 | 100 | 0.0001 | 8.3144598 | 295 | 0.01967709 | 44.0095 | 0.865979 | 28 | 0.550959 | 32 | 0.629667 |
| 75 | 517106.80 | 100 | 0.0001 | 8.3144598 | 295 | 0.02108260 | 44.0095 | 0.927835 | 28 | 0.590313 | 32 | 0.674643 |

As noted above, the internal volume that the pressurized fluid is intended to fill can vary between implementation as well. For example, as noted above, the total internal volume can vary between 10-50 cm$^3$. When the internal volume is less than the volume as used in the above calculations (25 cm$^3$), the amount of the individual chemicals can be reduced as a lesser amount of pressurized fluid may be used. Conversely, when the internal volume is greater than the volume as used in the above calculations, the amount of the individual chemicals can be increased as a greater amount of pressurized fluid may be used. For example, a pressure source can include between 0.10 grams and 5 grams of hydrogen peroxide. Similarly, a pressure source can include between 0.50 grams and 7.5 grams of potassium iodide.

It should be noted that the chemicals and amounts used as described in the above examples are for exemplary purposes only. Depending upon the implementation, the amount of pressurized fluid to be created, the amount of internal volume to fill, and the desired pressure, the types of chemicals used and the amounts of those chemicals can be adjusted accordingly.

Pressure Sources Using Pressurized Fluid Reservoirs Overview

As noted above, a pressure source can include a pressurized fluid reservoir as well as a mechanical mechanism for facilitating release of a pressurized fluid contained within the fluid reservoir. The released pressurized fluid can be directed to, for example, a plurality of conductive gel reservoirs for facilitating release of conductive gel stored therein.

Figure 9:
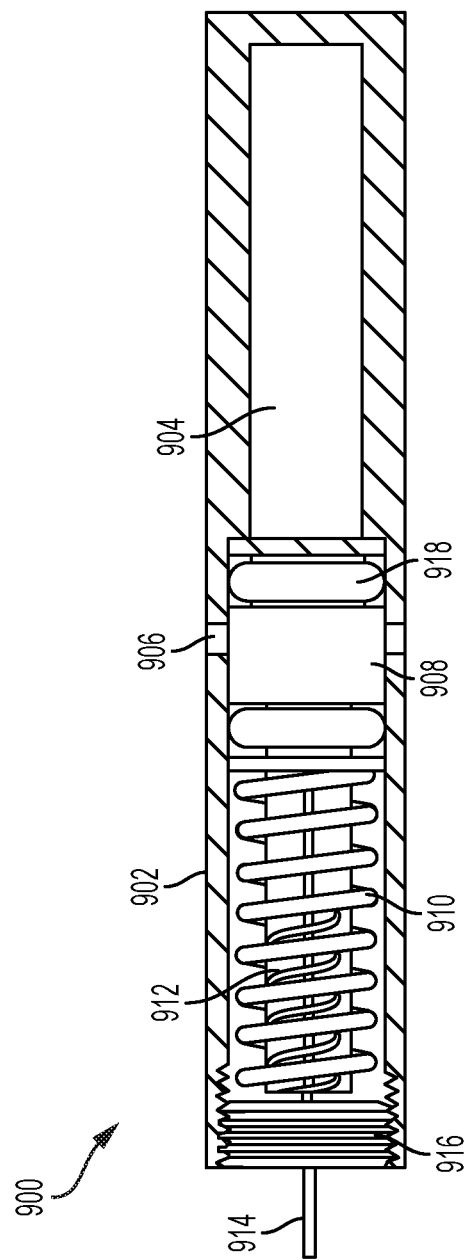
FIG. 9 depicts a pressure source that uses a sliding valve, in accordance with an example of the present disclosure.
Figure 10:
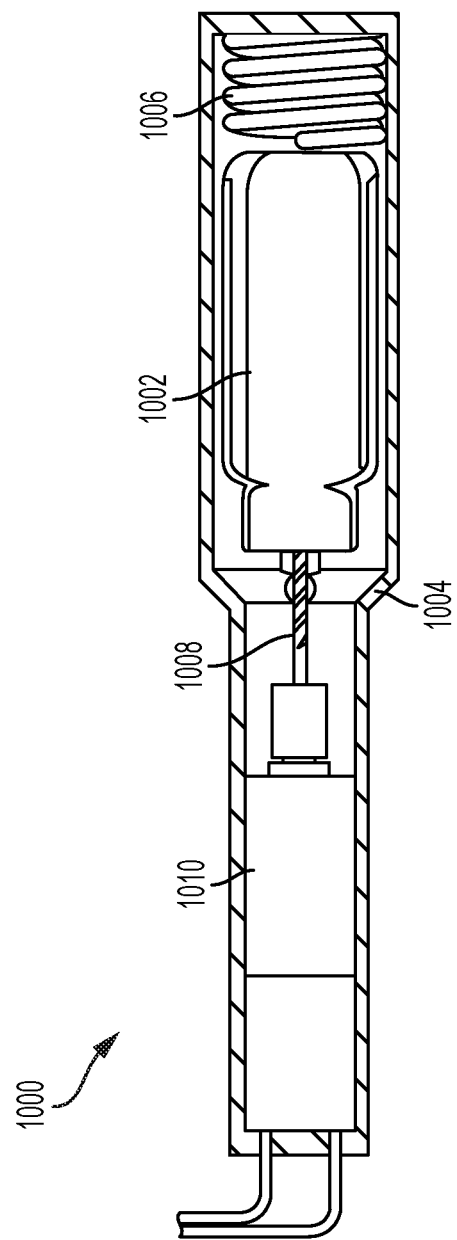
FIG. 10 depicts a pressure source that uses a mechanical puncturing device, in accordance with an example of the present disclosure.
Figure 11A:
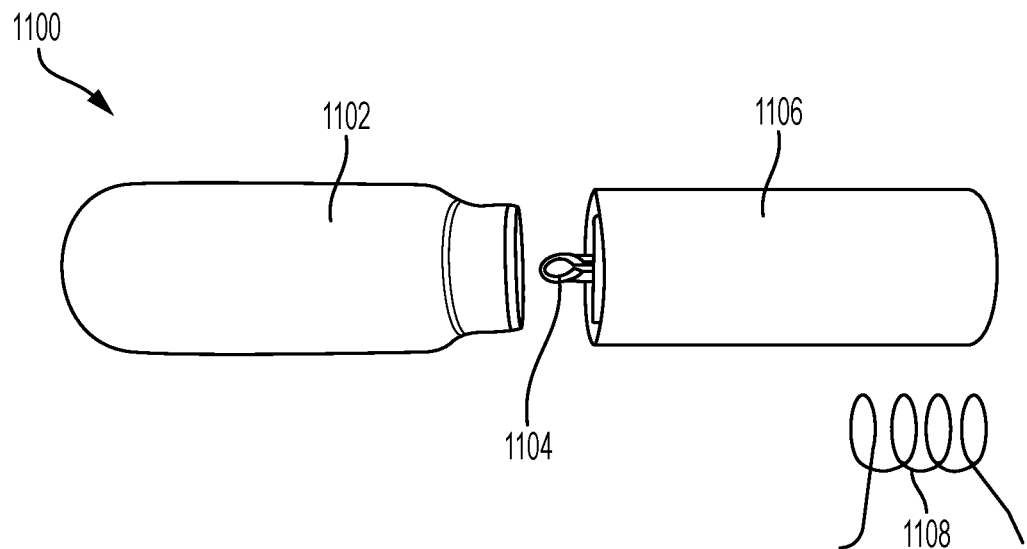
FIGS. 11A and 11B depict various views of a pressure source that uses a puncturing pin, in accordance with an example of the present disclosure.
Figure 11B:
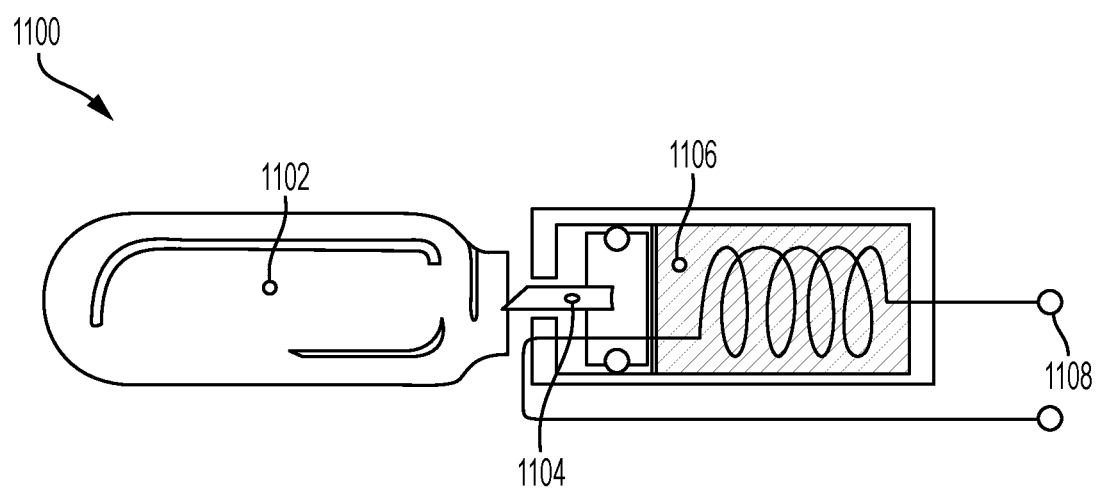

FIGS. 5A-11B illustrate various examples of pressure sources that incorporate a pressurized fluid reservoir, e.g., pressure sources 500 (FIG. 5A), 520 (FIG. 5B), 600 (FIG. 6), 700 (FIG. 7), 800 (FIG. 8), 900 (FIG. 9), 1000 (FIG. 10), and 1100 (FIG. 11). In operation, one example of a pressure source as described in FIGS. 5A-11 can be integrated into a therapy electrode such as therapy electrode 200 as discussed above, e.g., replacing pressure source 240 as discussed in reference to therapy electrode 200. A controller, such as medical device controller 120, can be operably connected to the pressure source. The medical device controller 120 can be configured to provide an electrical signal to the pressure source prior to delivery of, for example, a therapeutic shock to a patient. The electrical signal can be configured to facilitate or otherwise initiate a release of the pressurized fluid from the pressurized fluid reservoir. The pressurized fluid can then be directed through the fluid channel 230 to the conductive gel reservoirs 210, thereby causing release of the conductive gel stored therein.

The pressure sources as described in relation to FIGS. 5A-11 include, for example, a preloaded amount of pressurized fluid contained in a sealed or otherwise isolated reservoir. In some implementations, the pressurized fluid can be one of compressed nitrogen gas or compressed carbon dioxide gas. In some implementations, the pressurized fluid can be one of compressed argon gas stored in a high compression pressure vessel. The design of and materials used to manufacture the reservoir can be chosen based upon the type of pressurized fluid being used, as well as the pressure that the pressurized fluid is to be contained at. In some implementations, the reservoir can be manufactured from a metal such as stainless steel or aluminum. The thickness of the walls of the sealed reservoir can be sized such that the reservoir contains the pressurized fluid is designed to minimize a chance of leakage or accidental release due to reservoir failure. For example, the pressurized fluid can be loaded into the sealed reservoir at 100 psi. As such, the sealed reservoir can be designed to accommodate larger internal pressures than the 100 psi the pressurized fluid will be loaded. In some implementations, the walls of the sealed reservoir can be sized approximately 0.0075-0.0125 inches thick. In other examples, the walls of the sealed reservoir can be sized approximately 0.005-0.25 inches thick, depending upon what material is used to manufacture the walls. For example, if a thermoplastic such as the ionomer resin is used, a thicker wall (e.g., 0.125 inches) can be used to compensate for the lower tensile strength of the ionomer resin as compared to stainless steel. Conversely, if a metal such as stainless steel is used, the wall thickness can be lower (e.g., 0.0075 inches) as a result of the higher tensile strength of the stainless steel as compared to a thermoplastic material.

Depending upon the intended application of the pressure source, a certain pressure level of the pressurized fluid can be configured to, for example, facilitate conductive gel release in a conductive gel deployment device. In some implementations, the pressure sources including a pressurized fluid reservoir as described below can be configured to produce or release a pressurized fluid at approximately 15 psi to 40 psi. In other examples, the pressure sources including a pressurized fluid reservoir can be configured to produce or release a pressurized fluid at about 35 psi. Additionally, based upon the change in volume of the space containing the pressurized fluid (as a result of the pressurized fluid being released from the pressurized fluid reservoir), the pressurized fluid can be stored at a higher pressure relative to the pressure of the pressurized fluid when released. For example, the pressurized fluid can be stored in the pressurized fluid reservoir at approximately 75 to 200 psi. In other examples, the pressurized fluid can be stored in the pressurized fluid reservoir at about 100 psi. In some examples, the pressurized fluid can be stored at levels of between 200 psi to around 2000 psi. For example, pressurized argon gas can be stored at a compressed pressure of around 1750 psi.

Additionally, the pressure sources including a pressurized fluid reservoir as described below can be designed to replace an existing pressure source on a therapy electrode. For example, the pressure sources as described in FIGS. 5A-11B can be sized to replace pressure source 240 on therapy electrode 200 as described above. As such, the pressure sources as described in FIGS. 5A-11B can be sized such that they can fit into the existing space previously occupied by pressure source 240. In one or more implementations, the various components of the pressure sources are sized to fit into this space.

Various mechanical release mechanisms can be used to facilitated release of the pressurized fluid. The individual specifics of the example designs are described below in additional detail.

Pressure Source Having a Meltable Plug

Figure 5A:
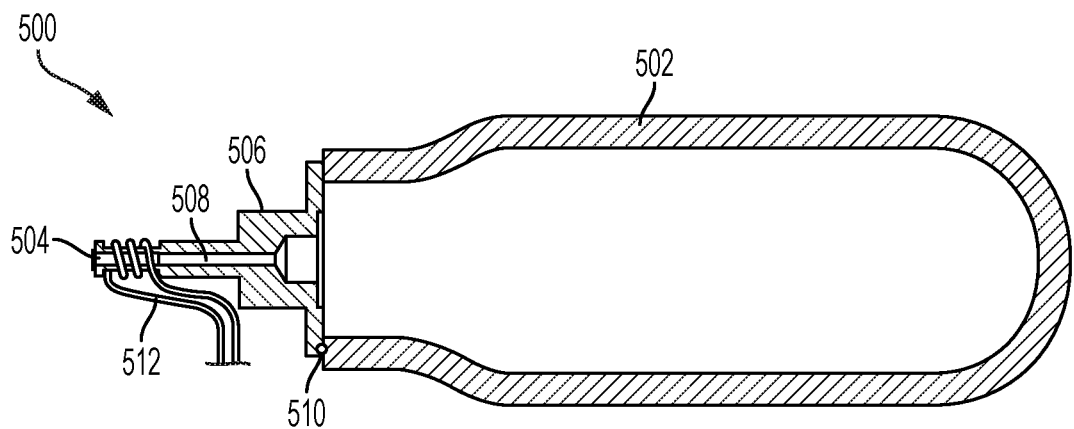
FIGS. 5A and 5B depict pressure sources that uses a meltable plug, in accordance with an example of the present disclosure.

FIG. 5A illustrates a pressure source 500 that can include a pressurized fluid reservoir 502. In some implementations, the pressurized fluid reservoir can be sealed with a meltable plug 504. As described above, the pressurized fluid reservoir 502 can be made from a metal such as stainless steel. The meltable plug 504 can be a metal or epoxy resin with a relatively low melting point as compared to the melting point of the material used to manufacture the pressurized fluid reservoir 502. For example, the meltable plug 504 can be made from a metal solder having a melting point of about 350° F. to 425° F. In some implementations, the meltable plug can be made from a 60%/40% lead/tin combination solder having a melting point of about 375° F. In some implementations, the meltable plug 504 can be made from an epoxy resin such as a fiber-reinforced polymer having a melting point of about 450° F.

An end cap 506 can be affixed to the pressurized fluid reservoir 502. The end cap 506 can be shaped such that it can include an exit port 508. The exit port 508 can be designed such that it defines a small opening relative to the internal diameter of the pressurized fluid reservoir 502, thereby limiting the internal pressure applied to the meltable plug 504 by the pressurized fluid contained therein. The meltable plug 504 can be inserted into the end cap 506 prior to the pressurized fluid being inserted into the pressurized fluid reservoir 502. The pressurized fluid can include an amount of a pressurized liquid or gas that provides an adequate volume and pressure for facilitating release of the conductive gel once the pressurized fluid is released from the pressurized fluid reservoir 502. Similarly, the pressurized fluid can be configured to remain stable when compressed in the typical operating conditions the pressure source 500 can be anticipated to be used. For example, the pressurized fluid can include compressed nitrogen gas.

The pressurized fluid can include any non-noxious gas. Examples are discussed above.

Upon insertion of the pressurized fluid, the end cap 506 can be fixedly attached to the pressurized fluid reservoir 502. Depending upon the material used to manufacture the end cap 506, various methods of attachment can be used. For example, if the end cap 506 is manufactured from a similar metal as the pressurized fluid reservoir 502 (e.g., stainless steel), the end cap 506 can be attached to the pressurized fluid reservoir 502 using a weld 510 about the circumference of the pressurized fluid reservoir 502. To avoid damage to the meltable plug 504, the end cap 506 can be shaped such that the meltable plug 504 is thermally isolated from the weld 510. For example, as shown in FIG. 5A, the end cap 506 can be of a particular length (e.g., 0.25 inches to 0.75 inches) such that the meltable plug 504 can be positioned linearly away from the weld 510. In certain embodiments, the end cap 506 can be approximately 0.5 inches long. As such, any heat produced when welding the end cap 506 to the pressurized fluid reservoir 502 does not damage the meltable plug 504. Additionally, the end cap 506 can have a particular inner diameter such that the meltable plug 504 is easily insertable as compare to other inner diameters, while still providing a large enough opening for pressurized fluid flow. For example, the end cap 506 can have an inner diameter of approximately 0.0125 to 0.075 inches. In certain implementations, the end cap 506 can have an inner diameter of about 0.025 inches.

To facilitate release of the meltable plug 504, the pressure source 500 can include a heating element. As shown in FIG. 5A, a resistive wire 512 can be positioned such that heat produced by the resistive wire 512 is applied to the meltable plug 504, thereby melting or structurally altering the meltable plug 504. Similar to resistive wire 312 as described above, the resistive wire 512 can be constructed from a material that produces heat in response to an applied current. For example, the resistive wire 512 can be made from nickel chromium. The thickness of the resistive wire 512 can be selected such that the temperature of the wire, when an appropriate current is applied, exceeds the melting point of the meltable plug 504. For example, a 20-gauge to a 28-gauge wire can be used, the wire configured to heat to approximately 350° F. to 450° F. In certain implementations, a 24-gauge nickel chromium wire having a 0.020-inch diameter can heat to 400° F. at relatively low amperages as compared to a similarly sized copper wire.

The pressurized fluid contained within the pressurized fluid reservoir 502 can push a liquefied meltable plug 504 out of the exit port 508. The pressurized fluid can flow freely from the pressurized fluid reservoir 502 through, for example, a fluid channel coupled to the exit port 508 and to one or more conductive gel reservoirs.

The pressure source 500 can also include a catch structure to catch any debris that could be ejected when the meltable plug 504 is liquefied and pushed out of the exit port 508. The catch structure can also be configured to provide support for the resistive wire 512.

In operation, the pressure source 500 can be integrated into a therapy electrode such as therapy electrode 200 as discussed above. For example, the pressure source 500 can replace pressure source 240 as discussed in reference to therapy electrode 200. A controller, such as medical device controller 120, can be operably connected to the pressure source 500. The medical device controller 120 can be configured to provide an electrical signal to the pressure source 500 prior to delivery of, for example, a therapeutic shock to a patient. The electrical signal can be directed to the resistive wire 512, thereby heating the resistive wire 512. Once heated, the resistive wire 512 can melt the meltable plug 504. The pressurized fluid contained within the pressurized fluid reservoir 502 can push the meltable plug 504 out of the exit port 508, resulting in flow of the pressurized fluid out of the pressurized fluid reservoir 502. The pressurized fluid flows through the fluid channel 230 to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the resistance of the resistive wire 512, and desired timing for the release of the conductive gel, the medical device controller 120 can be configured to deliver an appropriate electrical signal (e.g., at a high enough current to heat the resistive wire 512) at the appropriate time (e.g., providing for adequate timing for the pressurized fluid release and for the subsequent release of the conductive gel). In some implementations, the pressure source 500 can also include a localized power source that, in response to the signal from the medical device controller 120, is configured to provide a current to the resistive wire 512, thereby heating the resistive wire 512 and liquefying the meltable plug 504.

Figure 5B:
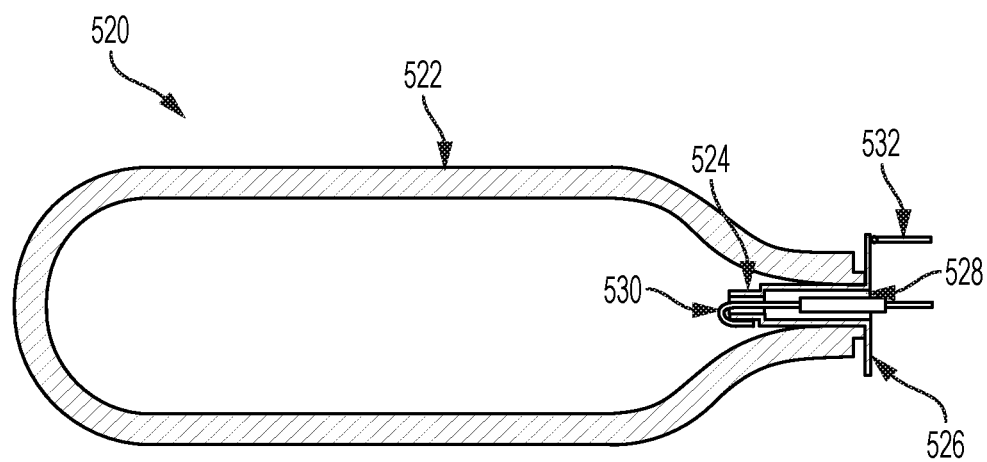

FIG. 5B illustrates a pressure source 520 that can include a pressurized fluid reservoir 522 that can be sealed with a meltable plug 524, similar to that as described in FIG. 5A. However, as shown in FIG. 5B, the shape and design of an end cap 526 can be reversed (as compared to pressure source 500) such that a meltable plug 524 is contained within the pressurized fluid reservoir 522.

In some implementations, the pressurized fluid reservoir 522 can be made from a metal such as stainless steel. The meltable plug 524 can be a metal or epoxy resin with a relatively low melting point as compared to the melting point of the material used to manufacture the pressurized fluid reservoir 522. For example, the meltable plug 524 can be made from a metal solder having a melting point of about 350° F. to 425° F. In some implementations, the meltable plug can be made from a 60%/40% lead/tin combination solder having a melting point of about 375° F. In some implementations, the meltable plug 524 can be made from an epoxy resin such as a fiber-reinforced polymer having a melting point of about 450° F.

An end cap 526 can be affixed to the pressurized fluid reservoir 522. The end cap 526 can be shaped such that it can include an exit port 528. The meltable plug 524 can be inserted into the end cap 526 prior to the pressurized fluid being inserted into the pressurized fluid reservoir 522. The pressurized fluid can include an amount of a pressurized liquid or gas that provides an adequate volume and pressure for facilitating release of the conductive gel once the pressurized fluid is released from the pressurized fluid reservoir 522. Similarly, the pressurized fluid can be configured to remain stable when compressed in any conditions the pressure source 520 can be used. For example, the pressurized fluid can include compressed nitrogen gas.

Upon insertion of the pressurized fluid, the end cap 526 can be fixedly attached to the pressurized fluid reservoir 522. Depending upon the material used to manufacture the end cap 526, various methods of attachment can be used. For example, if the end cap 506 is manufactured from a similar metal as the pressurized fluid reservoir 522 (e.g., stainless steel), the end cap 526 can be attached to the pressurized fluid reservoir 522 using a weld about the circumference of the pressurized fluid reservoir 522. To avoid damage to the meltable plug 524, the end cap 526 can be shaped such that the meltable plug 524 is thermally isolated from the weld. As such, any heat produced when welding the end cap 526 to the pressurized fluid reservoir 522 does not damage the meltable plug 524.

To facilitate release of the meltable plug 524, the pressure source 520 can include a heating element. As shown in FIG. 5B, a resistive wire 530 can be positioned such that heat produced by the resistive wire 530 is applied to the meltable plug 524, thereby melting or structurally altering the meltable plug 524. Depending upon the material used to manufacture the pressurized fluid reservoir 522, the resistive wire 530 can be electrically connected to the pressurized fluid reservoir 522. In such a configuration, the pressurized fluid reservoir can also include a ground wire 532. Thus, current applied to the resistive wire 530 can flow through the resistive wire 530, heating the resistive wire to melt the meltable plug 524. The current can continue to flow through the pressurized fluid reservoir 522 to the ground wire 532. Additionally, the meltable plug 524, if made from, for example, an epoxy resin, can be configured to hold and insulate the resistive wire 530 from the pressurized fluid reservoir 522.

Similar to resistive wire 312 as described above, the resistive wire 530 can be constructed from a material that produces heat in response to an applied current. For example, the resistive wire 530 can be made from nickel chromium. The thickness of the resistive wire 530 can be selected such that the temperature of the wire, when an appropriate current is applied, exceeds the melting point of the meltable plug 524. For example, a 24-gauge nickel chromium wire having a 0.020-inch diameter can heat to 400° F. at relatively low amperages as compared to a similar copper wire.

The pressurized fluid contained within the pressurized fluid reservoir 522 can push a liquefied meltable plug 524 out of the exit port 528. The pressurized fluid can flow freely from the pressurized fluid reservoir 522 through, for example, a fluid channel coupled to the exit port 528 and to one or more conductive gel reservoirs.

The pressure source 520 can also include a catch structure to catch any debris that could be ejected when the meltable plug 524 is liquefied and pushed out of the exit port 528. The catch structure can also be configured to provide support for the resistive wire 530.

In operation, the pressure source 520 can be integrated into a therapy electrode such as therapy electrode 200 as discussed above. For example, the pressure source 520 can replace pressure source 240 as discussed in reference to therapy electrode 200. A controller, such as medical device controller 120, can be operably connected to the pressure source 520. The medical device controller 120 can be configured to provide an electrical signal to the pressure source 520 prior to delivery of, for example, a therapeutic shock to a patient. The electrical signal can be directed to the resistive wire 530, thereby heating the resistive wire 530.

Once heated, the resistive wire 530 can melt the meltable plug 524. The pressurized fluid contained within the pressurized fluid reservoir 522 can push the meltable plug 524 out of the exit port 528, resulting in flow of the pressurized fluid out of the pressurized fluid reservoir 522. The pressurized fluid flows through the fluid channel 230 to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the resistance of the resistive wire 530, and desired timing for the release of the conductive gel, the medical device controller 120 can be configured to deliver an appropriate electrical signal (e.g., at a high enough current to heat the resistive wire 530) at the appropriate time (e.g., providing for adequate timing for the pressurized fluid release and for the subsequent release of the conductive gel). In some implementations, the pressure source 520 can also include a localized power source that, in response to the signal from the medical device controller 120, is configured to provide a current to the resistive wire 530, thereby heating the resistive wire 530 and liquefying the meltable plug 524.

Pressure Source Having a Spring-Force Retaining Element

Figure 6:
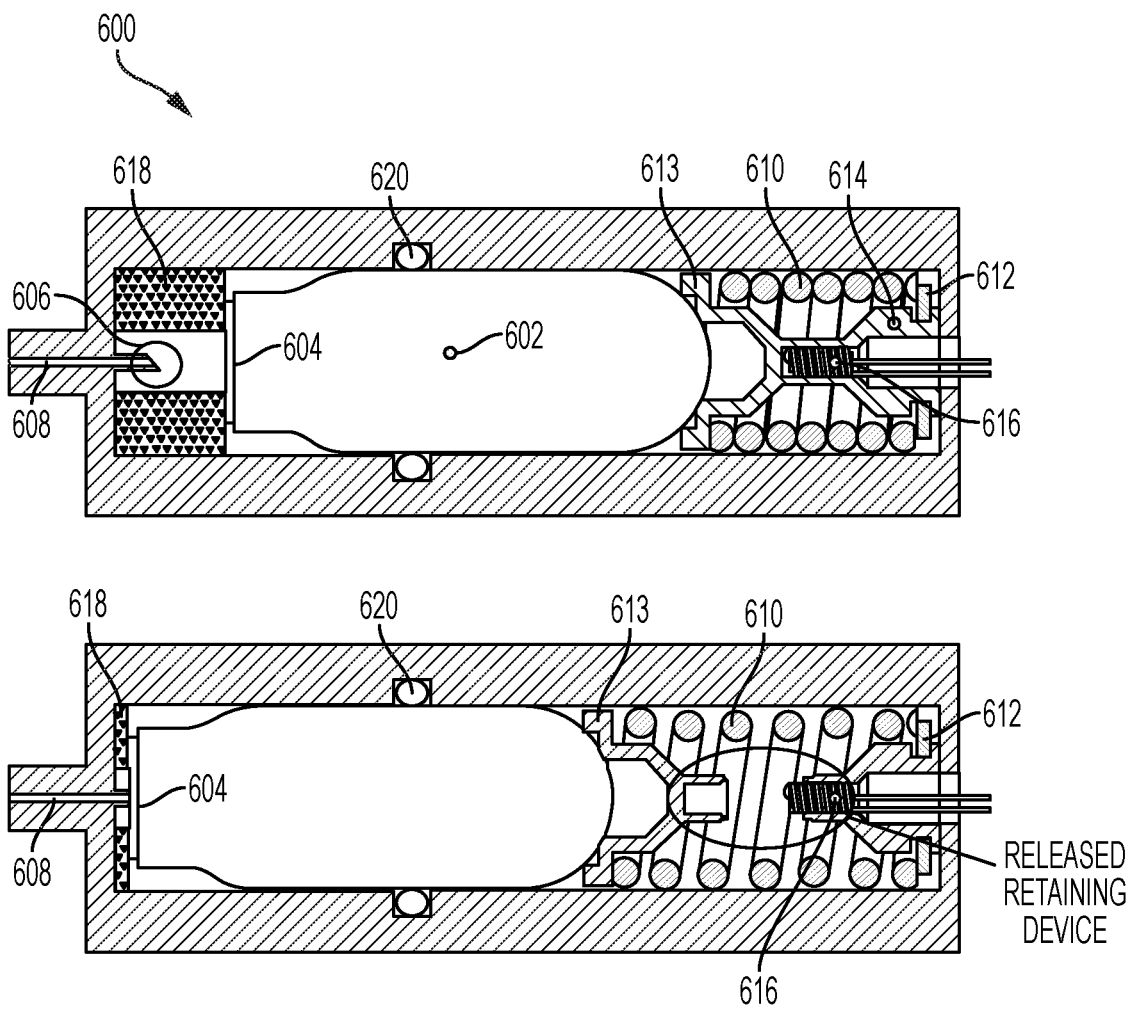
FIG. 6 depicts a pressure source that uses a puncturing pin, in accordance with an example of the present disclosure.

FIG. 6 illustrates a pressure source 600 that can include a pressurized fluid reservoir 602 sealed with a pierceable end 604 such as a rupture disk. As described above, the pressurized fluid reservoir 602 can be made from a metal such as stainless steel. The pierceable end 604 can be made from a thinner metal such as stainless steel foil that is susceptible to piercing when a sharp object is pressed against it at a predetermined pressure. As shown in FIG. 6, a puncturing pin 606 can be positioned substantially proximate the pierceable end 604 (as shown in the top image of FIG. 6). After movement of the pressurized fluid reservoir 602 (as shown in the bottom image of FIG. 6), the puncturing pin 606 can pierced the pierceable end 604 of the pressurized fluid reservoir 602, thereby releasing the pressurized fluid contained therein. In certain implementations, the puncturing pin 606 can be hollow or otherwise fluted to direct flow of the released pressurized fluid to an exit port 608.

To facilitate movement of the pressurized fluid reservoir 602, a spring assembly can be integrated into the pressure source 600. The top image of FIG. 6 illustrates the spring assembly in a set and retained position, while the bottom image of FIG. 6 illustrates the spring assembly in a released position. The spring assembly can include a spring 610 that is designed and configured to apply an outward spring force. In certain implementations, the spring 610 can be configured to exert a force of about 0.5N to 1.0N. For example, the spring 610 can be configured to exert a force of about 0.75N. In certain implementations, the spring 610 can be positioned against a retaining ring 612 as well as a pushing assembly 613. The retaining ring 612 can be positioned to absorb the spring force applied to it by the spring 610 without moving relative to the other components in the pressure source 600. As such, the retaining ring 612 can be configured to provide a stable base against which the spring 610 can exert its spring force. The pushing assembly 613 can be positioned on the opposite end of the spring 610 from the retaining ring 612. The pushing assembly 613 can be positioned adjacent to (or substantially adjacent to) the end of the pressurized fluid reservoir 602 opposite the pierceable end 604. The spring 610 can be compressed and held in the compressed position (as shown in the top image of FIG. 6) by a retaining device 614.

The retaining device 614 can be designed to release at an appropriate time to facilitate release of the pressurized fluid from the pressurized fluid reservoir 602. For example, the retaining device 614 can be constructed from a material that is designed to release the spring 610 in response to one or more applied conditions. In certain implementations, the retaining device 614 can be manufactured from a thermoplastic such as polyethylene. In order to release the spring 610, the retaining device 614 can be caused to release by, for example, melting the retaining device 614. To facilitate melting of the retaining device 614, a resistive wire 616 can be positioned such that heat produced by the resistive wire 616 can be applied to the retaining device 614, thereby melting or structurally weakening the retaining device 614. Once the retaining device 614 is melted or structurally weakened, the spring 610 can be release to extend to its relaxed state (as shown in the lower image of FIG. 6). Similar to resistive wire 312 as described above, the resistive wire 616 can be constructed from a material that produces heat in response to an applied current. For example, the resistive wire 616 can be made from nickel chromium having an appropriate thickness to generate enough heat to melt the retaining device 614.

In some examples, to prevent accidental release of the pressurized fluid (e.g., from the pressurized fluid reservoir 602 accidentally sliding into contact with the puncturing pin 606), the pressure source 600 can include a foam disc 618 that can be configured and positioned to prevent movement of the pressurized fluid reservoir 602 under normal operating conditions. In certain implementations, upon release of the spring 610 (e.g., from the release of the retaining device 614), the foam disc 618 can be compressed (as shown in the lower image of FIG. 6). Thus, the foam disc 618 can be positioned within the pressure source 600 such that it does not prevent operation of the pressure source 600. In some examples, in order to be compressed by the spring 610, the foam disc 618 can be manufactured from an open cell foam such as open cell polyurethane foam.

In certain implementations, the pressure source 600 can include an O-ring 620 positioned to prevent backflow of the pressurized fluid when released from the pressurized fluid reservoir 602. As shown in FIG. 6, the O-ring 620 can be positioned around the pressurized fluid reservoir 602 to prevent backflow while not restricting movement of the pressurized fluid reservoir 602 during operation of the pressure source 600. In certain implementations, the O-ring 620 can be made from a thermoplastic elastomer such as synthetic rubber.

In operation, the pressure source 600 can be integrated into a therapy electrode such as therapy electrode 200 as discussed above. For example, the pressure source 600 can replace pressure source 240 as discussed in reference to therapy electrode 200. A controller, such as medical device controller 120, can be operably connected to the pressure source 600. The medical device controller 120 can be configured to provide an electrical signal to the pressure source 600 prior to delivery of, for example, a therapeutic shock to a patient. The electrical signal can be directed to the resistive wire 616, thereby heating the resistive wire 616. Once heated, the resistive wire 616 can melt or otherwise weaken the retaining device 614. The weakened retaining device 614 can split or otherwise break, causing release of the spring 610. The spring 610, as it returns to its resting position, can exert a spring force on the pushing assembly 613, thereby facilitating movement of the pressurized fluid reservoir 602. The pressurized fluid reservoir 602 can compress the foam disc 618 and contact the puncturing pin 606. The puncturing pin 606 can puncture the pierceable end 604 of the pressurized fluid reservoir 602, resulting in release of the pressurized fluid contained therein. The pressurized fluid can flow into the exit port 608, while the O-ring 620 can prevent backflow of the pressurized fluid. The pressurized fluid can flow through exit port 608 into the fluid channel 230 and to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the resistance of the resistive wire 616, and desired timing for the release of the conductive gel, the medical device controller 120 can be configured to deliver an appropriate electrical signal (e.g., at a high enough current to heat the resistive wire 616 to melt the retaining device 614) at the appropriate time (e.g., providing for adequate timing for the release of the pressurized fluid and for the subsequent release of the conductive gel). In some implementations, the pressure source 600 can also include a localized power source that, in response to the signal from the medical device controller 120, can be configured to provide a current to the resistive wire 616, thereby heating the resistive wire 616 and melting the retaining device 614.

Pressure Source Having a Sliding Valve

Figure 7A:
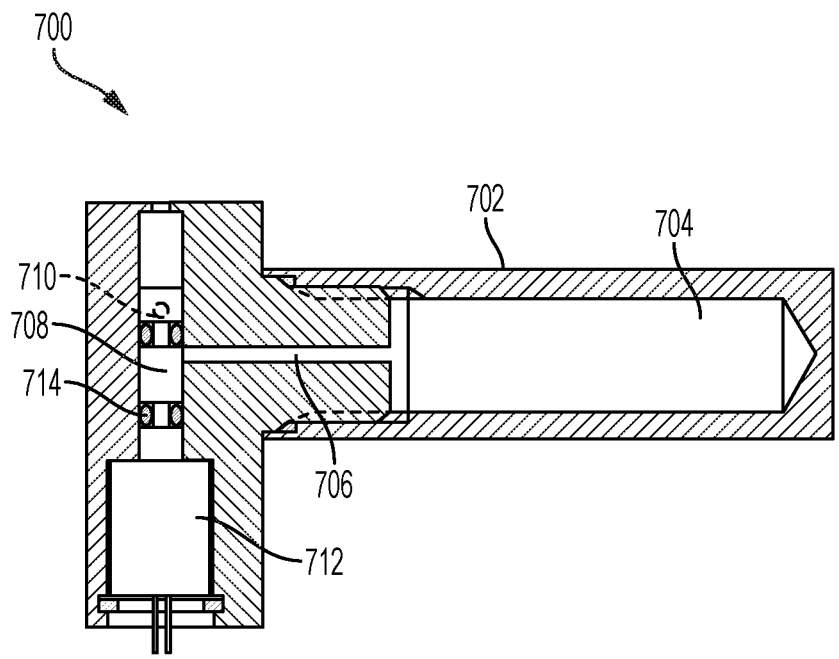
FIGS. 7A and 7B depict multiple views of a pressure source that uses a sliding valve, in accordance with an example of the present disclosure.
Figure 7B:
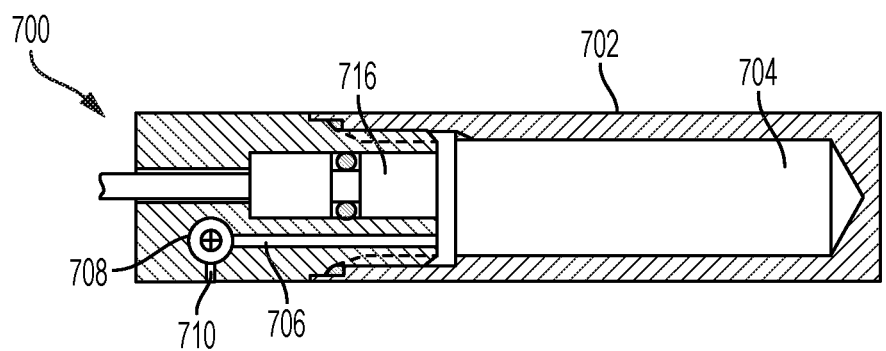

FIGS. 7A and 7B illustrate a pressure source 700 that can include a housing 702. The housing 702 can be configured to both house an amount of a pressurized fluid in one end and various components for facilitating release of the pressurized fluid. FIG. 7A illustrates a sample top cross-sectional view, while FIG. 7B illustrates a sample side cross-sectional view of pressure source 700.

The housing 702 can be formed from a material that is strong enough to withstand the pressure exerted by the pressurized fluid contained therein. For example, the housing 702 can be made from a metal such as stainless steel or aluminum. The metal can be stamped, rolled, or similarly formed to contain the pressurized fluid and other components related to facilitating release of the pressurized fluid. In another example, the housing 702 can be formed from a thermoplastic plastic such as polyethylene. The plastic can be formed by a thermoforming process, an injection molding process, or other similar forming process.

The housing 702 can include a pressurized fluid reservoir 704 configured to contain an amount of a pressurized fluid. The pressurized fluid reservoir 704 can be connected to an internal fluid conduit 706 such that the pressurized fluid can flow through the internal fluid conduit 706. A sliding valve 708 can be positioned substantially adjacent to an end of the internal fluid conduit 706 opposite the pressurized fluid reservoir 704. In certain implementations, the sliding valve 708 can be configured to slide such that it moves from a closed position to an open position. When in the closed position, the sliding valve 708 can interrupt a fluid connection between the fluid conduit 706 and an exit port 710. When in the open position, the sliding valve 708 can move to a position where the fluid conduit 706 and the exit port 710 are in fluid communication. Thus, in certain implementations, when the sliding valve 708 is in the open position, the exit port 710 and the internal fluid conduit 706 can form a fluid pathway for flow of the pressurized fluid out of the pressurized fluid reservoir 704. Conversely, when the sliding valve 708 is in the closed position, the fluid pathway can be broken and the pressurized fluid can remain contained within the pressurized fluid reservoir 704.

To facilitate movement of the sliding valve 708, the sliding valve 708 can be connected to a movement causing device such as solenoid 712. The solenoid 712 can be positioned and configured to either push or pull the sliding valve 708. For example, in response to an electrical signal from a controller, the solenoid 712 can apply a pulling force to the sliding valve 708, resulting in the sliding valve 708 moving to the open position such that the exit port 710 is in fluid communication with the internal fluid conduit 706.

The sliding valve 708 can also include one or more O-rings 714 positioned to prevent backflow (or misdirected flow) of the pressurized fluid as well as to stabilize and secure the moving components of the sliding valve 708 within the housing 702. In certain implementations, the O-rings 714 can be made from a thermoplastic elastomer such as synthetic rubber.

The pressure source 700 can also include a pressure sensor 716. The pressure sensor 716 can be configured to monitor the internal pressure of the pressurized fluid reservoir 704. The pressure sensor 716 can be operably connected to, for example, a controller such as medical device controller 120. The medical device controller 120 can monitor the pressure of the pressurized fluid contained within pressure source 700 and provide an indication of any potential malfunctions (e.g., if the pressure falls below a set threshold).

In operation, the pressure source 700 can be integrated into a therapy electrode such as therapy electrode 200 as discussed above. For example, the pressure source 700 can replace pressure source 240 as discussed in reference to therapy electrode 200. A controller, such as medical device controller 120, can be operably connected to the pressure source 700. The medical device controller 120 can be configured to provide an electrical signal to the pressure source 700 prior to delivery of, for example, a therapeutic shock to a patient. The electrical signal can be directed to the solenoid 712. The solenoid 712 can move the sliding valve 708, thereby establishing a fluid connection between the exit port 710 and the pressurized fluid reservoir 704 (via the fluid conduit 706). The pressurized fluid can flow from the pressurized fluid reservoir 704 to the exit port 710. The pressurized fluid can flow through the fluid channel 230 to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the electrical requirements of the solenoid 712, and desired timing for the release of the conductive gel, the medical device controller 120 can be configured to deliver an appropriate electrical signal (e.g., at a high enough current to move the solenoid 712) at the appropriate time (e.g., providing for adequate timing for the release of the pressurized fluid and for the subsequent release of the conductive gel). In some implementations, the pressure source 700 can also include a localized power source that, in response to the signal from the medical device controller 120, is configured to provide a current to the solenoid 712, thereby facilitating movement of the solenoid 712 and the sliding valve 708.

Additionally, in certain implementations, the pressure source 700 can be designed to be refillable. For example, the sliding valve 708 can be moved to the open position. The pressurized fluid reservoir 704 can be filled with a pressurized fluid injected through the exit port. In certain implementations, the pressure sensor 716 can provide an indication that the internal pressure of the pressurized fluid reservoir 704 has reached a certain point, indicating that the pressurized fluid reservoir 704 is at maximum capacity (determined, for example, based upon the internal volume of the pressurized fluid reservoir 704 and the associated pressure the housing 702 is configured to tolerate). The solenoid 712 can slide the sliding valve 708 into the closed position such that the fluid connection between the exit port 710 and the internal fluid conduit 706 is broken, thereby containing the pressurized fluid within the pressurized fluid reservoir 704.

Pressure Source Having an Actuating Lever

Figure 8:
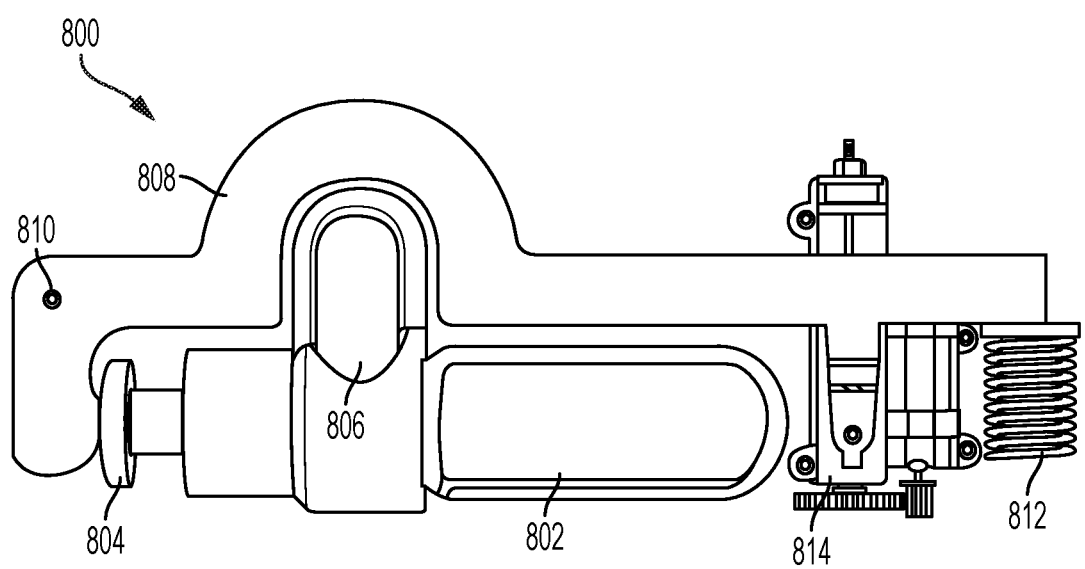
FIG. 8 depicts a pressure source that uses a puncturing pin, in accordance with an example of the present disclosure.

FIG. 8 illustrates a pressure source 800 that can include a pressurized fluid reservoir 802 sealed with a pierceable end. As described above, the pressurized fluid reservoir 802 can be made from a metal such as stainless steel. The pierceable end can be made from a thinner metal such as stainless steel foil that is susceptible to piercing when a sharp object is pressed against it. As shown in FIG. 8, a puncturing pin 804 can be positioned proximate the pierceable end of the pressurized fluid reservoir 802. In certain implementations, the puncturing pin 804 can be configured to move such that the puncturing pin 804 pierces the pierceable end of the pressurized fluid reservoir 802. Upon release of the pressurized fluid from the pressurized fluid reservoir 802, the fluid can be directed to an exit port 806 of the pressure source 800.

To facilitate movement of the puncturing pin 804, an actuating lever assembly can be integrated into the pressure source 800. For example, as shown in FIG. 8, the pressure source 800 can include an actuating lever 808. In certain implementations, the actuating lever 808 can be oriented such that the actuating lever 808 runs parallel to the pressurized fluid reservoir 802. The actuating lever 808 can be manufactured from a material such as aluminum, carbon fiber, or various thermoplastics such as polystyrene. The actuating lever 808 can be configured to pivot about a fulcrum point 810, thereby causing movement of the puncturing pin 804. For example, a vertical movement of the actuating lever 808 can be transferred to the puncturing pin 804 as a horizontal force as a result of the 90° bend in the actuating lever 808 and movement of the actuating lever 808 about the fulcrum point 810.

The pressure source 800 can include a spring 812 that can be configured to facilitate movement of the actuating lever 808. In certain implementations, the spring 812 can be configured to exert an outwardly directed spring force. As such, the spring 812 can be compressed as shown in FIG. 8, thereby resulting in the spring 812 storing the outwardly directed spring force until the spring is released. A release mechanism 814 can be configured to hold the spring 812 in its compressed state until a signal is provided to release the spring 812. The release mechanism 814 can include, for example, a ball screw in combination with a solenoid or other similar motor configured to hold the spring 812 in its compressed state. In certain implementations, upon receiving a signal to release the spring 812, the release mechanism 814 can release the spring 812 from its compressed state. The spring 812 can exert its outwardly directed spring force on the actuating lever 808. The actuating lever 808 can move vertically which, as described above, can be translated to a horizontal movement of the puncturing pin 804.

In operation, the pressure source 800 can be integrated into a therapy electrode such as therapy electrode 200 as discussed above. For example, the pressure source 800 can replace pressure source 240 as discussed in reference to therapy electrode 200. A controller, such as medical device controller 120, can be operably connected to the pressure source 800. The medical device controller 120 can be configured to provide an electrical signal to the pressure source 800 prior to delivery of, for example, a therapeutic shock to a patient. The electrical signal can be directed to the release mechanism 814. In response to the electrical signal, the release mechanism 814 can release the spring 812. The spring 812 can exert a vertical force on the actuating lever 808. The actuating lever 808 can pivot around the fulcrum point 810, transferring a horizontal pushing force to the puncturing pin 804. The puncturing pin 804 can pierce the pierceable end of the pressurized fluid reservoir 802, resulting in release of the pressurized fluid contained therein. The pressurized fluid can flow through exit port 806 into the fluid channel 230 and to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the electrical requirements of the release mechanism 814, and desired timing for the release of the conductive gel, the medical device controller 120 can be configured to deliver an appropriate electrical signal (e.g., at a high enough current to operate the release mechanism 814) at the appropriate time (e.g., providing for adequate timing for the release of the pressurized fluid and for the subsequent release of the conductive gel). In some implementations, the pressure source 800 can also include a localized power source that, in response to the signal from the medical device controller 120, is configured to provide a current to the release mechanism 814, thereby facilitating release of the spring 812.

Pressure Source Having a Fusible Alloy Release

FIG. 9 illustrates a pressure source 900 that can include a body 902. The body 902 can be configured to house both an amount of a pressurized fluid in one end and various components for facilitating release of the pressurized fluid in an opposite end. The body 902 can be formed from, for example, a metal such as stainless steel or aluminum. The body 902 can include two separate bore sizes, a smaller bore at one end for containment of the pressurized fluid (the smaller bore results in thicker walls, thereby increasing the pressure of the fluid that can be contained therein) and a larger bore in the opposite end for containment of the various components. In certain implementations, the smaller bore can result in walls having a thickness of approximately 0.0075 inches thick and the larger bore can result in walls having a thickness of approximately 0.0025 inches thick.

As shown in FIG. 9, the body 902 can include a pressurized fluid reservoir 904 located in the smaller bored end of the body 902. The body 902 can also include one or more exit ports 906 for directing the pressurized fluid to, for example, a fluid channel for facilitating conductive gel release as described above. A piston 908 can be positioned within the body 902 that is positioned and configured to prevent the pressurized fluid from flowing from the pressurized fluid reservoir 904 to the exit ports 906 at unwanted times.

The pressure source 900 can include various components for facilitating release of the pressurized fluid from the pressurized fluid reservoir 904. In some implementations, the pressure source can include a spring 910 that can be configured to apply a spring force against the piston 908 to aid in unwanted movement of the piston 908. Additionally, a meltable alloy plug 912 can be positioned within the body 902 to oppose movement of the piston 908. In certain implementations, the pressurized fluid can exert a first force on the piston 908 in a first direction (e.g., to the left of FIG. 9). The combination of the spring 910 and the meltable alloy plug 912 can provide a second force on the piston 908 in a second direction opposite to the first force (e.g., to the right of FIG. 9) and essentially equal in magnitude to the first force. In certain implementations, the first force and the second force can be approximately 1 N.

In some examples, the piston 908 can remain motionless as the two forces are balanced. In order to facilitate movement of the piston 908, the meltable alloy plug 912 can be designed to release or otherwise cease opposing movement of the piston 908 at an appropriate time. A resistive wire 914 can be, for example, inserted through holes in a threaded end cap 916 and wrapped around the meltable alloy plug 912. In certain implementations, the meltable alloy plug 912 can be a metal solder having a relatively low melting point. For example, the meltable alloy plug 912 can be made from a lead/tin combination solder having a melting point of about 375° F. Similar to resistive wire 312 as described above, the resistive wire 914 can be constructed from a material that produces heat in response to an applied current. For example, the resistive wire 914 can be made from nickel chromium. The thickness of the resistive wire 914 can be selected such that the temperature of the wire, when an appropriate current is applied, exceeds the melting point of the meltable alloy plug 912. For example, a 24-gauge nickel chromium wire having a 0.020-inch diameter can heat to 400° F. at relatively low amperages as compared to a similar copper wire.

In certain implementations, the resistive wire 914 can be configured to melt the meltable alloy plug 912. In some examples, the force exerted on the piston 908 by the pressurized fluid can exceed the pressure exerted on the piston solely by the spring 910. As such, the pressurized fluid can push the piston 908, thereby exposing the exit ports 906 and establishing a fluid connection between the pressurized fluid reservoir 904 and the exit ports 906. The pressurized fluid can flow from the pressurized fluid reservoir 904 into the exit ports 906.

The piston 908 can also include one or more O-rings 918 positioned to prevent leakage of the pressurized fluid from the pressurized fluid reservoir 904. In some implementations, the O-rings 918 can be made from a thermoplastic elastomer such as synthetic rubber. The O-rings 918 can also be sized to produce a friction fit between the piston 908 and the body 902.

In operation, the pressure source 900 can be integrated into a therapy electrode such as therapy electrode 200 as discussed above. For example, the pressure source 900 can replace pressure source 240 as discussed in reference to therapy electrode 200. A controller, such as medical device controller 120, can be operably connected to the pressure source 900. The medical device controller 120 can be configured to provide an electrical signal to the pressure source 900 prior to delivery of, for example, a therapeutic shock to a patient. The electrical signal can be directed to the resistive wire 914, thereby heating the resistive wire 914. Once heated, the resistive wire 914 can melt the meltable alloy plug 912, which results in movement of the piston 908. As noted above, upon melting of the meltable alloy plug 912, the pressure exerted on the piston 908 by the pressurized fluid can result in movement of the piston 908. After movement of the piston 908, the pressurized fluid can flow into the exit ports 906. The pressurized fluid can flow through exit ports 906 into the fluid channel 230 and to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the resistance of the resistive wire 914, and desired timing for the release of the conductive gel, the medical device controller 120 can be configured to deliver an appropriate electrical signal (e.g., at a high enough current to heat the resistive wire 914 to melt the meltable alloy plug 912) at the appropriate time (e.g., providing for adequate timing for the pressurized fluid release and for the subsequent release of the conductive gel). In some examples, the pressure source 900 can also include a localized power source that, in response to the signal from the medical device controller 120, is configured to provide a current to the resistive wire 914, thereby heating the resistive wire 914 and melting the meltable alloy plug 912.

Pressure Source Having a Micro Drill

FIG. 10 illustrates a pressure source 1000 that includes a pressurized fluid reservoir 1002. As described above, the pressurized fluid reservoir 1002 can be made from a metal such as stainless steel. As shown in FIG. 10, a micro drill bit 1008 can be positioned proximate an end of the pressurized fluid reservoir 1002. In certain implementations, the micro drill bit 1008 can be a hardened steel drill bit having a diameter of approximately 0.02 inches. A spring 1006 can be positioned at an end of the pressurized fluid reservoir 1002 that is opposite the micro drill bit 1008. The spring 1006 can be configured to exert a small force (e.g., 0.5 N) on the pressurized fluid reservoir 1002, thereby holding the pressurized fluid reservoir 1002 against the micro drill bit 1008. However, the force exerted on the pressurized fluid reservoir 1002 by the spring 1006 can be configured to not move push the pressurized fluid reservoir 1002 against the micro drill bit 1008 with such force that the micro drill bit 1008 can puncture the pressurized fluid reservoir 1002 prior to activation of the micro drill bit 1008 (e.g., such that the movement of the micro drill bit 1008 results in puncture of the pressurized fluid reservoir, not the spring force exerted by spring 1006).

A motor 1010 can be operably connected to the micro drill bit 1008 to cause rotational motion of the micro drill bit 1008. In certain implementations, the motor 1010 can be a planetary gear motor configured to accept the micro drill bit 1008. Upon application of an electrical signal to the motor 1010, the motor 1010 can be configured to transfer a rotation motion to the micro drill bit 1008, causing the micro drill bit 1008 to spin in, for example, a clockwise direction. In certain implementations, the rotational motion of the micro drill bit 1008, in combination with the spring force applied by the spring 1006, can cause the micro drill bit 1008 to drill a hole into the pressurized fluid reservoir 1002. The pressurized fluid contained within the pressurized fluid reservoir 1002 can flow out of the pressurized fluid reservoir 1002 and through an exit port 1004.

In operation, the pressure source 1000 can be integrated into a therapy electrode such as therapy electrode 200 as discussed above. For example, the pressure source 1000 can replace pressure source 240 as discussed in reference to therapy electrode 200. A controller, such as medical device controller 120, can be operably connected to the pressure source 1000. The medical device controller 120 can be configured to provide an electrical signal to the pressure source 1000 prior to delivery of, for example, a therapeutic shock to a patient. The electrical signal can be directed to the motor 1010. In response to the electrical signal, the motor 1010 can apply a rotational motion to the micro drill bit 1008. The spring 1006 can exert a force on the pressurized fluid reservoir 1002, thereby pushing the pressurized fluid reservoir 1002 against the spinning micro drill bit 1008. The rotating micro drill bit 1008 can puncture the pressurized fluid reservoir 1002, thereby releasing pressurized fluid contained therein. The pressurized fluid can flow through exit port 1004 into the fluid channel 230 and to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the electrical requirements of the motor 1010, and desired timing for the release of the conductive gel, the medical device controller 120 can be configured to deliver an appropriate electrical signal (e.g., at a high enough current to operate the motor 1010) at the appropriate time (e.g., providing for adequate timing for the pressurized fluid release and for the subsequent release of the conductive gel). In some examples, the pressure source 1000 can also include a localized power source that, in response to the signal from the medical device controller 120, is configured to provide a current to the motor 1010, thereby rotating the micro drill bit 1008 for drilling into the pressurized fluid reservoir 1002.

Pressure Source Having an Expanding Release Mechanism

FIGS. 11A and 11B illustrate a pressure source 1100 that includes a pressurized fluid reservoir 1102. As described above, the pressurized fluid reservoir 1102 can be made from a metal such as stainless steel. FIG. 11A shows an exploded view of the pressure source 1100, while FIG. 11B shows an assembled view of the pressure source 1100. Unless specifically noted, both FIGS. 11A and 11B will be described simultaneously in the following description.

A puncturing pin 1104 can be positioned proximate an end of the pressurized fluid reservoir 1102. For example, the puncturing pin 1104 can be a hardened steel pin configured to pierce a pierceable end of the pressurized fluid reservoir 1102. An expanding release mechanism 1106 can be operably attached to the puncturing pin 1104. The expanding release mechanism 1106 can be configured to expand in response to certain stimulus. For example, the expanding release mechanism 1106 can be a wax motor that is configured to expand upon application of heat to the wax. In operation, a wax motor can be constructed to include a wax that expands as it melts. In certain implementations, a wax motor can include a wax configured to expand when melted, the wax having a melting point of approximately 125° F. to 175° F. For example, the wax motor can include a paraffin wax configured to melt at about 150° F. As the wax melts, the expansion of the wax can be used to apply a pushing force to another object such as the puncturing pin 1104.

As shown in FIG. 11B, a heating element such as resistive wire 1108 can be wrapped around or embedded in a wax motor (if used, for example, as the expanding release mechanism 1106) to melt the wax contained within the wax motor. Similar to resistive wire 312 as described above, the resistive wire 1108 can be constructed from a material that produces heat in response to an applied current. For example, the resistive wire 1108 can be made from nickel chromium. The thickness of the resistive wire 1108 can be selected such that the temperature of the wire, when an appropriate current is applied, exceeds the melting point of the wax used in manufacture of the wax motor (if used, for example, as the expanding release mechanism 1106). For example, a 24-gauge nickel chromium wire having a 0.020-inch diameter can heat to 400° F. at relatively low amperages as compared to a similar copper wire.

Upon expansion of the wax, the puncturing pin 1104 can puncture the pressurized fluid reservoir 1102, thereby resulting in release of the pressurized fluid contained therein. The pressurized fluid can be directed to one or more exit ports for delivery to one or more conductive gel reservoirs to facilitate release of the conductive gel.

In operation, the pressure source 1100 can be integrated into a therapy electrode such as therapy electrode 200 as discussed above. For example, the pressure source 1100 can replace pressure source 240 as discussed in reference to therapy electrode 200. A controller, such as medical device controller 120, can be operably connected to the pressure source 1100. The medical device controller 120 can be configured to provide an electrical signal to the pressure source 1100 prior to delivery of, for example, a therapeutic shock to a patient. The electrical signal can be directed to the expanding release mechanism 1106. For example, if a wax motor is used, the electrical signal can be directed to the resistive wire 1108. The resistive wire 1108 can heat the wax contained in the wax motor, resulting in expansion of the wax. The expansion of the wax can exert a pushing force on the puncturing pin 1104. The puncturing pin 1104 can puncture the pressurized fluid reservoir 1102, thereby releasing the pressurized fluid contained therein. The pressurized fluid can flow through one or more exit ports, into the fluid channel 230 and to each of the conductive gel reservoirs 210. The pressurized fluid can cause release of the conductive gel contained within the conductive gel reservoirs 210, resulting in the conductive gel flowing through the apertures in the electrically conductive layer that is proximate the patient's body. The medical device controller 120 can then facilitate delivery of the therapeutic shock.

Depending upon the electrical requirements of the expanding release mechanism 1106, and desired timing for the release of the conductive gel, the medical device controller 120 can be configured to deliver an appropriate electrical signal (e.g., at a high enough current to cause expansion of the expanding release mechanism 1106) at the appropriate time (e.g., providing for adequate timing for the pressurized fluid release and for the subsequent release of the conductive gel). In some implementations, the pressure source 1100 can also include a localized power source that, in response to the signal from the medical device controller 120, is configured to provide a current to the expanding release mechanism.

Use of Gel Deployment with an Ambulatory Medical Device

Figure 12:
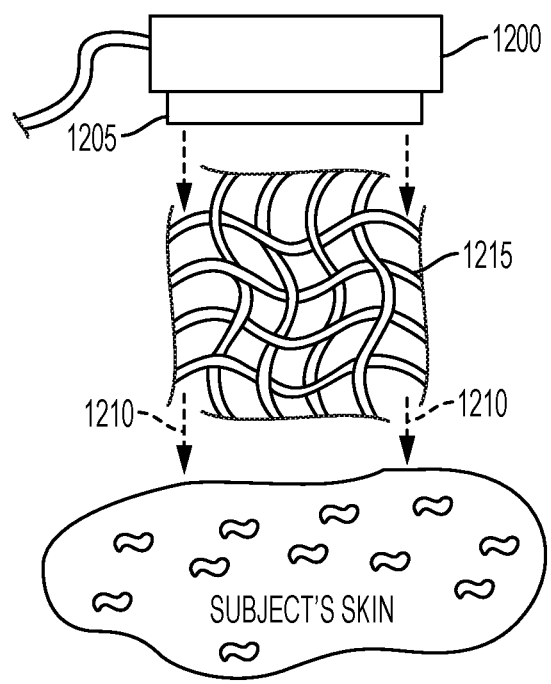
FIG. 12 depicts an interface between a therapy electrode and a patient's skin in accordance with an example of the present disclosure.

FIG. 12 depicts an example of conductive gel entering the area between a therapy electrode and the subject's skin after being released by, for example, a gel deployment devices including one of the pressure sources as described above (e.g., pressure sources 300, 400, 500, 520, 600, 700, 800, 900, 1000 and 1100 as shown in FIGS. 3, 4, 5A, 5B, 6, 7, 8, 9, 10, 11A and 11B). In one implementation, after release from a gel deployment device, the conductive gel can enter the area between a conductive surface 1205 of therapy electrode 1200 and the subject's skin, and can form a conduction path 1210 from the therapy electrode 1200 to the subject's skin. The conductive gel can cover conductive thread or mesh fabric 1215 that is part of a garment (e.g., garment 110), portions of which can be disposed between the subject's skin and the therapy electrode 1200. For example, the gel deployment device can be configured in a form of a removable receptacle. As such, after the pressure source is used and the gel is deployed, the gel deployment device can be removed and replaced.

Figure 13:
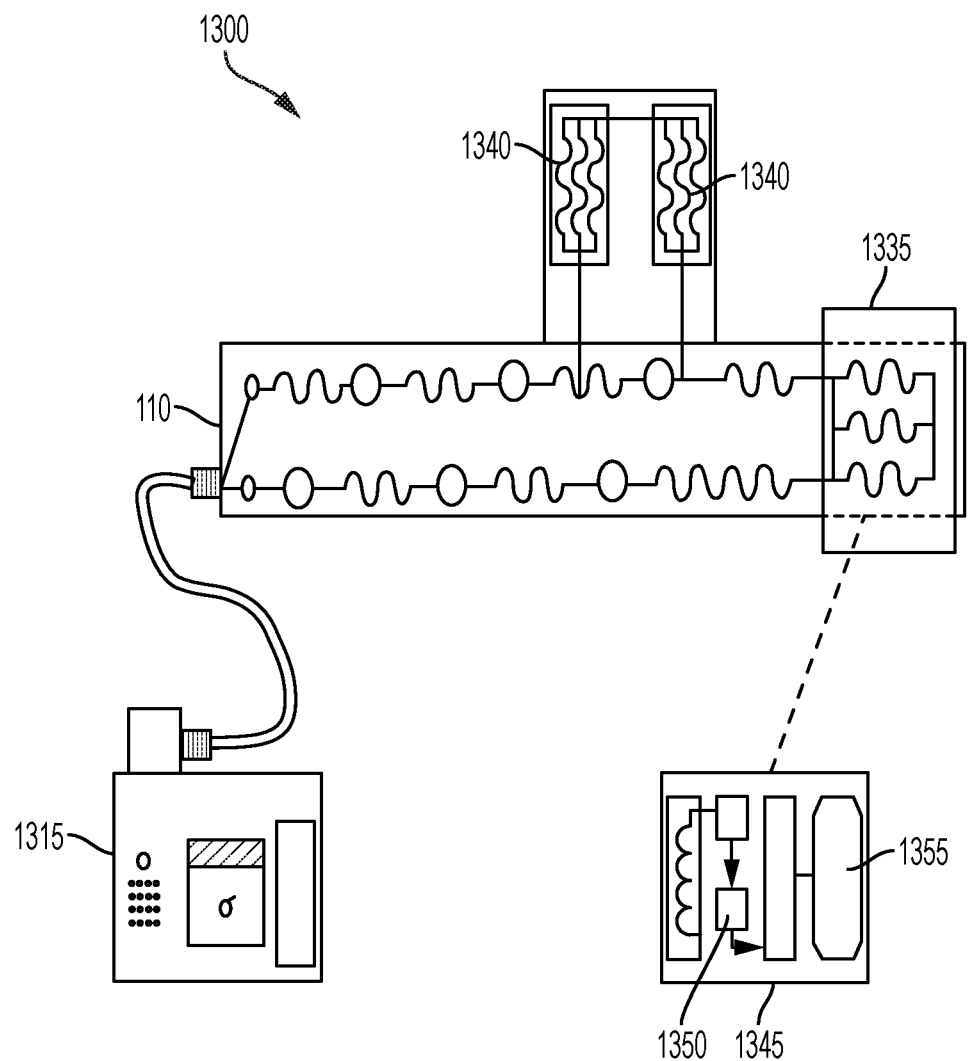
FIG. 13 depicts a schematic diagram illustrating various components of an external medical device in accordance with an example of the present disclosure.

FIG. 13 illustrates components of external medical device 1300 according to certain implementations, with sensing electrodes 1350 including at least one EKG (or ECG) electrocardiogram sensor, conductive thread 1305 woven into belt 1310 of garment 110, and gel deployment device 1345 disposed proximate to a first therapy electrode 1335 in garment 110.

In one implementation, a control unit 1350 can instruct the gel deployment device 1345 to release the conductive gel included in conductive gel reservoir 1355. The released conductive gel can reduce impedance between the subject's skin and first therapy electrode 1335. Therapy controller 1315 can apply treatment (e.g., a therapeutic shock) to the subject via first therapy electrode 1335 and second therapy electrode 1340 (that can include another gel deployment device 1345 for deployment of conductive gel between second therapy electrode 1340 and the patient's skin). During treatment, current can follow a path between the subject's skin and first therapy electrode 1335 and second therapy electrode 1340 via the conductive gel.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An electrode for providing electrotherapy from an ambulatory electrotherapy device comprising:
at least one reservoir comprising a conductive gel;
at least one pressure source comprising a chemical reaction chamber comprising
a first chemical and a second chemical isolated from each other by a mechanical barrier,
wherein the mechanical barrier is configured to be compromised upon receiving a signal from an electrotherapy device controller, and
wherein the first chemical and the second chemical come into contact when the mechanical barrier is compromised to produce a sufficient amount of pressurized fluid to generate a sufficient pressure within the chamber.

2. The electrode of claim 1, further comprising at least one release mechanism configured to compromise the mechanical barrier, thereby releasing the second chemical such that the second chemical reacts with the first chemical.

3. The electrode of claim 2, wherein the at least one release mechanism comprises a heat producing device or a mechanical device configured to facilitate movement of at least one of the first chemical and the second chemical.

4. The electrode of claim 1, wherein the mechanical barrier comprises at least one meltable membrane configured to isolate the first chemical from the second chemical.

5. The electrode of claim 1, wherein the first chemical is in solid form and the second chemical is in a liquid form, and the pressurized fluid produced comprises at least one of carbon dioxide, nitrogen, oxygen, and mixtures thereof.

6. The electrode of claim 1, further comprising an exit port connected to a fluid channel, wherein the exit port is configured to direct the pressurized fluid into the fluid channel.

7. The electrode of claim 1, wherein a pressure level of the produced pressurized fluid is between 15 psi and 40 psi.

8. A system for providing therapy to a patient, the system comprising:
a garment;
a monitor configured to monitor at least a physiological parameter of the patient; and
a plurality of therapy electrodes operably connected to the monitor and disposed in the garment, each of the plurality of therapy electrodes comprising a pressure source for providing a pressurized fluid to facilitate conductive gel deployment in a wearable medical device, the pressure source comprising a chemical reaction chamber comprising
a first chemical and a second chemical isolated from each other by a mechanical barrier,
wherein the mechanical barrier is configured to be compromised upon receiving a signal from an electrotherapy device controller, and
wherein the first chemical and the second chemical come into contact when the mechanical barrier is compromised to produce a sufficient amount of fluid to generate a sufficient pressure within the chamber.

9. The system of claim 8, wherein each of the plurality of therapy electrodes further comprise at least one conductive surface configured to deliver a therapeutic shock.

10. The system of claim 8, further comprising at least one release mechanism configured to compromise the mechanical barrier, thereby releasing the second chemical such that the second chemical reacts with the first chemical.

11. The system of claim 10, wherein the at least one release mechanism comprises a heat producing device or a mechanical device configured to facilitate movement of at least one of the first chemical and the second chemical.

12. A pressure source for providing a pressurized fluid to facilitate conductive gel deployment in a wearable medical device, the pressure source comprising:
a reservoir containing the pressurized fluid; and
at least one release mechanism configured to cause a release of the pressurized fluid from the reservoir to an exit port of the pressure source when the wearable medical device is preparing to deliver a therapeutic shock to a patient.

13. The pressure source of claim 12, wherein the at least one release mechanism comprises at least one heating element, or a piston positioned to block flow of the pressurized fluid from the reservoir to the exit port, wherein the piston is configured to slidably release the pressurized fluid to the exit port, or a movable piercing device positioned adjacent to a pierceable end of the reservoir.

14. The pressure source of claim 13, wherein the reservoir comprises a meltable plug positioned in contact with the at least one heating element and configured to melt upon application of a current to the at least one heating element, thereby resulting in release of the pressurized fluid through the exit port.

15. The pressure source of claim 13, further comprising a spring mechanism configured to slide the piston to facilitate release of the pressurized fluid.

16. The pressure source of claim 15, further comprising at least one retaining element configured to oppose a spring force exerted by the spring mechanism to prevent movement of the piston, wherein the at least one retaining element is positioned adjacent to at least one heating element and is configured to melt upon application of a current to the at least one heating element, thereby resulting in movement of the piston and release of the pressurized fluid to the exit port.

17. The pressure source of claim 13, wherein the moveable piercing device comprises a motor configured to move puncturing device through into the pierceable end of the reservoir, thereby resulting in release of the pressurized fluid.

18. The pressure source of claim 17, wherein the motor comprises at least one of a solenoid and an expanding wax actuator.

19. The pressure source of claim 12, wherein the pressurized fluid comprises at least one of carbon dioxide, nitrogen, oxygen, argon and mixtures thereof.

20. The pressure source of claim 12, further comprising:
a piercing device positioned adjacent to a pierceable end of the reservoir; and
a spring mechanism configured to facilitate movement of at least one of the piercing device and the reservoir, thereby resulting in a piercing of the pierceable end of the reservoir and release of the pressurized fluid through the exit port.

21. The pressure source of claim 20, wherein the spring mechanism comprises a meltable retaining mechanism positioned adjacent to at least one heating element, wherein the meltable retaining mechanism is configured to melt upon application of a current to the at least one heating element, thereby resulting in the movement of at least one of the piercing device and the reservoir.

22. The pressure source of claim 20, wherein the piercing device comprises a drill positioned such that a drill bit is adjacent to the pierceable end of the reservoir.

23. The pressure source of claim 22, wherein application of a current to the drill results in rotational movement of the drill bit such that the drill bit penetrates the pierceable end of the reservoir.

24. A system for providing therapy to a patient, the system comprising:
a garment;
a monitor configured to monitor at least a physiological parameter of the patient; and
a plurality of therapy electrodes operably connected to the monitor and disposed in the garment, each of the plurality of therapy electrodes comprising a pressure source for providing a pressurized fluid to facilitate conductive gel deployment in a wearable medical device, the pressure source comprising
a reservoir containing the pressurized fluid, and
at least one release mechanism configured to cause a release of the pressurized fluid from the reservoir to an exit port of the pressure source when the monitor is preparing to deliver a therapeutic shock to the patient.

25. The system of claim 24, wherein each of the plurality of therapy electrodes further comprise at least one conductive surface configured to deliver the therapeutic shock.

26. The system of claim 24, wherein the at least one release mechanism comprises:
   at least one heating element and a meltable plug positioned in contact with the at least one heating element and configured to melt upon application of a current to the at least one heating element, thereby resulting in release of the pressurized fluid through the exit port or a piston positioned to block flow of the pressurized fluid from the reservoir to the exit port, wherein the piston is configured to slidably release the pressurized fluid to the exit port or a movable piercing device positioned adjacent to a pierceable end of the reservoir.

27. The system of claim 24, wherein the pressure source further comprises:
   a piercing device positioned adjacent to a pierceable end of the reservoir; and
   a spring mechanism configured to facilitate movement of at least one of the piercing device and the reservoir, thereby resulting in a piercing of the pierceable end of the reservoir and release of the pressurized fluid through the exit port.

28. A method for providing electrotherapy from an ambulatory electrotherapy device comprising:
   providing an electrode;
   providing at least one reservoir comprising a conductive gel;
   providing at least one pressure source comprising a chemical reaction chamber comprising
      a first chemical and a second chemical isolated from each other by a mechanical barrier,
      wherein the mechanical barrier is configured to be compromised upon receiving a signal from an electrotherapy device controller, and
   wherein the first chemical and the second chemical come into contact when the mechanical barrier is compromised to produce a sufficient amount of fluid to generate a sufficient pressure within the chamber.

29. The method of claim 28, wherein the at least one pressure source comprises producing carbon dioxide by a reaction of the first chemical and the second chemical.

30. The method of claim 29, wherein the first chemical is a metal carbonate or bicarbonate and the second chemical is an acid.

31. The method of claim 28, wherein the at least one pressure source comprises producing carbon dioxide, nitrogen, oxygen, or mixtures thereof.

* * * * *

UNITED STATES PATENT AND TRADEMARK OFFICE
CERTIFICATE OF CORRECTION

PATENT NO. : 10,569,090 B2
APPLICATION NO. : 15/796043
DATED : February 25, 2020
INVENTOR(S) : Robert J. Hulings et al.

It is certified that error appears in the above-identified patent and that said Letters Patent is hereby corrected as shown below:

In the Specification

Column 11, Line 64 - delete "napthalate,", insert -- naphthalate, --
Column 14, Line 9 - delete "tirfluoroacetic", insert -- trifluoroacetic --
Column 24, Line 2 (TABLE 1) - delete "sodim", insert -- sodium --

Signed and Sealed this
Fifth Day of May, 2020

Andrei Iancu
*Director of the United States Patent and Trademark Office*